US009217181B2

(12) United States Patent
Flegel et al.

(10) Patent No.: US 9,217,181 B2
(45) Date of Patent: Dec. 22, 2015

(54) MOLECULAR STRUCTURE OF RHD NEGATIVE

(75) Inventors: Willy A. Flegel, Dieburg (DE); Franz F. Wagner, Ulm (DE)

(73) Assignee: DRK-BLUTSPENDEDIENST BADEN-WURTTEMBERG-HESSEN GEMEINNUTZIGE GMBH, Ulm (DE)

( * ) Notice: Subject to any disclaimer, the term of this patent is extended or adjusted under 35 U.S.C. 154(b) by 0 days.

(21) Appl. No.: 12/390,982

(22) Filed: Feb. 23, 2009

(65) Prior Publication Data

US 2011/0172406 A1    Jul. 14, 2011

Related U.S. Application Data

(62) Division of application No. 10/129,580, filed as application No. PCT/EP00/10745 on Oct. 31, 2000.

(30) Foreign Application Priority Data

Nov. 11, 1999 (DE) .................................. 99 12 1686
May 31, 2000 (DE) .................................. 00 11 1696

(51) Int. Cl.
  *C12Q 1/68* (2006.01)
  *C07K 14/705* (2006.01)
  *C12N 15/52* (2006.01)
(52) U.S. Cl.
  CPC ............ *C12Q 1/6883* (2013.01); *C07K 14/705* (2013.01); *C12N 15/52* (2013.01); *C12Q 2600/156* (2013.01); *C12Q 2600/16* (2013.01); *C12Q 2600/172* (2013.01)
(58) Field of Classification Search
  None
  See application file for complete search history.

(56) References Cited

U.S. PATENT DOCUMENTS

| | | | |
|---|---|---|---|
| 5,474,796 | A | 12/1995 | Brennan |
| 5,654,419 | A | 8/1997 | Mathies et al. |
| 5,972,602 | A | 10/1999 | Hyland et al. |
| 6,821,724 | B1 | 11/2004 | Mittman et al. |

FOREIGN PATENT DOCUMENTS

| | | |
|---|---|---|
| WO | 98/45712 A2 | 10/1998 |
| WO | 99/37763 A2 | 7/1999 |
| WO | 99/47555 A1 | 9/1999 |

OTHER PUBLICATIONS

Okuda, H et al. Sequence analysis of the spacer region between the RHD and RHCE genes. Biochem. Biophys. Res. Commun., vol. 263, pp. 378-383, Sep. 1999.*
Chien-Feng, S et al. RHD gene polymorphisms among RHD-negetive chinese in Taiwan. Vox Sanguinis, vol. 75, pp. 52-57, 1998.*
Matassi, G. et al. Characterization of the recombination hot spot involved in genomic rearrangement leading to the hybrid D-CE-D gene in the D VI phenotype. Am. J. Hum. Genet., vol. 60, pp. 808-817, 1997.*
Flegel, WA. et al. Rh phenotype prediction by DNA typing and its application to practice. Transfusion Medicine, vol. 8, p. 281-302, Dec. 1998.*
Gassner, C. et al. RHD/CE typing by polymerase chain reaction using sequence-specific primers. Transfusion, Vo. 37, p. 1020-1026, 1997.*
Beckers, E.A.M. et al. Characterization of the hybrid RHD gene leading to the partial D category IIIc phenotype. Transfusion, vol. 36, p. 567-574, 1996.*
Cherif-Zahar, B. et al. Molecular defects of the RHCE gene in Rh-deficient individuals of the amorph type. Blood, vol. 92, No. 2, p. 639-646, Jul. 1998.*
Avent, N.D., et al., Evidence of genetic and diversity underlying RhD-, weak D (Du), and partial D phenotypes as determined by multiplex polymerase chain reaction analysis of the RHD gene, Blood, W.B. Saunders, Philadelphia, Va., US, vol. 89, No. 7, Apr. 1997, pp. 2568-2577, XP002108680, ISSN 0006-4971.
Blunt, T., et al., Serotype switching in a partially deleted RHD gene, VOX Sanguinis, vol. 67, No. 4, 1994, pp. 397-401, XP000926512.
Carritt, B., et al., Evolution of the Human RH (Rhesus) Blood Group Genes: a 50 Year Old Prediction (Partially) Fulfilled, Human Molecular Genetics, 1997, 6(6), 843-850.
Carritt, B., et al., Rh Null Phenotypes Are Not Due to a Gross Deletion and Can Occur on Different Rh Genetic Backgrounds, Ann. Hum. Genet., 1993, 57, 273-279.
Cherif-Zahar, B., et al., Organization of the Gene (RHCE) Encoding the Human Blood Group RhCcEe Antigens and Characterization of the Promoter Region, Geneomics, 1994, 19-68-74.
Cobley, V., et al., Human DNA sequence clone RP3-469D22 on chromosome 1p35. 1-36.13, contains the 5' part of the gene for RHCE, Database EM_HUM 'Online! EMBL; Aug. 1998, p. 1-3, retrieved from EBI, accession No. HS469D22, Data base accession No. AL031284, XP002178290.
Hu, G., Human Small Membrane Protein 1 (SMP1) mRNA, EMBL Sequence Database, XP002170737, Heidelberg De cited in the application Accession No. AF081282.

(Continued)

*Primary Examiner* — Stephanie K Mummert
*Assistant Examiner* — Aaron Priest
(74) *Attorney, Agent, or Firm* — Pillsbury Winthrop Shaw Pittman LLP

(57) ABSTRACT

The present invention relates to a nucleic acid molecular structure representing the Rhesus genes locus comprising the RHD, SMP1 and RHCE genes and/or the Rhesus box(es), preferably the hybrid Rhesus box, the upstream Rhesus bar and/or the downstream Rhesus box. Furthermore, the invention relates to a process for the specific detection of the common RHD negative haplotypes. The invention further relates to the detection of RHD positive hyplotypes in D-negative individuals. Various mutations in the RHD gene have been identified that allow for the development of diagnostic tools. The invention also relates to oligonucleotides, that specifically hybridize to the hybrid box, preferably the breakpoint or breakpoint region or to the upstream and downstream Rhesus boxes. Additionally, the invention relates to kits comprising or employing the above recited compounds of the invention.

12 Claims, 37 Drawing Sheets

(56) References Cited

OTHER PUBLICATIONS

Figure 1:
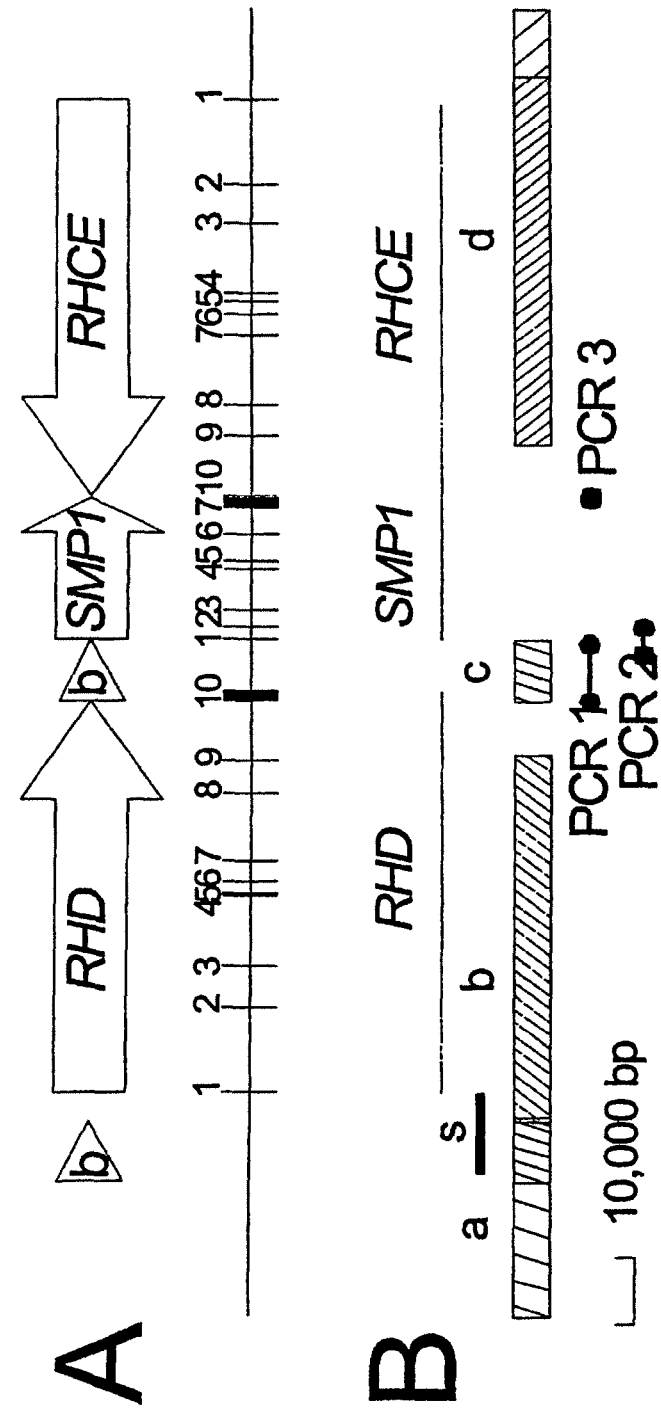

Le Van Kim, C., et al., Molecular Cloning and Primary Structure of the Human Blood Group RhD Polypeptide, Proc. Natl. Acad. Sci. USA, 1992, 89, 10925-10929.

Okuda, H., et al., Sequence Analysis of the Spacer Region between the RHD and RHCE Genes, Biochemical and Biophysical Research Communications, 1999, 263, 378-383.

Robles, et al., A Parallel-Stranded DNA Triplex Tethering a Hoechst 33258 Analogue Results in Complex Stabilization by Simultaneous Major Groove and Minor Groove Binding, J. Am. Chem. Soc., 1996, 118, 5820-5821.

Singleton, Belinda K., et al., The Presence of an RHD Pseudogene Containing a 37 Base Pair Duplication and a Nonsense Mutation in Africans with the Rh D-negative Blood Group Phenotype.

Wagner, Franz F., et al., RHD Gene Deletion Occurred in the Rhesus Box, Blood, 2000, 95:12, 3662-3668.

Okuda, Hiroshi, et al., Sequence Analysis of the Spacer Region between the RHD and RHCE Genes, Biochemical and Biophysical Research Communications, 1999, 263, 378-383.

Flegel, Willy A., The Genetics of the Rhesus Blood Group System, Dtsch Arztebl, 2007, 104(10):A 651-7.

Wagner, F.F., et al., RHD Gene Deletion Occurred in the Rhesus Box, Blood, 2000, 95(12):3662-3668.

Sekizawa, et al., Noninvasive prenatal diagnosis using a sgnal fetal nucleated erythrocyte isolated by micromanipulation from maternal blood, Methods Mol. Med., 1998, 16:275-85.

Zhang, et al., Whole genome amplification from a single cell: implications for genetic analysis, Proc. Nat'l Acad. Sci. USA, 1992, 89:5847-51.

Grothues, et al., PCR amplification of megabase DNA with tagged random primers (T-PCR), Nucleic Acids Research, 1993, 21(5):1321-2.

Daniels, G., "Human Blood Groups," Molecular Genetics of the Dipolymorphism, European/African/Asians, 2002, pp. 204-206.

Daniels, G., "Human Blood Groups," Molecular Genetics of the Dipolymorphism, European/African/Asians, 2002, pp. 208-209.

Daniels, G., "Human Blood Groups," Molecular Genetics of the Dipolymorphism, European/African/Asians, 2002, pp. 218-219, 221-223.

Flegel, W.A., "Genetik des Rhesus-Blutgruppensystems", Dtsch Arztebl, 2007, 104(10):A 651-7.

Lowe, T., et al., "A Computer Program for Seection of Oligonucleotide Primers for Polymerase Chain Reactions", Nucleic Acids Research, 1989, 18(7):1757-1761.

Okuda, H., et al., "The RHD Gene is Highly Detectable in RhD-negative Japanese Donors," Journal of Clinical Investigation, 1997, 11(2):373-379.

Reid & Lomas-Francis, "Rh Blood Group System," The Blood Group Antigen FactsBook, 2004, pp. 109-110.

Wagner, F.F., et al., "Molecular Basis of Weak D Phenotypes", Blood, 1999, 93(1):385-393.

Wagner, F.F., et al., "RHD Gene Deletion Occurred in the Rhesus Box", Blood, 2000, 95(12):3662-3668.

Warren, W.J., et al., Principles and Methods for the Analysis and Purification of Synthetic Deoxyribonucleotides by High-Performance Liquid Chromatography, Molecular Biotechnology, 1995, 4:179-199.

\* cited by examiner

Fig. 3

```
-- Rhesus box ---------------------------------------------->
gcatgcgcgactgagccgggtggatggtactgctgctccgggtgtctg
gaggctgtggccgtttgttttctgttgctaaaatcggggggagtgaggcggg <-- SMP1 Exon 1 (91 bp, 5'UTR)-------

-- SMP1 Exon 1 -------------><---- Intron ~ 2,000 bp
...actgcacgacggggctgactgacgt...

-- Intron ----><---- SMP1 Exon 2 (106 bp, 93 translated)-----
...agctgaaaaaaATGTCTGGATTTCTAGAGGGCTTGAGATGCTCAG...

-- SMP1 Exon 2 -------------><---- Intron ~ 2,500 bp
...GCTTCCATTGCTGCTGGTGTACTAgt...

-- Intron ----><---- SMP1 Exon 3 (113 bp, all translated)-----
...agTTTTTTACAGGCTGGTGGATTATCATAGATGCAGCTGTTATT...

-- SMP1 Exon 3 -------------><---- Intron ~ 8,000 bp
...TATAGCAACCATAGCCTTCCTAATgt...

-- Intron ----><---- SMP1 Exon 4 (68 bp, all translated)-----
...agGATTAATGCAGTATCGAATGGACAAGTCCGAGGTGATAGTTA...

-- SMP1 Exon 4 -------------><---- Intron ~ 1,400 bp
...TGAAGGTTGTCTGGGTCAAAACAGgt...
```

Fig. 3 cont.

```
Intron ---><--- SMP1 Exon 5 (93 bp, all translated) -----
......agGTGCTCGCATTGGCTTTCGTTGGTTTCATGTTGGCCTTTG...

-- SMP1 Exon 5 ---------><--- Intron ~ 4,000 bp
...TTTTTGGAGGTTATGTGCTAAAGgt..................

Intron ---><--- SMP1 Exon 6 (61 bp, all translated) ------
......agAAAAAGACATAGTATACCCTGGAATTGCTGTATTT........

-- SMP1 Exon 6 ---------><--- Intron ~ 4,000 bp
...TCCAGAATGCCTTCATCTTTTTGgt

Intron ---><--- SMP1 Exon 7 (1,703 bp, 47 translated)----
......agGAGGGGCTGGTTTTAAGTTTGGCCGCACTGAAGACTTATGGCAGT <--------- RHCE Exon 10 ------
-- SMP1 Exon 7 --------------------------------------
-------- SMP1 Exon 7 --->
GAacac....agcatcatcctaatgaaactaaacattattttaaac --------- RHCE Exon 10 -----------------------------
ttattaaattgactcttaaactaagtttttagtctttaattttttaatatcaa >---- Homology with RHD -
-- RHCE Exon 10 -------------------------------------
atctgtctctgaccttgtttcattatacataaggagctttgctgtcatgagcgtttc
```

Fig. 3 cont.

```
---------- Homology with RHD ----------------------------
----------- RHCE Exon 10 ---------------------------------
tcacgtacaaatgcaggcaacagtgagaggaagttgtcttgtt -- Homology with RHD -------------------------------------
-- RHCE Exon 10 ------------------------------------------
tttgaacaggccttgttttcttggatgctttgcTTAAAATCCAACAGCCAAATGAGG
```

Fig. 5

```
attcactatcacaagaacagcacgggtaa
**************************
**-*******g******************

------rez7------->
gacctgtccccatgattcagttacct
**************************
************************** cccactgggtccctcccacaacgcatgggaattcaggatgagattt
**********************************************
********************************************** gggtggggacacaaccctatcattccaccatggcccctcccaaa
**********************************************
********************************************** tttcatgtcctcacatttcaaaaccaatcacaccatcccaacagtccctc
**********************************************
********************************************** aaagtcttaaatgattcagcattaactcaaaagtccacagtctaatgtc
**********************************************
**********************************************
```

Fig. 5 cont.

```
tcatctgagacaaggcaagtcctttccatttatgagcctataaaatccaa
**************************************************
***********************c********************** agcaagttagttacttcctagatacaatggggtacaggcattgggtaaa
*************************************************
*********a*********************************** tacagccattccaaatgggataaattgtcaaaacaaagaggctacaggc
*************************************************
************************************************* ccatgagagtccaaaatccagtgggcagtcaaatcttaaagctccaaaat
**************************************************
************************************************** gatctcct-ttgactccacatctcacatccaggtcacgcagatggaagg
*************************************************
*********c*********************************** ggtgggttcccatggtcttgggcagctctgccccctgtacctttgcagggt
**************************************************
**************************************************
```

Fig. 5 cont.

acagcctccctctcagctgctgctttcatgggctggcattgagtgtctgcagc
****************************************************
********************************************a*
                                              ^^^^^^ ttttccaggtacacggtgcaagctgtcggtggatctaccattctggggtc
**************************************************
****************************************** tggaggacctcttctcacagctccactagtggtgcccagtagggactg
************************************************
********************************************* tgtgtggggtctctgacccacatttcccttctgcactgccctggcagag
**************************************************
****************************************** gatctccatgagggccctgctcctgcagcaaacttctgactggcatcca
**********************************************c*
****************************************
                                       ^^^^^^ ggcatttccgcacatcctctttaatctaggcgaaggtttccaaacccccaa
**************************************************
*******************************************g

Fig. 5 cont.

```
ttcttgacttctgtgcactcgcagtctcaacaccacatgaagctgtcaa
*************************************************
***** ggcttggggcttgcactccccgaagctacagcccaagctctaccttgcct
**************************************************
***** ccgtcagtcatggttgggagtggctgggatgcaggcaccaagtccta
************************************************
t********************************************** ggctgcacacagcatgaggaccccggcctggccaacaaaaccatttttt
*************************************************
*****

+-- breakpoint region ->
        +-- identity region -> cctgatacctctggacctgtgatggaggggttgccataaagacctctga
*************************************************
*************t******************************** catgccctggagacattttcccattgtcttggaattagcatttggctc
*************************************************
*****
```

Fig. 5 cont.

ctgttactcatgcaaatttctgcagccagcttgaatttctcctcagaaaa
**************************************************
********
      ^^^^^^ tgggaattttctttctatcacattgtcaggctgcaaattttccgaactt
*************************************************
******** ttatgctctgcttccctttataaaactgaatgtctttaacagcacccaag
**************************************************
******** tcacctcttgaatgctttgctgtgcttagaaattctcctgccagatactct
***************************************************
******** aaatcatctctctgaagttctacaaatatctcgtgcaggggca
******************************************
******** aaatgccgccagtatctttgctaaaacataacaagagtcccctttgctcc
**************************************************
********

Fig. 5 cont.

agttcccaacaagttcctcattccgtctgagaccacctcagcctatgga
**************************************************
************************************************** ctttattgtccacagtgctatcagcatttgggcaaagccattcaacaag
**************************************************
************************************************** tctctaggaagttccaaactttcccacattgcctgtcttcttctgagcc
**************************************************
************************************************** ctccaaactgttccaaaccctgcctgttaccagttccaaagtcacatac
**************************************************
************************************************** ccattttgagtatctacggcagcacccccactctactggtaccaatttag
**************************************************
************************************************** ccactgaagtagttggagaacagaagtaatagactctggtttacattgta
**************************************************
************************************************** aaagcttctctgtggctgctgtgtgaagaaaatatgagaatgaagccc
**************************************************
**************************************************

Fig. 5 cont.

```
caagatgaagcaggacacagttgcagtggttagagtaagaaatgctgct
************************************************
* ggctggcactgaagtgatagcctggaggtttgtgtgcacatgcatgtg
************************************************
** tatgtgttttacgatagtaggcccaacagat
*******************************

<-- breakpoint region ---+
actgtaatccacacttgtttttttt----ga
****************************tttt**
**********************tttt gacagagtctcacctgttgcctagactagaatgc
********************************** agtggcacaatcttgctcactacaacctccacctcccaggttcaaacaatc
***************************************************
*
```

Fig. 5 cont.

```
ctgtgcttcagcctcccgagtagttgggattacaggtgtgtgccacc
***********************************************
*** gtgccagctatattttgtatttttagcagagatgggatttgccacat
***********************************************
***********************************************
* tggccaggctggtcttgaactcctgacctcaagcaatcctcccaccta
***********************************************
**** gcctcccaaagtgctgagccaccacacctggccgcaactgatttttaatc
***********************************************
*********************************************** atgaaatgacacatacatttaaaaaacccatacctatatattcctggc
***********************************************
* tagtactcttcacatctatatcatcaaaaacaaagaaagtatgtgaaact
***********************************************
*
```

Fig. 5 cont.

```
gacacagccaaggggagactaaggagacataacaattaactgtaatgtgg
**************************************************
* tattctggagggatcctgaacagaaaagacattaggcaaaaactaa
**********************************************
********** agaaatctgaataaaatgtggatgtcagttaataatgtatcatatta
***********************************************
*

<-- identity region -->
gtccagtaattgtaacaaatataccacaataatgaaagccattaattata
*************************-************************
* gggaaaatggaggggttaatatgggtggctggcttttgctatttctagcag
**************************************************
* ctccatttatctgcaaaagacaaacattcattaagtcccaaaaggtaaa
********a************************************
*******a*
```

Fig. 5 cont.

```
gaatgacaaattaagcatgtatcttattagtaagtaatataagatg
**********************************************
**
ctcactcctatttataaatatttgacaatcatgttaaggccacaaaagag
******a***************g*********g********
*****a*************g*
aaaaagggtagggcaaaaacgcaaagagagaaggagttagtatctttt
**********************************************
***
ctcccgcactcattagctattaaagaggatgtttgtttaaagctgctca
**********************************************
*
gagctggtaaactaagtgttaagtcactaacgggaatttaaaaggtttcat
**********************************************
**
taagaactgcctgcactagattcctccaccctgagacattaaacaatcac
**********************************************
**
```

Fig. 5 cont.

```
gataaacctcctgagtgggtaagaacttgtccatttaaaaacaggctatag
*************************g*********************** *
************************g********************* * attgtatcatgcagttttatctactaatcggctaa
**-***************************
****-*--**************************** tatcccgcccaaaac----aaaaaaccccaaa
*gca*********-*aaac***a*****
*gca*********-*aaac*****a*******
<-------rnb31-------mm gggatgaaagtttcatccatcaaaggaaaacaac
**********************************
**********************************
```

Fig. 8

Hybrid Rhesus box of RHD negatives

5' ctagaaaacactttgtcattttagaggtgtta
(start of Rhesus box)
tccaatgttcgcgcaggcactggagtcagagaaaatggagttgaatcctttctctgccactc
tttgaggagaatctcaccatttattatgcactgtagaatacaacaataaaatacagccatgt
accacataacaacatcttggtaaacaacagactgcatatatgatggtggtcatccagtaagc
taaggttaatttattattattcccttttttttttcttttttttgagatgtagtcttactctg
tcacccaggctagagtgcaatggcaccatcttggctcactgcaacctctgcctcctgggttc
aagcgaatctcctgcctcagcctccgaagtagctgggaattacaggcacccaccacatctgg
ctaattttttgtatttttagtaaagatggggtttcaccatgttggccaggctgatctcaaac
tcctgacctcaagtgatctgcctgcctcggcctcccaaagtgctgggaccataggcctgagc
cactgtgcccggccttgtttgcttttttaacagttaacagtgtgctcatagaaactgctttg
acatgactgcaatcatgtgcttcatagaaacttaattagattataccactagagtcttcaga
tttttatactttttttttgaaacggagtctcactctgtcaccaggctggagtgcagtgccg
caatctcagctcgccgcaacctccgcctcccaggttcaagtgattctcctgcctcagcctcc
cgagtagctgggattacaagtgcacactaccacgcccagctaattttttgcattttactaga
cagggtttcaccatgttggctaggatagtttcaccaggatctcttggcctcatgatcagcct
gcctcggcctcccaaagtgctgggattacaggtgtgagccaccgtgcccagcctatacttcc
cttttttgaataccatttggcgttttgaagaattaacagctttgtgaacgtggcagtgcttgt
gattcaggcttccactgagaccaaggggagaacctggttgcaggacaaacagacggacagcg
tgtggcagtgtttaaatgctcttctgaaggctgatacgacagctctctgtgcactgattgta
tacgcatcccaagattatattattgttttctattgctatgtgtcacactttgccaaacagga
tgtggaaaatgaataagcggttttcttaggcacttcttaacagacaattggtcaaaatgaac
tccattgcttaagaaacacataaacaccatttagtcactgaatatagctatatgtatggttg
ctactatggggaatcttgttttgccaattttctttgaaaattctggcagaccaaggttcttt
ttgtttacacaatacttgaaaaataaaaatgaacaagccaacaaactaccaagttttcactt
acataaatgtagttacatacagaaaatgtgactgtgaatttttctaggacttttaaactat
aagcactatttgcacgaaagagaaccaatctatcaattacaaactcacataatttacagat
tttttttttccctacacagcacataaaacagaaggaatttgaagccaccctccaaacacaggg
gaaggaggctgtgtgtatatcctcattgtctttcacattctaaggtggttccactcagtgac
tgaaatccttaagtgttgtattagtcggcttgggctaccataacagcagcttaaactgttgt
taagccactcagacttaaacaacagaaatttatttccttatagttctggaggctggaagttc
aaggtgccggcaaggctggtttctggtgagacctctctccctgtcttgcagatggctgcctc
ctccctgtgtcctcatagagcctgtcctctgcttttacacttctggtgtcatcttccttttt
ttttttttttgagacagagtctcgctctatcgcccaggctggagtgcagtggcccgatcga
tctcggctcactgcaacctctgcctcccaggttcaagcaattctcctgcctcagcctcccga
gtagctgggactacaggtgcccgccatcatgtctggctaatttttgtatttttagtagagac
agggtttcaccatattggccaggctggtctccaactcctgaccttgtcatctgcctgcctcg
gcctcccaaagtgctaggattacaggcgtgagccaccgcacccggcctctttctcttcttat
aaggacaccagtcctattagattagggctccaccctcatgacctcatttgacc ttaactatt
atttctttaaagcacctatttccaaatatagtcactttaggggttagggcttcaaaatatga
atctgagggagatcaattcagtaaatagcagtagtcattaacggacaatatatacaaagata
atttcgtgattactgtccttatgcataaatgtcctcagtgttccactgcctttatccagatt
tactatcacaaagactttgctctgagaaaatgtgatttctttctttttttttttttttga
gacagagtctcactctgtcacccaggctggagtgcagtggtgcaatctcggctcactgcaat
ctccgcctcccaggttcacgccattctcttgcctcagtctcccgagtagctgggcctacagg

Fig. 8 cont.

Hybrid Rhesus box of RHD negatives

```
cgcccgccaccctgcccagctaattttttgtattttagtagagacggggttttcaccatgtt
agccaggatggtctcaatctcctgacctcgtgatccacctgcctcagcctcccaaagtgctg
ggattacaggcatgagccaccgcgcccagcagattttttttttttttttttttttgagat
ggagtcttgctgtgttgcccagcctggagtgcagtgttatgattttggctcactgcaacctc
tgtctaccatgttcaagcgattctcccacctctgcctcccgtgtagctgggatcacaggcac
acgccaccacacctagctacttttgtattttagtagaaatggggtttcaccatgttggcc
aggatggtcccgaactcctgacctcaagtgatcctcctgcctcggcctcccaaagtgctggg
attacaggtgtgagccactgtgcctggccaaaaatgtgatttcttatttcccacattgccaa
ttccatttcaattaactataatagctatgtctattgagcactcaagtgtattctagaaactg
ttcctgattctggggatatatccatgaatcaactatagtccctgttattaagtaatctgtag
tctgactaaaccattagaaatttaaaaaatggctactttcaaagacatcttggagttcagga
gtcccacactgcgaaccatattacctaataatccaacctgcttgtaattcacttatttaacc
aatatttattgagtgccaactttgagcctaagatacagcagtaaacaaatggataaagtccc
tgtcctcatgaaacttgtattctaatggaagaaacagaaaacaaacagatataggatgtaat
atcaggtagggataaatactttgaattcaaacaaaagtatacgtagtcagggttcgccaaag
agacacagccaatcggatacatagatatataaaagagggtttatgagttagaaagggctcac
atgattacagaggctgagaagtcccacagcagattgtctgcaagctggagacccagggatac
tggtagcatggctcagtccaagtcccaaagcctcagaatcaggaaagctgatgatataattc
ttagcccaaaggccttagaaccccagcggtgacggaaaggctgatgtaggtcctggagtcct
gagacccaacagcctgggatcctgaaatccaagggcaggaatggaagcgtgtattccagctc
caagagagtaagaccaatttgcctttcttccgttttgtttcaagccacctgcacattgagg
gcggatggttccctcttagtccattcagtcatatatcaatctcttctggaaatacccctcaca
gacacactaacaaataatgcctttccagttctctaggtattctttaatccagtcaagctgac
acctaaaattaaccatcacaaaagttaaggagaaagaagacaacttgtaggggaggctgcta
tgcaagacagtgtgtgaaggaagggctctctgaagaggttaatatctgagcagagacttgaa
tgaagtgaagaagtgagccatgtgggtatggggaatacaacttccaggtagagaagacaagt
gtggtgtgtatcagggtcagcaaagaagccatgtgacagagaagggtgggccagggagagac
ggataagtgatctaactcctgaggaggtggcctggccaggagctagagcatgaagatctcgt
aggactttattctgcaaggtgaaaagccattgtattagtctgttcacaaacccgagactagg
caatttacaaaagaaagagaggtttaatggacttacagttccacatggctggggaggcctca
caatcatggcgaaaggcaatgaggagcaagtcacgtcttacgtggatggcaggcaaagacaa
agacagcttgtgcagagaaactccccttatagagccatcagatcctgttagacttattcac
tatcacaagaacagcacgggtaagacctgtccccatgattcagttacctcccactgggtccc
tcccacaacgcatgggaattcaggatgagatttgggtggggacacaaccaaaccctatcatt
ccacccatggcccctcccaaatttcatgtcctcacatttcaaaaccaatcacaccatcccaa
cagtccctcaaagtcttaaatgatttcagcattaactcaaaagtccacagtctaatgtctca
tctgagacaaggcaagtccttccatttatgagcctataaaatccaaagcaagttagttact
tcctagatacaatgggggtacaggcattgggtaaatacagccattccaaatgggataaattg
gtcaaaacaaagaggctacaggcccatgagagtccaaaatccagtggggcagtcaaatctta
aagctccaaaatgatctcctttgactccacatctcacatccaggtcacgcagatggaagggg
tgggttcccatggtcttgggcagctctgccctgtacctttgcagggtacagcctccctctc
agctgctttcatgggctggcattgagtgtctgcagcttttccaggtacacggtgcaagctgt
cggtggatctaccattctggggtctggaggacctcttctcacagctccactaggtggtgccc
cagtagggactgtgtgtggggtctctgaccccacatttcccttctgcactgccctggcagag
gatctccatgagggccctgctcctgcagcaaacttctgactgggcatccaggcatttccgca
```

Fig. 8 cont.

Hybrid Rhesus box of RHD negatives catcctctttaatctaggcgaaggtttccaaaccccaattcttgacttctgtgcactcgcag
tctcaacaccacatggaagctgtcaaggcttggggcttgcactccccgaagctacagcccaa
gctctaccttgcctcccgtcagtcatggttgggagtggctgggatgcagggcaccaagtccc
taggctgcacacagcatgaggaccccgggcctggccaacaaaaccattttttcctgatacct
ctggacctgtgatgggaggggttgccataaagacctctgacatgccctggagacatttccc
cattgtcttgggaattagcatttggctcctgttactcatgcaaatttctgcagccagcttga
atttctcctcagaaaatgggaattttcttttctatcacattgtcaggctgcaaattttccg
aactttatgctctgcttcccttataaaactgaatgtctttaacagcacccaagtcacctct
tgaatgctttgctgcttagaaatttctcctgccagatactctaaatcatctctctgaagttc
aaagttctacaaatatctcgtgcaggggcaaaatgccgccagtatctttgctaaaacataac
aagagtcccctttgctccagttcccaacaagttcctcatttccgtctgagaccacctcagcc
tatggactttattgtccacagtgctatcagcattttgggcaaagccattcaacaagtctcta
ggaagttccaaactttcccacatttgcctgtcttcttctgagccctccaaactgttccaaac
cctgcctgttacccagttccaaagtcacatacccattttgagtatctacggcagcacccca
ctctactggtaccaatttagccactgaagtagttggagaacagaagtaatagactctggttt
acattgtaaaagcttctctgtggctgctgtgtgaagaaaatatatgagaatgaagccccaag
atgaagcagggacacagttgcagtggttagagtaagaaatgctgctggctggcactgaagtg
atagcctggaggtttgtgtgtgcacatgcatgtgtatgtgttttacgatagtaggcccaaca
gatactgtaatccacacttgttttttttttttttgagacagagtctcacctgttgcctag
actagaatgcagtggcacaatcttggctcactacaacctccacctcccaggttcaaacaatc
cttgtgcttcagcctcccgagtagttgggattacaggtgtgtgccaccgtgcccagctatat
ttttgtattttagcagagatgggattttgccacattggccaggctggtcttgaactcctg
gcctcaagcaatcctcccaccttagcctcccaaagtgctgagccaccacacctggccgcaac
tgattttaatcatgaaatgacacatacatttaaaaaacccaatacctataatattcctggc
tagtactcttcacatctatatcatcaaaaacaaagaaagtatgtgaaactgacacagccaag
gggagactaaggagacataacaattaactgtaatgtggtattctggaggggatcctggaaca
gaaaaagacattaggcaaaaaactaaagaaatctgaataaaatgtggatgtcagttaataat
aatgtatcatattagtccagtaattgtaacaaatatacccaataatgaaagccattaattat
agggaaaatggaggggttaatatgggtggctggcttttgctatttctagcagctccatttta
tctacaaaagacaaacattcattaagtcccaaaaggtaaagaatgacaaattaagcatgta
tcttattagtaagagtaatataaagatgctcactcatatttataaatatttgacaatgatgt
taaggccagaaaagagaaaaagggtaggggcaaaaaacgcaaagagaaaggagttagtatc
ttttctcccgcactcattagctattaaaagaggatgtttgtttaaagctgctcagagctggt
aaactaatgttaagtcactaacgggaatttaaaaggtttcattaagaactgcctgcactaga
ttcctccaccctgagacattaaacaatcacgataaacctcctgagtggtaagaacgtgtcca
tttaaaaacaggctatagattgtcatgcagttttatctactaatcggctaatgcaccgccaa
aaacaaacaaaaaacccaagggatgaaagtttcatccatcaaaggaaacaacagtcacct
tggttcccatcccactcatatactgccgccgtacatgtcaatcagatgaacctgtgcgtatc
tcttaacgacaattgacccacctttttaactgaagtgaaggggggttctgctccgcgaccac
ttcctggatctctcccttcaccctctgtgttctttcgggtgcaccatcgggtcaaagccgca
gcaacgccgtctctgtgtgatcgcatgtgccttctgcacacgaccttcccccgagagtgac
cagctaccggacaggcaccaaggagggctaccgagcacctcccggaccggcggctgcaggat
cgcgagcgcctccgctagggagaccgcacgttgcgcctgtgcttcctgcggtggcgccttct
gcaaggagacctcgaccctgctccctctccggggctggatctgactccttgacggtgattcc
agacgcgagacccaaactgacggcttctagaagaggggcgagcccggccgcaagtctttcac

Fig. 8 cont.

Hybrid Rhesus box of RHD negatives

```
gtagctaagtcatcgttgcttccggcttcttaccgttctcccctttgtaaacggttacctcc
cgaaaacccaggctctcctccaacagtggttctcaagcgaggcgatcttccccgggagggga
tatttggcaaagtctgggggcattttggttcactggggctgctacttgcatccactgggta
gaggcgggggatgcagctacacaacctgcgaagcacgggacagcaccctccccaacccagac
agaattagccggcccaaaacctcagtagtgcccaggctgagaaaccctgccttaaacaaaca
acaaagaaaggccaagtcccataagtgggtcaccgcgccgagactggggtccacgggacacc
ccagccacgccaagccgggaagtccccgcctcctggagctgaacccgcccctctcccagagg
tggagctgcgggggcgggaacaggcacggagaaaataaacaagactaaaaagtcctgagta
gcgctgtgtggccgcaaacctgaacccaccttttgcaccacgcgggacccggcactcttcct
gccacccaccccctgagagggctgcgcggccgacccagtactagaaaacactcgtcacctca
ctcaagacgggtacgaaggccaacggacgccttcctttagaacgctcagcacacagagcaac
ttctcacgcctactctcaaatggcgtactccaaactagcactcccgacgtccagctgtgaac
ccagagcggcggaaagcccctgaacccagcgcccgggcatgcgcagacgcgttgttgtggtg
ggcgtggctccctccggaccggcgccccgccctccgccccgtgtccgcatgcgcgactgag
ccgggtggatggtactgctgcatccgggtgtctg
(end of Rhesus box)
gaggctgtggccgttttgttttcttggctaaaatcgggggagtgaggcgggccggcgcggc
3'
```

Fig. 9

Upstream Rhesus box of D-positives

5' ctagaaaacactttgtcattttagaggtgtta
(start of Rhesus box)
tccaatgttcgcgcaggcactggagtcagagaaaatggagttgaatcctttctctgccactc
tttgaggagaatctcaccatttattatgcactgtagaatacaacaataaaatacagccatgt
accacataacaacatcttggtaaacaacagactgcatatatgatggtggtcatccagtaagc
taaggttaatttattattattccctttttttttttctttttttttgagatgtagtcttactctg
tcacccaggctagagtgcaatggcaccatcttggctcactgcaacctctgcctcctgggttc
aagcgaatctcctgcctcagcctccgaagtagctgggaattacaggcacccaccacatctgg
ctaattttttgtatttttagtaaagatggggtttcaccatgttggccaggctgatctcaaac
tcctgacctcaagtgatctgcctgcctcggcctcccaaagtgctgggaccataggcctgagc
cactgtgcccggccttgtttgcttttttaacagttaacagtgtgctcatagaaactgctttg
acatgactgcaatcatgtgcttcatagaaacttaattagattataccactagagtcttcaga
tttttatactttttttttttgaaacggagtctcactctgtcaccaggctggagtgcagtgccg
caatctcagctcgccgcaacctccgcctcccaggttcaagtgattctcctgcctcagcctcc
cgagtagctgggattacaagtgcacactaccacgcccagctaattttttgcatttttactaga
cagggtttcaccatgttggctaggatagtttcaccaggatctcttggcctcatgatcagcct
gcctcggcctcccaaagtgctgggattacaggtgtgagccaccgtgcccagcctatacttcc
cttttgaataccatttggcgttttgaagaattaacagctttgtgaacgtggcagtgcttgt
gattcaggcttccactgagaccaaggggagaacctggttgcaggacaaacagacggacagcg
tgtggcagtgtttaaatgctcttctgaaggctgatacgacagctctctgtgcactgattgca
tacgcatcccaagattatattattgttttctattgctatgtgtcacactttgccaaacagga
tgtggaaaatgaataagcggttttcttaggcacttcttaacagacaattggtcaaaatgaac
tccattgcttaagaaacacataaacaccatttagtcactgaatatagctatatgtatggttg
ctactatggggaatcttgttttgccaattttctttgaaaattctggcagaccaaggttcttt
ttgtttacacaatacttgaaaaataaaaatgaacaagccaacaaactaccaagttttcactt
acataaatgtagttacatacagaaaatgtgactgtgaatttttttctaggacttttaaactat
aagcactatttgcacgaaagagaaccaatctatcaattacaaactcacataattttacagat
tttttttttccctacacagcacataaaacagaaggaatttgaagccaccctccaaacacaggg
gaaggaggctgtgtgtatatcctcattgtctttcacattctaaggtggttccactcagtgac
tgaaatccttaagtgttgtattagtcggcttggctaccataacagcagcttaaactgttgt
taagccactcagacttaaacaacagaaatttatttccttatagttctggaggctggaagttc
aaggtgccggcaaggctggtttctggtgagacctctctccctgtcttgcagatggctgcctc
ctccctgtgtcctcatagagcctgtcctctgcttttacacttctggtgtcatcttcctttt
tttttttttttgagacagagtctcgctctatcgcccaggctggagtgcagtggcccgatcga
tctcggctcactgcaacctctgcctcccaggttcaagcaattctcctgcctcagcctcccga
gtagctgggactacaggtgcccgccatcatgtctggctaattttgtatttttagtagagac
agggtttcaccatattggccaggctggtctccaactcctgaccttgtcatctgcctgcctcg
gcctcccaaagtgctaggattacaggcgtgagccaccgcacccggcctctttctcttcttat
aaggacaccagtcctattagattagggctccaccctcatgacctcatttgaccttaactatt
atttctttaaagcacctatttccaaatatagtcactttagggggttagggcttcaaaatatga
atctgagggagatcaattcagtaaatagcagtagtcattaacggacaatatatacaaagata
atttcgtgattactgtccttatgcataaatgtcctcagtgttccactgcctttatccagatt
tactatcacaaagactttgctctgagaaaatgtgatttctttcttttttttttttttttga
gacagagtctcactctgtcacccaggctggagtgcagtggtgcaatctcggctcactgcaat
ctccgcctcccaggttcacgccattctcttgcctcagtctcccgagtagctgggcctacagg

Fig. 9 cont.

Upstream Rhesus box of D-positives

```
cgcccgccaccctgcccagctaattttttgtattttagtagagacggggtttcaccatgtt
agccaggatggtctcaatctcctgacctcgtgatccacctgcctcagcctcccaaagtgctg
ggattacaggcatgagccaccgcgcccagcagatttttttttttttttttttttttgagat
ggagtcttgctgtgttgcccagcctggagtgcagtgttatgattttggctcactgcaacctc
tgtctaccatgttcaagcgattctcccacctctgcctcccgtgtagctgggatcacaggcac
acgccaccacacctagctacttttgtattttagtagaaatggggtttcaccatgttggcc
aggatggtcccgaactcctgacctcaagtgatcctcctgcctcggcctcccaaagtgctggg
attacaggtgtgagccactgtgcctggccaaaaatgtgatttcttatttcccacattgccaa
ttccatttcaattaactataatagctatgtctattgagcactcaagtgtattctagaaactg
ttcctgattctggggatatatccatgaatcaactatagtccctgttattaagtaatctgtag
tctgactaaaccattagaaatttaaaaaatggctactttcaaagacatcttggagttcagga
gtcccacactgcgaaccatattacctaataatccaacctgcttgtaattcacttatttaacc
aatatttattgagtgccaactttgagcctaagatacagcagtaaacaaatggataaagtccc
tgtcctcatgaaacttgtattctaatggaagaaacagaaaacaaacagatataggatgtaat
atcaggtagggataaatactttgaattcaaacaaaagtatacgtagtcagggttcgccaaag
agacacagccaatcggatacatagatatataaaagagggtttatgagttagaaagggctcac
atgattacagaggctgagaagtcccacagcagattgtctgcaagctggagacccagggatac
tggtagcatggctcagtccaagtcccaaagcctcagaatcaggaaagctgatgatataattc
ttagcccaaaggccttagaaccccagcggtgacggaaaggctgatgtaggtcctggagtcct
gagacccaacagcctgggatcctgaaatccaagggcaggaatggaagcgtgtattccagctc
caagagagtaagaccaatttgcctttcttccgttttgtttcaagccacctgcacattgagg
gcggatggttccctcttagtccattcagtcatatatcaatctcttctggaaatacccctcaca
gacacactaacaaataatgcctttccagttctctaggtattctttaatccagtcaagctgac
acctaaaattaaccatcacaaaagttaaggagaaagaagacaacttgtaggggaggctgcta
tgcaagacagtgtgtgaaggaagggctctctgaagaggttaatatctgagcagagacttgaa
tgaagtgaagaagtgagccatgtgggtatggggaatacaacttccaggtagagaagacaagt
gtggtgtgtatcagggtcagcaaagaagccatgtgacagagaagggtgggccagggagagac
ggataagtgatctaactcctgaggaggtggcctggccaggagctagagcatgaagatctcgt
aggactttattctgcaaggtgaaaagccattgtattagtctgttcacaaacccgagactagg
caatttacaaaagaaagagaggtttaatggacttacagttccacatggctggggaggcctca
caatcatggcgaaaggcaatgaggagcaagtcacgtcttacgtggatggcaggcaaagacaa
agacagcttgtgcagagaaactcccccttatagagccatcagatcctgttagacttattcac
tatcacaagaacagcacgggtaagacctgtccccatgattcagttacctcccactgggtccc
tcccacaacgcatgggaattcaggatgagatttgggtggggacacaaccaaaccctatcatt
ccacccatggcccctcccaaatttcatgtcctcacatttcaaaaccaatcacaccatcccaa
cagtccctcaaagtcttaaatgatttcagcattaactcaaaagtccacagtctaatgtctca
tctgagacaaggcaagtcctttccatttatgagcctataaaatccaaagcaagttagttact
tcctagatacaatgggggtacaggcattgggtaaatacagccattccaaatgggataaattg
gtcaaaacaaagaggctacaggcccatgagagtccaaaatccagtggggcagtcaaatctta
aagctccaaaatgatctcctttgactcaacatctcacatccaggtcacgcagatggaagggg
tgggttcccatggtcttgggcagctctgcccctgtacctttgcagggtacagcctccctctc
agctgctttcatgggctggcattgagtgtctgcagcttttccaggtacacggtgcaagctgt
cggtggatctaccattctggggtctggaggacctcttctcacagctccactaggtggtgccc
cagtagggactgtgtgtggggtctctgacccacatttcccttctgcactgccctggcagag
gatctccatgagggccctgctcctgcagcaaacttctgactgggcatccaggcatttccgca
```

Fig. 9 cont.

Upstream Rhesus box of D-positives

```
catcctctttaatctaggcgaaggtttccaaaccccaattcttgacttctgtgcactcgcag
tctcaacaccacatggaagctgtcaaggcttggggcttgcactccccgaagctacagcccaa
gctctaccttgcctcccgtcagtcatggttgggagtggctgggatgcagggcaccaagtccc
taggctgcacacagcatgaggaccccgggcctggccaacaaaaccattttttcctgatacct
ctggacctgtgatgggaggggttgccataaagacctctgacatgccctggagacattttccc
cattgtcttgggaattagcatttggctcctgttactcatgcaaattctgcagccagcttga
atttctcctcagaaaatggaattttcttttctatcacattgtcaggctgcaaattttccg
aacttttatgctctgcttcccttataaaactgaatgtctttaacagcacccaagtcacctct
tgaatgctttgctgcttagaaatttctcctgccagatactctaaatcatctctctgaagttc
aaagttctacaaatatctcgtgcaggggcaaaatgccgccagtatctttgctaaaacataac
aagagtccccttgctccagttcccaacaagttcctcatttccgtctgagaccacctcagcc
tatggactttattgtccacagtgctatcagcattttgggcaaagccattcaacaagtctcta
ggaagttccaaactttcccacatttgcctgtcttcttctgagccctccaaactgttccaaac
cctgcctgttacccagttccaaagtcacatacccattttgagtatctacggcagcacccca
ctctactggtaccaatttagccactgaagtagttggagaacagaagtaatagactctggttt
acattgtaaaagcttctctgtggctgctgtgtgaagaaaatatatgagaatgaagccccaag
atgaagcagggacacagttgcagtggttagagtaagaaatgctgctggctggcactgaagtg
atagcctggaggtttgtgtgtgcacatgcatgtatgtgttttacgatagtaggcccaaca
gatactgtaatccacacttgttttttttttgagacagagtctcacctgttgcctagacta
gaatgcagtggcacaatcttggctcactacaacctccacctcccaggttcaaacaatccttg
tgcttcagcctcccgagtagttgggattacaggtgtgtgccaccgtgcccagctatatttt
tgtatttttagcagagatgggattttgccacattggccaggctggtcttgaactcctggcct
caagcaatcctcccaccttagcctcccaaagtgctgagccaccacacctggccgcaactgat
ttttaatcatgaaatgacacatacatttaaaaaacccaatacctataatattcctggctagt
actcttcacatctatatcatcaaaaacaaagaaagtatgtgaaactgacacagccaagggga
gactaaggagacataacaattaactgtaatgtggtattctggaggggatcctggaacagaaa
aagacattaggcaaaaaactaaagaaatctgaataaaatgtggatgtcagttaataataatg
tatcatattagtccagtaattgtaacaaatataccacaataatgaaagccattaattatagg
gaaaatggaggggttaatatgggtggctggcttttgctatttctagcagctccattttatct
gcaaaagacaaacattcattaagtcccaaaaaggtaaagaatgacaaattaagcatgtatct
tattagtaagagtaatataaagatgctcactcctatttataaatatttgacaatcatgttaa
ggccacaaaagagaaaaagggtaggggcaaaaaacgcaaagagaaaggagttagtatcttt
tctcccgcactcattagctattaaagaggatgtttgtttaaagctgctcagagctggtaaa
ctaatgttaagtcactaacgggaatttaaaaggtttcattaagaactgcctgcactagattc
ctccaccctgagacattaaacaatcacgataaacctcctgagtggtaagaacttgtccattt
aaaaacaggctatagattgtatcatgcagttttatctactaatcggctaatatcccgccaaa
aacaaaaaaccccaaagggatgaaagtttcatccatcaaaggaaacaacagtcaccttggtt
cccatctcactcatatactgccgccgtacatgtcaatcagatgaacctgtgcgtatctctta
atgacaattgacccacattttgactgaagtgaaaggggttctgctccgcgaccacttcct
ggatctcccctccaccctctgtgttcttcgggtgcaccatcgggtcaaagccgcagcaac
gccgtctctgtgtgatcgcatgtgcccttctgcacacgaccttccccgagagtgaccagct
accggacaggcaccaaggagggctaccgagcacctcccggaccggcggctgcaggatcgcga
gcgcctccgctagggagactgcacgttgcgcctgtgcttcctgcggtggcgccttctgcaag
gagacctcgaccctgctccctctccgggctggatctgactccttgacggtgattccagacg
cgagacccaaactgacggcttctagaagaggggcgagcccggccgcaagtctttcacgtagc
```

Fig. 9 cont.

Upstream Rhesus box of D-positives taagtcatcgttgcttccggcttcttaccgttctcccctttgtaaacggttacctcccgaaa
acccaggctctcctccaacagtggttctcaagcgaggcgatcttccccgggaggggatattt
ggcaaagtctgggggcattttttggttcactggggctgctacttgcatccactgggtagaggc
gggggatgcagctacacaacctgcgaagcacgggacagcaccctccccaacccagacagaat
tagccggcccaaaacctcagtagtgcccaggctgagaaaccctgccttaaacaaacaacaaa
gaaaagccaagtcccataagtgggtcaccgcgccgagactggggtccacgggacacccagc
cacgccaagccgggaagtccccgcctcctggagctgaaccgcccctctcccagaggtggag
ctgcggggggcgggaacaggcacggagaaaataaacaagactaaaaagtcctgagtagcgct
gtgtggccgcaaacctgaacccaccttttgcaccacgcgggacccggcacgcttcctgccac
ccacccctgagagggctgcgcggccgacccagtactagaaaacactcgtcacctcaatcaa
gacgggtacgaaggccaacggacgccttcctttagaacgctcagcacacagagcaacttctc
acgcctactctcaaatggcgtactccaaactagcactcccgacgtccagctgtgaacccaga
gcggcggaaagcccctgaacccagcgcccgggcatgcgcagacgcgttgttgtggtgggcgt
ggctccctccggacccggcgccccgccctccgccccgtgtccgcatgcgcgactgagccgcg
ggggtggtactgctgcatccgggtgtctg
(end of Rhesus box)
aagatccgatgaaataacatatgcaaaatgattgggtccgtgattggcattccagaaatgg
3'

Figure 10

Downstream Rhesus box of D-positives aaacgctcat gacagcaaag tc
(Start of Rhesus box)
tccaatgt tcgcgcaggc actggagtca gagaaaatgg
agttgaatcc tttctctgcc actctttgag gagaatctca ccatttatta tgcactgtag
aatacaacaa taaaatacag ccatgtacca cataacaaca tcttggtaaa caacagactg
catatatgat ggtggtcatc cagtaagcta aggttaattt attattattc cttgttttt
tttttttttt tttttttttg agatgtagtc ttactctgtc acccaggcta gagtgcaatg
gcaccatctt ggctcactgc aacctctacc tcctgggttc aagcaaatct cctgcctcag
cctccaaagt agctgggatt acaggcaccc accacatctg gctaattttt tgtatttta
gtaaagatgg ggtttcacca tgttggccag gctgatctca aactcctgac ctcaagtgat
ctgcccgcct cggcctccca aagtgctgga accacaggcc tgagccactg tgcccagcct
tggttgcttt tttaacagat aacagtgtgc tcatagaaac tgctttgaca tgactgcaat
catgtgcttc atagaaactt aattagatta taccactaga gtcttcagat ttttatactt
ttttttttg aaacggagtc tcactctgtc accaggctgg agtgcagtgc cgcaatctcg
gctcactgca acctccgcct cccaggttca agcaattctc ctgcctcagc ctcccgagta
gctgggatta caagtgcgca ctaccacacc cagctaattt ttgcattttt acttgacagg
gtttcaccat gttggctagg atagtttcac caggatctct tggcctcatg atcagcctgc
ctcggcctcc caaagtgctg ggattacagg tgtgagccac cgtgcccagc ctatacttcc
cttttgaat accatttggc gttttgaaga attaacagct ttgtgaacgt ggcagtgctt
gtgattcagg cttccattga gaccaagggg agaacctggt tgcaggacaa acagacggac
agcgtgtggc agtgtttaaa tgctcttctg aaggctgata cgacagctct ctgtgcactg
attgcatacg catcccaaga ttatattatt gttttctact gctatgtgtc acactttgcc
aaacaggatg tggaaaatga ataagcggtt ttcttaggca cttcttaaca gacaattggt
caaaatgaac tccattgctt aagaaacaca taaacaccat ttagtcactg aacatagcta
tatgtatggt tgttactatg ggaaatcttg ttttgccaat tttctttgaa aattctggca
gaccaaggtt ctttttgttt acataatact tgaaaaataa aaatgaacaa gctaacaaac
taccaagttt tcacttacat aaatgtagtt gcatacagaa aatgtgactg tgaattaatt
tttctaggac ttttaaacta taagcactat ttgcacaaaa gagaaccaat ctatcaatta
caaactcaca taatttaca gatttttttt ttcctacaca gcacataaaa cagaaggaat
ttgaagccac cctccaaaca caggggaagg aggctgtgtg tatatcctca ttgtctttca
cattctaagg tggttccact cagtgactga aatccttaag cgttgtatta gtctgcttgg
gctaccataa cagcagctta aactgttgtt tagccactca gacttaaaca acagaaattt
atttccttat agttctggag gctggaagtt caaggtgccg gcaaggttgg tttctggtga
gacctctctc cctgtcttgc agatggctgc ctcctccctg tgtcctcata gagcctgtct
tctgcttta cacttctggt gtcatcttcc tttttttttt tttttttttt ttttgagaca
gagtctcgct ctatcgccca ggctggagtg cagtggcccg atcgatctcg gctcactgca
acctctgcct cccaggttca agcaattctc ctgcctcagc ctcccaagta gctgggacta
caggtgcccg ccatcatgcc tggctaattt ttgtattttt agtagagaca gggtttcacc
atattggcca ggctggtctc gaactcctga ccttgtcatc tgcctgcctc ggcctcccaa
agtgctagga ttacaggcgt gagccaccgc acccggcctc ttcctcttct tataaggaca
ccagtcctat tagattaggg ctccaccctc ataacctcat ttgaccttaa ctattatttc
tttaaagcac ctatttccaa atatagtcac tttaggggtt agggcttcaa aagatgaatc
tgagggagct caattcagta aatagcagta gtcattaatg gacaatgtat acaaagataa
tttcgtgatt actgtcctta tgcataaacg tcctcagtgt tccactgcgt ttatccagat
ttagtatcac aaagactttg ctctgagaaa aatgtgattt tttttttttt tttttttttg
agacggagtc tcgctctgtt acccaggctg gagtgcagtg gcgcgatctc ggctcactgc
aagctccgcc tcccgggttc acgccattct cctgcctcag cctccggagt agctgggact
acaggcgccc gccactacgc ccggctaact ttttgtatt tttagtagag acggggtttc
accatgttag ccaggatggt ctcaatctcc tgacctcgtg atccacctgc ctcagcctcc
caaagtgctg ggattacagg catgagccac cgcgcccagc agattttttt tttttttttt
gagatggagt cttgctctgt tgcccaacct ggagtgcagt gttatgattt tggctcactg
caacctctac catgttcaag cgattctccc acctctgcct cccgtgtagc tgggatcaca
ggcacacgcc accaccccta gctacttttt gtattttag tagaaatggg gtttcaccat
gttggccagg atggtcccga actcctgacc tcaagtgatc ctcctgcctc ggcctccaaa

Figure 10 cont.

Downstream Rhesus box of D-positives

```
gtgctgggat tacaggtgtg agccactgtg cctggccaaa aatgtgattt cttatttccc
acattgccaa ttccatttca attaactata atagctatgt ctattgagca ctcaagcgta
ttctagaaac tgttcctgat tctggggata tatccatgaa tcaactatag tccctgttat
taagtaatcc gtagtctgac taaaccatta gaaattaaaa aaaaatggct actttcaaag
acatcttgga gttcaggagt cccacactgc gaaccatatt acctaataat ccaacctgct
tgtaattcac ttatttaacc aatatttatt gagtgccaac tttgagccta agatacagca
gtaaacaaat gcataaagtc cctgtcccca tgaaacttgt attctaatgg aaaaaacaga
aaacaaacag ataggatg taatatcagg tagggataaa tactttgaat tcaaacaaaa
gtatacgtag tcagggttcc ccagagagac acagccaatc gatacataga tatataagag
agggtttatg agttagaaag ggctcacatg attacagagg ctgagaagtc ccacaacaga
ttgtctgcaa gctggagacc cagggatact ggtagcatgg ctcagtccaa gtcccaaagt
ctcagaatca ggaaagctga tgatataatt cttagcccaa aggccttaga accccagcgg
tgacggaaag gctgatgtag gtcctggcgt cctgagaccc aacagcctgg gatcctgaaa
tccaagggca ggaatggaag cgtgtattcc agctccaaga gagtaagacc aatttgcctt
tcttccgttt ttgttccaag ccaactgcac gttgagggcg gatggttccc tcttagccca
ttcagtcata tatcaatctc ttctggaaat accctcacag acacactaac aaataatgcc
tttccagttc tctaggtatt ctttaatcca gtcaagctga cacctaaaat taaccatcac
aaaagttaag gagaaagaag acaacttgta ggagaggctg ctatgcaaga cagtgtgtga
aggaagggct ctctgaagag gttaatatct gagcagagac ttgaatgaag tgaagaagtg
agccatgtgg gtatgggaa tacaacttcc aggtagagaa gacaagtgtg gtgtgtatca
cggtcagcaa agaagccatg tgacagagaa gggtgggcca gggagagacg gataagtgat
ctaactcctg aggaggtggc ctggccagga gctagagcat gaggatctcg taggattta
ttctgcaagg tgaaaagcca ttgtattagt ctgttcacaa accccagact aggcaattta
caaaagaaag agaggtttaa tggacttaca gttccacatg gctggggagg cctcacaatc
atggcgaaag gcaatgagga gcaagtcacg tcttacgtgg atggcaggca aagacaaaga
cagcttgtgc agagaaactc ccccttatag agccatcaga tcctgttaga cttatcacta
tcacgagaac agcacgggta agacctgtcc ccatgattca gttacctccc actgggtccc
tcccacaacg catgggaatt caggatgaga tttgggtggg gacacaacca aaccctatca
ttccacccat ggcccctccc aaatttcatg tcctcacatt tcaaaaccaa tcacaccatc
ccaacagtcc ctcaaagtct taaatgattt cagcattaac tcaaaagtcc acagtctaat
gtctcatctg agacaaggca agtcctttcc gtctatgagc ctataaaatc caaagcaagt
taattacttc ctagatacaa tgggggtaca ggcattgggt aaatacagcc attccaaatg
ggataaattg gtcaaaacaa agaggctaca ggcccatgag agtccaaaat ccagtggggc
agtcaaatct taaagctcca aaatgatctc ctcttgactc cacatctcac atccaggtca
tgcagatgga aggggtgggt tcccatggtc ttgggcagct ctgcccctgt acctttgcag
ggtacagcct ccctctcagc tgctttcatg ggctggcatt gagtgtctgc aactttcca
ggtacacggt gcaagctgtc ggtggatcta ccattctggg gtctggagga cctcttctca
cagctccact aggtggtgcc ccagtaggga ctgtgtgtgg ggtctctgac cccacatttc
ccttctgcac tgccctggca gaggatctcc atgagggccc tgcccctgca gcaaacttct
gcctgggcat ccaggcattt ccgcacatcc tctttaatct aggcgaaggt ttccaaaccc
cagttcttga cttctgtgca ctcgcagtct caacaccaca tggaagctgt caaggcttgg
ggcttgcact ccccgaagct acagcccaag ctctaccttg cctcctgtca gtcatggttg
ggagtggctg ggatgcaggg caccaagtcc ctaggctgca cacagcatga ggacccgggg
cctggccaac aaaaccattt tttcctgata tctctggacc tgtgatggga gggttgcca
taaagacctc tgacatgccc tggagacatt ttccccattg tcttgggaat tagcatttgg
ctcctgttac tcatgcaaat ttctgcagcc agcttgaatt tctcctcaga aaatgggaat
tttcttttc tatcacattg tcaggctgca aatttccga actttttatgc tctgcttccc
ttataaaact gaatgtcttt aacagcaccc aagtcacctc ttgaatgctt tgctgcttag
aaatttctcc tgccagatac tctaaatcat ctctctgaag ttcaaagttc tacaaatatc
tcgtgcaggg gcaaaatgcc gccagtatct ttgctaaaac ataacaagag tccccttgc
tccagttccc aacaagttcc tcatttccgt ctgagaccac ctcagcctat ggactttatt
gtccacagtg ctatcagcat tttgggcaaa gccattcaac aagtctctag gaagttccaa
actttcccac atttgcctgt cttcttctga gccctccaaa ctgttccaaa ccctgcctgt
tacccagttc caaagtcaca tacccatttt tgagtatcta cggcagcacc ccactctact
ggtaccaatt tagccactga agtagttgga gaacagaagt aatagactct ggtttacatt
```

Figure 10 cont.

Downstream Rhesus box of D-positives

```
gtaaaagctt ctctgtggct gctgtgtgaa gaaatatat gagaatgaag ccccaagatg
aagcagggac acagttgcag tggttagagt aagaaatgct gctggctggc actgaagtga
tagcctggag gtttgtgtgt gcacatgcat gtgtatgtgt tttacgatag taggcccaac
agatactgta atccacactt gtttttttt tttttttgag acagagtctc acctgttgcc
tagactagaa tgcagtggca caatcttggc tcactacaac ctccacctcc caggttcaaa
caatccttgt gcttcagcct cccgagtagt tgggattaca ggtgtgtgcc accgtgccca
gctatatttt ttgtattttt agcagagatg ggattttgcc acattggcca ggctggtctt
gaactcctgg cctcaagcaa tcctcccacc ttagcctccc aaagtgctga gccaccacac
ctggccgcaa ctgatttta atcatgaaat gacacataca tttaaaaaac caataccta
taatattcct ggctagtact cttcacatct atatcatcaa aaacaaagaa agtatgtgaa
actgacacag ccaaggggag actaaggaga cataacaatt aactgtaatg tggtattctg
gaggggatcc tggaacagaa aaagacatta ggcaaaaaac taaagaaatc tgaataaaat
gtggatgtca gttaataata atgtatcata ttagtccagt aattgtaaca aatatcccca
ataatgaaag ccattaatta tagggaaaat ggaggggtta atatgggtgg ctggcttttg
ctatttctag cagctccatt ttatctacaa aagacaaaca ttcattaagt cccaaaaagg
taaagaatga caaattaagc atgtatctta ttagtaagag taatataaag atgctcactc
atatttataa atatttgaca atgatgttaa ggccagaaaa gagaaaaaag ggtagggca
aaaaacgcaa agagaaagga gttagtatct tttctcccgc actcattagc tattaaaaga
ggatgtttgt ttaaagctgc tcagagctgg taaactaatg ttaagtcact aacgggaatt
taaaaggttt cattaagaac tgcctgcact agattcctcc accctgagac attaaacaat
cacgataaac ctcctgagtg gtaagaacgt gtccatttaa aaacaggcta tagattgtca
tgcagtttta tctactaatc ggctaatgca ccgccaaaaa caaacaaaaa aacccaaagg
gatgaaagtt tcatccatca aaggaaacaa cagtcacctt ggttcccatc ccactcatat
actgccgccg tacatgtcaa tcagatgaac ctgtgcgtat ctcttaatga caattgaccc
acctttttaa ctgaagtgaa gggggttct gctccgcgac cacttcctgg atctctccct
```

Figure 10 cont.

Downstream Rhesus box of D-positives

```
tcacctctg tgttctttcg ggtgcaccat cgggtcaaag ccgcagcaac gccgtctctg
tgtgatcgca tgtgcccttc tgcacacgac cttcccccga gagtgaccag ctaccggaca
ggcaccaagg agggctaccg agcacctccc ggaccggcgg ctgcaggatc gcgagcgcct
ccgctaggga gaccgcacgt tgcgcctgtg cttcctgcgg tggcgccttc tgcaaggaga
cctcgaccct gctccctctc cggggctgga tctgactcct tgacggtgat tccagacgcg
agacccaaac tgacggcttc tagaagaggg gcgagcccgg ccgcaagtct ttcacgtagc
taagtcatcg ttgcttccgg cttcttaccg ttctcccctt tgtaaacggt tacctcccga
aaacccaggc tctcctccaa cagtggttct caagcgaggc gatcttcccc gggaggggat
atttggcaaa gtctgggggc attttggtt cactgggct gctacttgca tccactgggt
agaggcgggg gatgcagcta cacaacctgc gaagcacggg acagcaccct ccccaaccca
gacagaatta gccggcccaa aacctcagta gtgcccaggc tgagaaaccc tgccttaaac
aaacaacaaa gaaaggccaa gtcccataag tgggtcaccg cgccgagact ggggtccacg
ggacacccca gccacgccaa gccgggaagt ccccgcctcc tggagctgaa cccgcccctc
tcccagaggt ggagctgcgg ggggcgggaa caggcacgga gaaaataaac aagactaaaa
agtcctgagt agcgctgtgt ggccgcaaac ctgaacccac cttttgcacc acgcgggacc
cggcactctt cctgccaccc accctgaga gggctgcgcg gccgacccca gtactagaaa
acactcgtca cctcactcaa gacgggtacg aaggccaacg gacgccttcc tttagaacgc
tcagcacaca gagcaacttc tcacgcctac tctcaaatgg cgtactccaa actagcactc
ccgacgtcca gctgtgaacc cagagcggcg gaaagcccct gaacccagcg cccgggcatg
cgcagacgcg ttgttgtggt gggcgtggct ccctccggac ccggcgcccc gccctccgcc
ccgtgtccgc atgcgcgact gagccgggtg gatggtactg ctgcatccgg gtgtctg
(end of Rhesus box)
gag gctgtggccg ttttgttttc ttggctaaaa tcggggagt gaggcgggcc ggcgcggc  3'
```

Fig. 11

| | | | | | |
|---|---|---|---|---|---|
|ctgatctaca|taggaattgt|tttcaagaca|tttctgcatt|cctctagtga|caggtgctc|60
|actacctcat|gagtatttca|gtgacaact|gtaatggtca|ataaagtatc|cactttccac|120
|ctccctgcag|ctcctggccc|tggctttatt|ctctgggct|ccacacattc|agtttacact|180
|cagtggccag|tggctgggac|cattgtagaa|aataaggaaa|ctccaattcc|ttccttcttt|240
|tcttcctctt|tcatctcttc|ctccctctct|acatccctct|ctctcttcct|tccttcctcg|300
|acacttacca|tgtaccagac|cttctgccag|gcacatgat|gggagcacag|gggaagttgg|360
|ctgcagggtt|agaactaagt|cccaagcccc|ctaaagctca|tgccagggga|ctgactgtc|420
|cagtactgag|ggatgggat|gctgaggctg|gtggccttcc|tcaaatgcac|tgtagtgccc|480
|caggcagagt|cctggctgc|cctgtgagga|ggtgaccaga|ggtagagcaa|cttcaccta|540
|aggctggatc|aggatcccct|ccaggttttt|actagagcca|aacccacatc|tcctttctct|600
|tctgccaccc|cccctaaaaa|tgcttagaaa|cacatagatt|taaatacaaa|ttcaaatgta|660
|agtaatttca|actgtgtaac|tatgaggagt|cagttctacg|tgggtcctat|ctgtatcctc|720
|cccagggctc|agctccattc|tttgctttca|ttcattctca|ttcaatacat|tgttgttaag|780
|agctcactgg|gtgccctctc|tgtcatgtag|taagtttta|aaaagaaagc|ctcttctgag|840
|cttcagtttc|cttattcata|aaataggagt|attgatccgt|tccttgcttt|tcttacaagg|900
|atatgctgaa|gatgactgaa|gtacagagta|agaaggatt|atgtttgggt|gtcaaaggaa|960
|tagaatgccc|tctttcaaac|tgagcacagc|aggaacctgt|aacaggaaca|cagcaacttg|1020
|ttgaatgaat|gacaatattg|gaaaacatac|atttcctccc|ctcccccatca|tagtccctct|1080
|gcttccgtgt|taactccata|gagaggccag|cacaaccagc|cttgcagcct|gagataaggc|1140
|ctttggcggg|tgtctcccct|atcgctcct|caagcccctca|agtaggtgtt|ggagagaggg|1200
|gtgatgcctg|gtgctggtgg|aaccctgca|cagagacgga|cacaggatg| |1249|

Fig. 12

```
2938  CTAGAGAGGGAAGTTTTGAAAATTAAACACTGTCTAATTTCTGCAAAGTTTTATTCATGAATTAAGAGTATTCCCTTAGTCCATTATTCCCAAGGC  RHCE
      CTAGAGAGGGAAGTTTTGAAAATTAAACACTGTCTAATTTCTGCAAAGTTTTATTCATGAATTAAGAGTATTCCCTTGTCCATTATTCCCAAGGC  Cde'
      CTAGAGAGGGAAGTTTTGAAAATTAAACACTGTCTAATTTCTGCAAAGTTTTATTCATGAATTAAGAGTATTCCCTTGTCCATTATTCCCAAGGC  RHD
                                                        |******* breakpoint region *****************************
3038  AAATATGGAAGTTTGATCATATGCTAATCATATAAAGCTGGATTCTCTTTAAGAGATTGAGAAATTAAAGGCAAAGCTGATATATCATGTTAGTTA  RHCE
      AAATATGGAAGTTTGATCATATTCTAATCATATACTAAAGCTGGATTCTCTTTAAGAGATTGAGAAATTAAAGGCAAAGCTGATATCATGTTAGTTA  Cde'
      AAATATGGAAGTTTGATCATATTCTAATCATATAACTAAAGCTGGATTCTCTTTAAGAGATTGAGAAATTAAAGGCAAAGCTGATATCATGTTAGTTA  RHD
      ****************************| ****** breakpoint region *******************
3138  TACTGTGAGTCTTATAAGAAGCTGGGAGGCAACCCCATTAACTCACCAGAATACAGAACTCAGTCTCACAACTTAAATATAATTCCTCTCAAACCTTTTC  RHCE
      TATGTGAGTCTTATAAGAAGCTGGGAGGCAACCCCATTAACTCACCAGAATACAGAACTCAGTCTCACAACTTAAATATAATTCCTCTCAAACCTTTTC  Cde'
      TATGTGAGTCTTATAAGAAGCTGGGAGGCAACCCCATTAACTCACCAGAATACAGAACTCAGTCTCACAACTTAAATATAATTCCTCTCAAACCTTTTC  RHD
3238  CTCAAAGCTTAAATTCTGAAAATAATTCTGTGAAGAGAAGAAGGCTGTCCACCAATGACTTATCTGTTATTTCTTCCTTATTGTGAGCTTAATGGC   RHCE
      CTCAAAGCTTAAATTCTGAAAATAATTCTGTGAAGAGAAGAAGGCTGTCCACCAATGACTTATCTGTTATTTCTTCCTTATTGTGAGCTTAATGGC   Cde'
      CTCAAAGATTAAATTCTGAAAATAATTCTGTGAAGAGAAGAAGGCTGTCCACCAATGGCTTATCTGTTATTTCTTCCTTATTGTGAGCTTAATGGC   RHD
3337  ATGACAAAGCAGAGGCAAAGAGGCATAACATCAATTCTTCAAAGTAGGAAGTCAAAAGGTCAGAAGCTTCCACAGCATGCAACAGCTTTGCAGATGCCCA  RHCE
      ATGACAAAGCAGAGGCAAAGAGGCATAACATCAATTCTTCAAAGTAGGAAGTCAAAAGGTCAGAAGCTTCCACAGCATGCAACAGCTTTGCAGATGCCCA  Cde'
      ATGACAAAGCAGAGGCAAAGAGGCATAACATCAATTCTTCAAAGTAGGAAGTCAAAAGGTCAGAAGCTTCCACAGCATGCAACAGCTTTGCAGATGCCCA  RHD
3437  CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA  RHCE
      CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA  Cde'
      CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA  RHD
3537  TCAGTAACAACTTGTCAAGGCCCCAGTGACCATGAAGAGTGAGGGCTGCAGCCAGGGAATAGTCCGTCGCAGAGCAAGGATTCAAATAAGCAGCCGGA  RHCE
      TCAGTAACAACTTGTCAAGGCCCCAGTGACCATGAAGAGTGAGGGCTGCAGCCAGGGAATAGTCCGTCGCAGAGCAAGGATTCAAATAAGCAGCCGGA  Cde'
      ATCAGTAACAACTTGTTCAAGGCCCCAGTGACCATGAAGAGTGAGGGCTGCAGCC-GGGAATAGTCCGTCGCAGAGCAAGGATTCAAATAAGCAGCCGGA RHD
```

Fig. 13

```
2726 TTGTATCTCTTTTTACAGCTACCTCCCCATTTCCCTCTCTATTCAAGCTAGTAACACAGTTTTCTTTCTTTAAATTCATTTATTTAAATGTAAAAATAAGTCTA    RHCE
     TTGTATCTCTTTTTACAGCTACCTCCCCATTTCCCTCTCTATTCAAGCTAGTAACACAGTTTTCTTTCTTTAAATTCATTTATTTAAATGTAAAAATAAGTCTA    Cde'
     TTGTATCTCTTTTTACAGCTACCTCCCCATTTCCCTCTCTATTCAAGCTAGTAACTCAGTTTTCTTTCTTTAAATTCAATTATTTAAATGTAAAAATAAGTCTA    RHD

2826 TTTGGAGAAAAAAATTTTGAATAGCATCTCTGGAATGCCAGTATGGCTAAATTCATGAATGTGTCCTCAAATGCTGAAATCTGGGAAGCATCTGGCCA         RHCE
     TTTGGAGAAAAAAATTTTGAATAGCATCTCTGGAAGGCCAGTATGGCTAAATTCATGAATGTGTCCTCAAATGCTGAAATCTGGGAAGCATCTGGCCA         Cde'
     TTTGGAGAAAAAAATTTT-AATAGCATCTCTGGAATGCCAGTATGGCTAAATTCATGAATGTGTCCTCAAATGCTGAAATCTGGGAAGCATCTGGCCA         RHD

2926 AGCTTTGTGTGGACAGGGCCTGCCTAGTTTGAATCCCAAGAGCCACTCATTCCAGCCACAAAACATTGGAATTCTTGGTTCACTTCCCTAACCTGAACTTGT    RHCE
     AGCTTTGTGTGGAGAGGGCCTGCCTAGTTTGAATCCCAAGAGCCACTCATTCCAGCCACAAAACATTGGAATTCTTGGTTCACTTCCCTAACCTGAACTTG     Cde'
     AGCTTTGTGTGGACAGGGCCTGCCTAGTTTGAATCCCAAGAGCCACTCATCCAGCCACAAAACATTGGAATTCTTGGTTCACTTCCCTAACCTGAACTTGC    RHD

********** breakpoint region **********

3026 CCTCTGTGAATAGGGACATAATAGCTCACTCACAGGGCTGCTGTGAGGACATGTTGAGCTGAGCTGTTGAGGGTCTCGCCAGGGGAGACCCTGTGCAGGAGAC    RHCE
     CCTCTGTGAATAGGGACATAATAGCTCACTCACAGGGCTGCTGTGAGGACATGTTGAGCTGAGCTGTTGAGGGTCTGTCAGGGGAGACCCTGTGCAGGAGAC    Cde'
     CCTCTGTGAATAGGGACATAATAGCTCACTCACAGGGCTGCTGTGAGGACATGTTGAGCTGAGCTGTTGAGGGTCTGTCAGGGGAGACCCTGTGCAGGAGAC    RHD

********** breakpoint region **********

3126 TGTTATCATGGTGATGGATTTCTGCTTCATTCTTTTCTGCTTCATTCTTTTTCCAGACAGCAGCATCATATAGAATGAGTTGTGGGTGGCAGTCAGCAGTTTGGGTTTATC    RHCE
     TGTTATCATGGTGATGGATTTCTGCTTCATTCTTTTCTGCTTCATTCTTTTTCCAGACAGCAGCATCATATAGAATGAGTTGTGGGTGGCAGTCAGCAGTTTGGGTTTATC    Cde'
     TGTTATCATGGTGATGGATTTCTGCTTCATTCTTTTCTGCTTCATTCTTTTTCCAGACAGCAGCATCATATAGAATGAGTTGTGGGTGGCAGTCAGCAGTTTGGGTTTATC    RHD

********** breakpoint region **********

3226 CTCTATTCTGCCACTTATTACTTAAAAAAA------AAAACCCAACTTATATAGTATAAGCTATATCCAGAAAAGTGCAAATATCATACAAGTACCATTT    RHCE
     CTCTATTCTGCCACTTATTACTTAAAAAAATCCAAAAAAACCCAACTTATATAGTATAAGCTATATCCAGAAAAGTGCAAATATCATACAAGTACCATTT    Cde'
     CTCTATTCTGCCACTTATTACTTAAAAAAACCCAAAAAACCCAACTTATATAGTATAAGCTATATCCAGAAAAGTGCAAATATCATACAAGTACCATTT    RHD
```

Fig. 13 cont.

```
              ************************** breakpoint region ************************
3320 GATGAATCTTCTGATATCCCACATAACCAACACCCACATAACCAACACCACTAACCTGACTTCTAACAGCATCAGTCAGTT  RHCE
     GATGAATCTTCTGATATCCCACATAACCAACACACCAACACCCAGAATAACCACTAACCTGACTTCTAACAGCATCAGTCAGTT  Cde'
     GATGAATCTTCTGATATCCCACATAACCAACACACCAACACCCAGAATAACCACTAACCTGACTTCTAACAGCATCAGTCAGTT  RHD

********************* breakpoint region *******************************
3420 TTGTCTGTTTTTGTACATTATATATGTGATGGTTTGAATGTGTCCCCCAAATTTCATGTGCTAGAAACTTAATCCTTCAATTCATATGTTGATGCTATTT  RHCE
     TTGTCTGTTTTTGTACATTATATATGTGATGGTTTGAATGTGTCCCCCAAATTTCATGTGCTGGAAACTTAATCCTTCAATTCATATGTTGATGCTTTTT  Cde'
     TTGTCTGTTTTTGTACATTATATATGTGATGGTTTGAATGTGTCCCCCAAATTTCATGTGCTGGAAACTTAATCCTTCAATTCATATGTTGATGTTTTT  RHD

***************** breakpoint region ***************************
3520 GGAGGAAGGGCCTTTGGGAAGTAATTAGGATTAGATTAGGATAAGGTCATGGGGTGAGGTATGATGGCACTGGTGACTGGTATAAGAAGAGAAAGAGAAATCTGAGCT  RHCE
     GGAGGAAGGGCCTTTGGGAAGTAATTAGGATTAGATTAGGATAAGGTCATGGGGTGAGGTATGATGGCACTGGTGACTGGTATAAGAAGAGAAAGAGAAATCTGAGCT  Cde'
     GGAGGAAGGGCCTTTGGGAAGTAATTAGGATTAGATTAGGATAAGGTCATGGGGTGAGGTATGATGGCACTGGTGACTGGTATAAGAAGAGAAAGAGAAATCTGAGCT  RHD

* breakpoint region *|
3620 GGCATGCTCTTGCCCTCCACCGTGTGATGACTTCTCCATGTCATGATGCAGCAGCAAGAAGGCCCTCACCAGATGGTGGCACCATGCTTTGGACTTCCCAG  RHCE
     GGCATGCTCTTGCCCTCTCACTGTGTGATGACTTCTCCATGTCATGATGCAGCAGCAAGAAGGCCCTCACCAGATGGTGGCACCATGCTTTGGACTTCCCAG  Cde'
     GGCATGCTCTTGCCCTCTCACTGTGTGATGACTTCTCCATGTCATGATGCAGCAAGAAGGCCCTCACCAGATGGTGGCACCATGCTTTGGACTTCCCAG  RHD
```

MOLECULAR STRUCTURE OF RHD NEGATIVE

CROSS REFERENCE TO RELATED APPLICATIONS

This application is a divisional application of U.S. application Ser. No. 10/129,580, filed May 2, 2002, which is a 371 national phase application of PCT/EP00/10745, filed Oct. 31, 2000, which claims priority to foreign application nos. DE 00 11 1696.1, filed May 31, 2000 and DE 99 12 1686.2, filed Nov. 11, 1999 all of which are incorporated by reference herein in their entirety.

The present invention relates to a nucleic acid molecular structure representing the Rhesus genes locus comprising the RHD, SMP1 and RHCE genes and/or the Rhesus box(es), preferably the hybrid Rhesus box, the upstream Rhesus box and/or the downstream Rhesus box. Furthermore, the invention relates to a process for the specific detection of the common RHD negative haplotypes. The invention further relates to the detection of RHD positive haplotypes in D-negative individuals. Various mutations in the RHD gene have been identified that allow for the development of diagnostic tools. The invention also relates to oligonucleotides, that specifically hybridize to the hybrid box, preferably the breakpoint or breakpoint region or to the upstream and downstream Rhesus boxes. Additionally, the invention relates to kits comprising or employing the above recited compounds of the invention.

Several documents are cited throughout the text of this specification; the disclosure content of each of the documents cited herein (including any manufacturer's specifications, instructions, etc.) is hereby incorporated by reference.

The Rhesus D antigen (ISBT 004.001; RH1) is the most important blood group antigen determined by a protein. Anti-D remains the leading cause of hemolytic disease of the newborn (Filbey, Acta Obstet Gynecol Scand, 74:687, 1995; Bowman, J, Semin Perinatol 21:39, 1997). Depending on the population, 3% to 25% of whites lack the antigen D (Mourant, The distribution of the human blood groups and other polymorphisms, London, Oxford University Press, 1976). Anti-D immunizations can occur readily in O-negative recipients (Urbaniak, Transfusion 21:64, 1981).

The antigens of the RH blood group are carried by proteins coded by two genes, RHD and RHCE, that are located at chromosomal position 1p34.1-1p36 (Cherif-Zahar, Hum. Genet. 86: 398, 1991; MacGeoch, Cytogenet. Cell Genet. 59:261, 1992) probably within less than a 450,000 base pair (bp) distance (Carritt, Hum. Mol. Genet. 6:843, 1997). Both genes encompass ten exons and their structures are highly homologous. The relative orientation of the genes, their distance, and the possibility of interspersed other genes were unknown (Flegel, Transfus. Med. 8:281, 1998). Very recently, Okuda at al. (Okuda, Biochem. Biophys. Res. Commun. 263: 378, 1999) reported a sequence of about 11,000 bp, which was thought to represent the DNA segment between RHD and RHCE.

In whites, the vast majority of D-negative haplotypes is due to a deletion of the RHD gene: This deletion spans the whole RHD gene, because RHD-specific sequences ranging from exon 1 to the 3' untranslated region are absent (Gassner, Transfusion 37:1020, 1997). The exact extent of the deletion was uncertain, leaving open the possibility that neighboring genes were also affected.

The identification of the RHD gene as the molecular basis of the D antigen allowed RhD phenotype prediction by DNA typing (Flegel, Transfus. Med. 8:281, 1998; Lo, Lancet 341: 1147, 1993). However, since the structure of the prevalent D-negative haplotype is unknown, a specific detection of the RHD deletion remained impossible and the discrimination of $RHD^+/RHD^+$ homozygous from $RHD^+/RHD^-$ heterozygous individuals relied on indirect methods. This discrimination is of clinical interest in particular, because in D-negative mothers with an anti-D, the risk of an affected child is 100% with a $RHD^+/RHD^+$ father, but only 50% with a $RHD^+/RHD^-$ father.

Several indirect approaches have been applied to determine the zygosity: (i) a simple guess based on the phenotype is correct in about 95% of cases, (ii) determination of the D antigen density which can be confounded by factors such as the presence of the C antigen, and (iii) several methods involving the parallel quantitative amplification of RHD- and RHCE-specific sequences (Cossu, Electrophoresis 17:1911, 1996; Döscher, Infusionsther. Transfusionsmed. 26 (suppl 1):31, 1999 (abstr.)). These elaborate techniques may not be practical in routine laboratories. In addition, several investigators identified polymorphisms in the RHCE gene or neighboring sequences genetically linked to the lack of the RHD gene (Carritt, Hum. Mol. Genet. 6:843, 1997; Huang, Am. J. Hum. genet. 58: 133, 1996; Fujiwara, Hum. genet. 104:301, 1999; Onda, Gene 159:225, 1995). This indirect approach relied on the linkage disequilibrium associating the RHD deletion with a polymorphism.

Furthermore, the utility of the RHD PCR is limited by the incomplete knowledge of presumably rare RHD positive alleles in RhD-negative. RHD positive alleles in RhD negative are caused by RHD-CE-D hybrid genes (Huang, Blood 88:2326-33, 1996; Faas, Transfusion 37:38-44, 1997, Faas, Transfusion 36:506-11, 1996), nonsense-mutations (Avent, Blood 89:2568-77, 1997), frameshifts (Andrews, Blood 92:1839-40, 1998; Cherif-Zahar Br. J. Haematol. 102:1263-70, 1998), or pseudogenes (Singleton, Blood 95:12-8, 2000). Such alleles are frequent in Africans (Faas, Transfusion 37:38-44, 1997, Singleton, Blood 95:12-18, 2000) and Asians (Okuda, J. Clin. Invest. 100:373-9, 1997) but rare in whites. Nevertheless, recent analyses (Avent, Blood 89:2568-77, 1997; Flegel, Transfus. Med. 8:281-302, 1998) suggested that even for whites these alleles are likely the leading cause of incorrect Rh phenotype prediction. Several observations in whites (Avent, Blood 89:2568-77, 1997; Hyland, Blood 84:321-4, 1994) indicated that these alleles clustered in the Cde and cdE haplotypes.

The most direct approach for analyzing the RHD locus on the molecular level would be PCR amplification spanning the RHD deletion site. Such an assay has, so far, not been available because the structure of the RHD locus in RhD positives and RhD negatives was incompletely understood.

Accordingly, the technical problem underlying the present invention was to provide means and methods for a reliable, nucleic acid based analysis of the Rhesus D locus. These means and methods should be, inter alia, suitable for the detection and/or discrimination of $RHD^+/RHD^+$ and $RHD^+/RHD^-$ individuals.

The solution to said technical problem is achieved by providing the embodiments characterized in the claims.

Thus, the invention relates to a nucleic acid molecular structure representing the Rhesus genes locus comprising the RHD, SMP1, and RHCE genes and/or the Rhesus boxes, preferably the hybrid Rhesus box, the upstream Rhesus box and/or the downstream Rhesus box, the sequences of which are shown in FIGS. 8 to 10.

(SEQ ID NOS 18-20)

In the context of the present invention, the term "nucleic acid molecular structure" is defined as a linear DNA-segment that comprises, in its broadest meaning, the combination of the above mentioned genes, namely the RHD, SMP1 and RHCE genes, arranged in this 5' to 3' order and/or Rhesus boxes that co-determine said Rhesus gene locus. DNA sequences that give rise to the molecular structure of the invention include the following: The nucleotide sequence structure consists of a Rhesus box 5' flanking region, the hybrid Rhesus box or two Rhesus boxes with intervening RHD gene, and the Rhesus box 3' flanking region.

The following sequences represent preferred embodiments contained in the nucleic acid molecular structure of the invention.

The Rhesus box 5' flanking region is represented in the genomic clone HS465N24 (GenBank accession number AL031432.1), bases 1 to 120,156.

The hybrid Rhesus box is represented in GenBank accession number AL252313 bases 33 to 9,180.

The two Rhesus boxes with intervening RHD gene consists of the upstream Rhesus box, represented in GenBank accession number AL252311 bases 34 to 9,175, the RHD gene and the downstream Rhesus box represented in GenBank accession number AL252312 bases 23 to 9,177 (see FIGS. 8 to 10) (SEQ ID NOS 18-20).

The Rhesus box 3' flanking region consists of a small DNA segment between the downstream or hybrid Rhesus box and the SMP1 gene, the SMP1 gene and the RHCE gene.

The RHD gene consists of a RHD 5' region homologous to genomic clone HS469D22 (GenBank accession number AL031284.9) bases 56,012 to 51,472; also represented by a nucleotide segment dubbed "stuffer fragment" (GenBank accession number AB029152) bases 7,716 to 11,005; the RHD promoter (GenBank accession number AJ252314) bases 1 to 1,246 (see FIG. 11) (SEQ ID NOS 18-20) and the RHD gene defined by the RHD cDNA (GenBank accession number X63097) bases 1 to 1,371 and by its intron sequences.

The small DNA segment preferably comprises 15 nucleotides between the downstream or hybrid Rhesus box and the SMP1 gene and is represented in AL252312 by bases 9,178 to 9,192.

The SMP1 gene is defined by the SMP1 cDNA represented in GenBank accession number AF0811282 and by its intron sequences.

The RHCE gene is defined by the RHCE cDNA represented in GenBank accession number X63095 and by its intron sequences and further represented in part by the genomic clone HS469D22 (GenBank accession number AL031432.1) bases 1 to 51,471 and the RHCE 5' flanking region represented by genomic clone HS469D22 bases 51,472 to 84,811.

Whereas the upstream Rhesus box is located 5' of the RHD gene, the downstream Rhesus box is located between the RHD and SMP1 genes in this structure of the present invention. Alternatively, the term "nucleic acid molecular structure" relates to DNA segments solely comprising the referenced Rhesus boxes. This term, in a further alternative, relates to DNA segments comprising the RHD, SMP1 and RHCE genes and two Rhesus boxes, namely the upstream Rhesus box and the downstream RHD box. Comprised by this term are also, in a further alternative, DNA segments that comprise the hybrid Rhesus box, the SMP1 gene and the RHCE gene. In another alternative, the term relates to DNA segments comprising the SMP1 gene and the hybrid Rhesus box. This term in a further alternative relates to DNA segments comprising the upstream Rhesus box, RHD, downstream Rhesus box and SMP1.

This term in another alternative relates to DNA segments comprising the downstream Rhesus box and SMP1. For a better understanding of the claimed subject-matter, it is referred to FIGS. 1 and 7, infra.

In accordance with the present invention, the term "nucleic acid molecular structure" comprises also any feasible derivative of the above referenced nucleic acid structure to which a nucleic acid probe may hybridize. In other words, the structure of the invention may be prepared by synthetic or semi-synthetic means and thus consist of or comprise peptide nucleic acid. Said term also bears the meaning of a nucleic acid molecule.

In accordance with the present invention, the term "Rhesus box" describes upstream and downstream DNA segments that flank the RHD gene on the 5' and 3' end. The three Rhesus boxes are defined by their nucleotide sequences. The hybrid Rhesus box is represented in one embodiment in GenBank accession number AL252313 bases 33 to 9,180. The two Rhesus boxes with intervening RHD gene consists of the upstream Rhesus box, represented in one embodiment in GenBank accession number AL252311 bases 34 to 9,175 and the downstream Rhesus box represented in one embodiment in GenBank accession number AL252312 bases 23 to 9,177. As exemplified in the appended examples the Rhesus boxes are preferably approximately 9000 bp long, having 98.6% identity and identical orientation. According to the present invention the upstream and downstream Rhesus boxes are at least 95% homologous. The length of these Rhesus boxes may vary. It is expected that the length of these Rhesus boxes may vary, because, among other structural features, multiple repetitive elements, some of them are organized in tandem arrays, are known to be prone to (array) elongation and deletion events. If such events occur the length of the Rhesus boxes may shrink to less than 1,000 nucleotides length or extend to more than 20,000 nucleotides length.

In accordance with the present invention the term 'identity' refers to the determination of sequence identity using suitable alignment programs, such as BLAST.

As has been pointed out above, the diagnostic analysis of RHD negatives on the molecular level has so far been hampered by the fact, that the overall structure of the RHD/RHCE loci was unknown. It has now been surprisingly found, that the two genes, RHD and RHCE, have opposite orientation and face each other with their 3' ends. In accordance with the present invention it has further been found that the RHD gene is surrounded by two highly homologous Rhesus boxes. The physical distance between RHD and RHCE is about 30,000 bp and is filled with a Rhesus box and the SMP1 gene. The breakpoints of the RHD deletion in the prevalent RHD negative haplotypes are located in the 1,463 bp identity region of the Rhesus boxes. Similar RHD deletion events may involve any other region within the highly homologous Rhesus boxes. Hence, a region of a breakpoint comprising an RHD deletion other than the common RHD deletion may be anticipated to occur anywhere within the Rhesus boxes as defined above.

The opposite orientation of the two RH genes explains the different character of hybrid genes in the MNS and RH blood group: The glycophorin genes encoding the MNS antigens occur in the same orientation (Onda, Gene 159:225, 1995), and many recombinations may be explained as unequal crossing over resulting in single hybrid genes (Blumenfeld, Hum. Mutat. 6:1999, 1995). Based on the surprising findings referred to above, the events on the molecular level that lead to RHD negatives can now be more fully understood. In the RH locus, the inversely oriented sequences are unlikely to trigger unequal crossing over, and if this event occurred, no functional hybrid gene would result. The conclusion that unequal crossing over at the RH gene locus is unlikely may explain that most RH hybrid genes are of RHD-CE-D or RHCE-D-CE type and involve stretches of homologous DNA positioned in cis as noted previously (Wagner, Blood 91:2157, 1998). Currently, the RH gene system is the only well investigated gene locus where the two genes have opposite orientation, rendering it a model system for the evolution of neighboring, oppositely oriented genes that are frequent throughout genomes.

Figure 4:
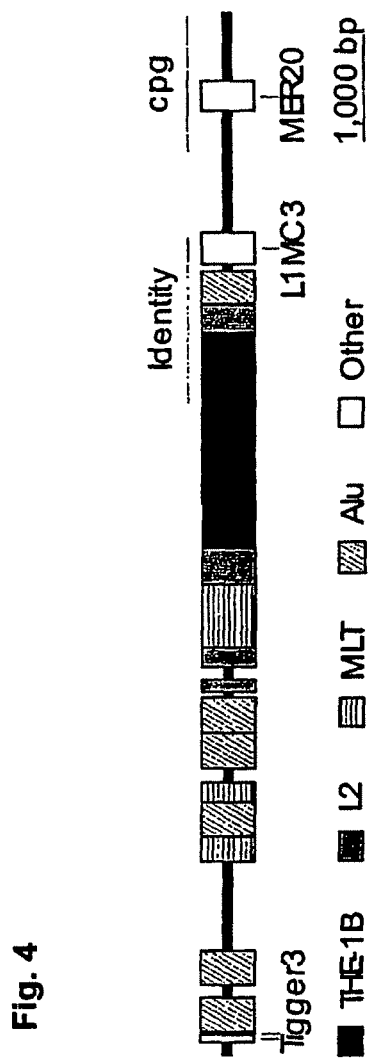
Figure 7:
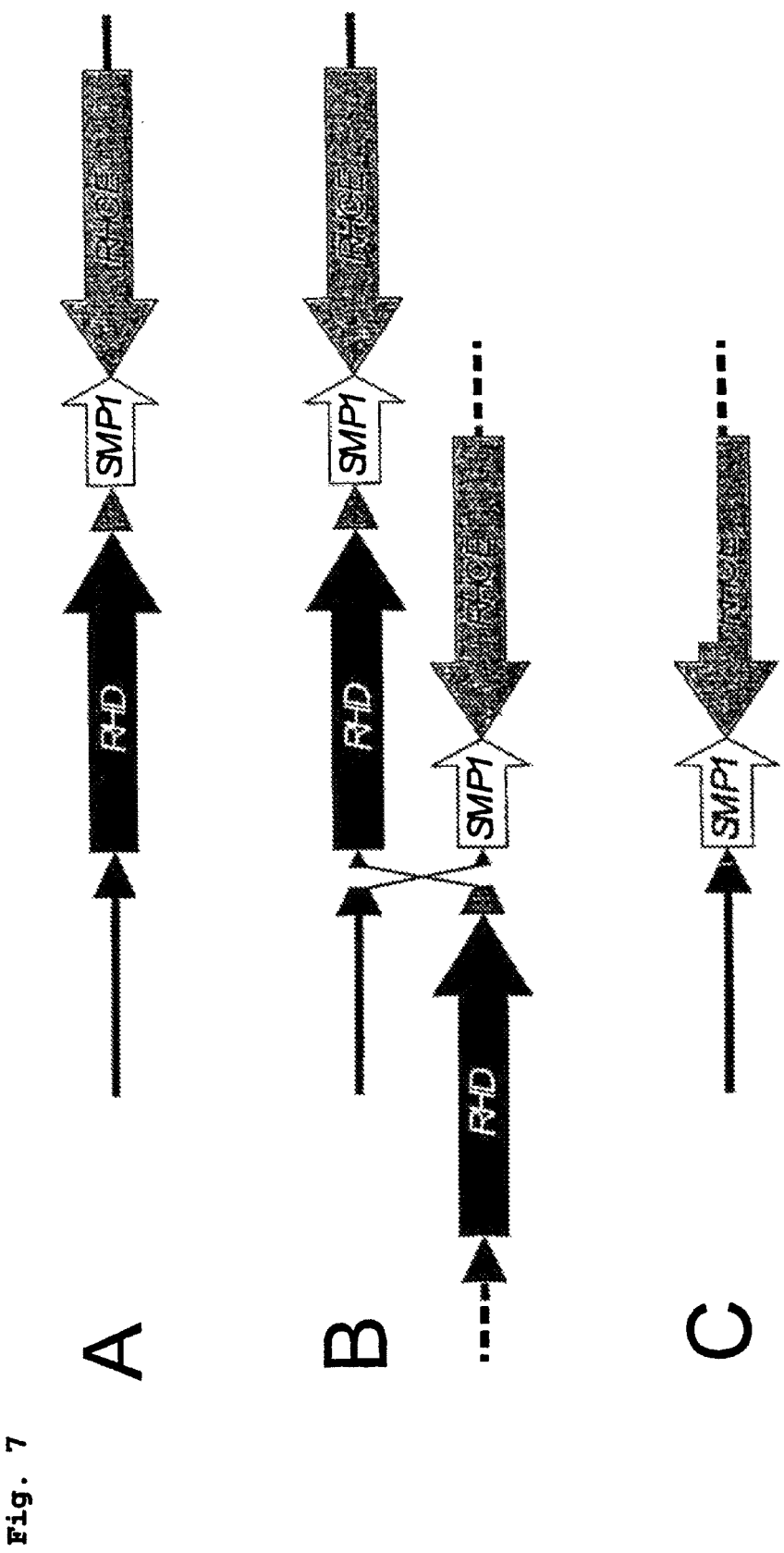

Based on the structure of the RH gene locus (FIG. 1), a parsimonious model for the RHD gene deletion event is proposed (FIG. 7). Although the applicant does not wish to be bound to theory, the following is believed with regard to the generation of RhD negative. The RHD deletion may be explained by unequal crossing over triggered by the highly homologous Rhesus boxes embracing the RHD gene. The hybrid-type Rhesus box of RHD-negatives arises, when a crossover leading to a deletion event involving a breakpoint region within the identity region of the upstream and downstream Rhesus boxes takes place. Thus, the hybrid RHD box is characterized by a 5' portion derived from the upstream RHD box fused to a 3' portion from the downstream RHD box. In one preferred embodiment the breakpoint region is 903 bp long. The sequence of this preferred hybrid Rhesus box is depicted in FIG. 5 (SEQ ID NO 15). In the specific embodiments described in the examples, said 903 bp breakpoint region in the Rhesus boxes is located in a 1,463 bp stretch of 99.9% homology resembling a THE-1B human transposable element and a L2 repetitive DNA element (FIG. 4). Interestingly, the >60,000 bp DNA segment that is deleted in the RHD negative haplotype consisted only of and contained all sequences that are duplicated in the RHD positive haplotype.

The findings of the present invention referred to herein above allow for the establishment of a number of easy to do or refined methods for the analysis of the genotype of an individual with regard to the RH gene locus. Examples of such methods are provided herein below.

While the molecular mechanism resulting in the prevalent RHD negative haplotype is now apparent, it is less clear how the much older duplication event gave rise to the structure of the RH genes in RHD positives. The duplication of the Rhesus box and the RH genes probably occurred as a single event, because the overall homology of the two Rhesus boxes is very similar to that of the RH genes. Without being bound by theory, it is tempting to speculate that the RHD duplication originate in causal connection with the insertion of the near full-length THE-1B transposon-like human element in duplicate. However, the open reading frame of the THE-1B element probably was non-functional at the time of the duplication.

In a preferred embodiment of the present invention, said nucleic acid molecular structure is representative of the common RHD negative haplotypes.

According to the present invention, the term "is representative of" relates to a nucleic acid molecular structure comprising all sequential and structural features to relate said structure to a group of molecular structures sharing said features. In the above preferred embodiment, said features give rise to the common RHD negative haplotype. In the present context this means preferably the deletion of the RHD gene encompassing the whole RHD gene and its 5' region, which are located between the upstream Rhesus box and the downstream Rhesus box.

In the present context this could also mean, for example, that all structures sharing a nonsense mutation, missense mutation, splice site mutation, partial deletion, partial insertion, partial inversion or a combination thereof within the RHD gene, which terminates or obliterates the expression of a protein product of the RHD gene, are representative of the RHD negative haplotype.

The term "haplotype" relates to a series of linked alleles within a defined region on a single maternal or paternal chromosome.

The term "common RHD negative haplotype" refers to any RhD antigen negative haplotype that comprises a hybrid Rhesus box. Preferably the DNA segment encompassing the whole RHD gene and its 5' region, which are located between the upstream Rhesus box and the downstream Rhesus box, is deleted.

In another embodiment, the invention relates to a nucleic acid molecular structure, dubbed Rhesus box, which is flanking the breakpoint region of the RHD deletion in the common RHD negative haplotypes.

In accordance with the present invention the term "breakpoint region of the RHD deletion" describes a distinct DNA segment that is involved in an RHD deletion. As has been pointed out above, said deletion may be the result of an unequal crossing over event involving both the upstream and downstream Rhesus boxes, deleting interspersed sequences and finally giving rise to a nucleic acid molecular structure (the referenced Rhesus boxes for a better delimitation from the upstream and downstream Rhesus box also referred to as hybrid Rhesus box) wherein the 5' portion of the upstream RHD box is in close spatial proximity to the 3' portion of the downstream RHD box. As mentioned above and depicted in FIGS. 7 and 4 this region can preferably be 903 bp long and be located in a 1,463 bp stretch within the Rhesus boxes, having 99.9% homology in this segment. In another preferred alternative said region is located downstream from said 903 bp fragment but is still contained within the 1463 bp stretch. Preferably, said fragment is 556 to 560 bp long. The actual breakpoint may vary such that the contribution of the upstream Rhesus box and the downstream Rhesus box are different in different individuals. However, in accordance with the present invention, the breakpoint in any case occurs in the upstream and downstream Rhesus boxes.

The hybrid Rhesus box is particularly useful for the analysis of RHD-negative haplotypes. For example, oligonucleotides may be employed that hybridize to nucleic acid sequences comprising the breakpoint which arose as a result of the RHD deletion. It is to be understood that such oligonucleotides need to hybridize to a significant portion preferably encompassing 20 nucleotides, that is located 5' and 3' of the region of the actual breakpoint in order to be indicative of a deletion event. For example, when such an oligonucleotide is hybridized under stringent conditions such as 0.2×SSC, 0.1 SDS at 65° C. and the probe would be 943 nucleotides long, then the hybridizing region should include portions that hybridize 3' as well as 5' of the breakpoint.

For example, a Rhesus box or a part thereof encompassing the region of the breakpoint is amplified. Thereafter the amplification product is assayed in a sequence specific way by hybridization to an oligonucleotide of about six or more nucleotides length.

Preferably, a stretch of DNA representative of a Rhesus box or part thereof encompassing the region of the breakpoint is amplified using two primers. One primer may be located in the Rhesus box 5' of the identity region and is specific for both the upstream Rhesus box and the hybrid Rhesus box. The other primer may be located in the Rhesus box 3' of the identity region and is specific for both the downstream Rhesus box and the hybrid Rhesus box, in this application, the presence of an amplification product of the expected size is indicative of the presence of a hybrid Rhesus box and hence, of the RHD deletion.

Another possible combination of primers is the following: One primer may be located in the Rhesus box 5' of the identity region and is specific for both the upstream Rhesus box and the hybrid Rhesus box. The other primer may be located in the Rhesus box 3' of the identity region. In this application, the presence of a hybrid Rhesus box is determined by examining the specificity of the parts of the amplification product pertaining to a DNA stretch of the Rhesus box 3' of the identity region. This may for example be effected by hybridization with an oligonucleotide that hybridizes to the hybrid Rhesus box and to the downstream Rhesus box but not to the upstream Rhesus box, or by digestion with a restriction enzyme that cuts the hybrid Rhesus box and the downstream Rhesus box but does not cut the upstream Rhesus box, or by digestion with a restriction enzyme that does not cut the hybrid Rhesus box and the downstream Rhesus box but cuts the upstream Rhesus box, or by nucleotide sequencing.

Another possible combination of primers is the following: One primer may be located in the Rhesus box 5' of the identity region. The other primer may be located in the Rhesus box 3' of the identity region and is specific for both the downstream Rhesus box and the hybrid Rhesus box. In this application, the presence of a hybrid Rhesus box is determined by examining the specificity of the parts of the amplification product pertaining to a DNA stretch of the Rhesus box 5' of the identity region. This may for example be effected by hybridization with a nucleotide that hybridizes to the hybrid Rhesus box and to the upstream Rhesus box but not to the downstream Rhesus box, or by digestion with a restriction enzyme that cuts the hybrid Rhesus box and the upstream Rhesus box but does not cut the downstream Rhesus box, or by digestion with a restriction enzyme that does not cut the hybrid Rhesus box and the upstream Rhesus box but cuts the downstream Rhesus box, or by nucleotide sequencing.

The hybrid Rhesus box may also serve as a diagnostic tool for the presence of the RHD deletion when analyzed by an anti-DNA antibody specific for one or more embodiments of the hybrid box, a fragment or derivative thereof such as an scFvFab or F(ab')$_2$ fragment or an aptamer etc. Thus, antibodies, fragments or derivatives thereof or such aptamers can be generated by the person skilled in the art according to conventional technology (see, for example, Harlow and Lane, "Antibodies, A Laboratory Manual", CSH Press 1988, Cold Spring Harbor).

In a preferred embodiment, the invention relates to a nucleic acid molecular structure representative of an RHD negative haplotype comprising an RHD gene deletion involving the upstream Rhesus box, the downstream Rhesus box, or both.

The invention further relates to a nucleic acid molecular structure that is flanking the Rhesus box in the common RHD negative haplotypes. These structures or sequences can be used to derive primers for amplification reactions such as long range PCR for the molecular analysis of the RHD locus.

For example, a stretch of DNA representative of a Rhesus box and parts of their flanking regions or parts thereof encompassing the region of the breakpoint is amplified using two primers. One primer may be located in the 5' flanking region of the Rhesus box. Alternatively, this primer may be located in the Rhesus box 5' of the identity region and is specific for both the upstream Rhesus box and the hybrid Rhesus box. The other primer may be located in the Rhesus box 3' flanking region. Alternatively, this primer may be located in the Rhesus box 3' of the identity region and is specific for both the downstream Rhesus box and the hybrid Rhesus box. In this application the presence of an amplification product of the expected size is indicative of the presence of a hybrid Rhesus box and hence, of the RHD deletion.

Another possible combination of primers is the following: One primer may be located in the 5' flanking region of the Rhesus box. The other primer may be located in the Rhesus box 3' of the identity region. In this application, the presence of a hybrid Rhesus box is determined by examining the specificity of the parts of the amplification product pertaining to a DNA stretch of the Rhesus box 3' of the identity region. This may for example be effected by hybridization with an oligonucleotide that hybridizes to the hybrid Rhesus box and to the downstream Rhesus box but not to the upstream Rhesus box, or by digestion with an restriction enzyme that cuts the hybrid Rhesus box and the downstream Rhesus box but does not cut the upstream Rhesus box, or by digestion with a restriction enzyme that does not cut the hybrid Rhesus box and the downstream Rhesus box but cuts the upstream Rhesus box, or by nucleotide sequencing.

Another possible combination of primers is the following: One primer may be located in the Rhesus box 5' of the identity region. The other primer may be located in the 3' flanking region of the Rhesus box. In this application, the presence of a hybrid Rhesus box is determined by examining the specificity of the parts of the amplification product pertaining to a DNA stretch of the Rhesus box 5' of the identity region. This may for example be effected by hybridization with an oligonucleotide that hybridizes to the hybrid Rhesus box and to the upstream Rhesus box but not to the downstream Rhesus box, or by digestion with an restriction enzyme that cuts the hybrid Rhesus box and the upstream Rhesus box but does not cut the downstream Rhesus box, or by digestion with a restriction enzyme that does not cut the hybrid Rhesus box and the upstream Rhesus box but cuts the downstream Rhesus box, or by nucleotide sequencing.

In a preferred embodiment the nucleic acid molecular structure is representative of RHD positive haplotypes.

The term "RHD positive haplotype" refers to any haplotype that comprises DNA sequences specific for the RHD gene.

In a preferred embodiment the invention relates to a nucleic acid molecular structure representative of the common RHD positive haplotype.

In another preferred embodiment the nucleic acid molecular structure is derived from a sample comprising an RHD positive haplotype that is serologically classified RhD negative.

In the context of the invention, the term 'serologically classified RhD negative' describes a sample that has been tested for the presence of RhD antigen using, e.g., routine serological assays wherein the result of such assays was negative.

In a particularly preferred embodiment the sample that is classified RhD negative is obtained from a Caucasian population.

In another more preferred embodiment the nucleic acid molecular structure comprises a partial RHD deletion.

One alternative for explaining that an allele routinely diagnosed RHD positive gives rise to a RhD-negative phenotype is the deletion of a part of the RHD gene or the substitution of a part of the RHD gene by the corresponding DNA segments derived from the RHCE gene not detected by standard diagnostic methods such as PCR.

In a preferred embodiment said deletions or substitutions comprise RHD exons 3 to 7 or 4 to 7 giving rise to a CcddEe phenotype, or 1 to 9.

In a most preferred embodiment said substitution comprises a RHD-CE(3-7)-D hybrid gene, a RHD-CE(4-7)-D hybrid gene giving rise to a CcddEe phenotpye or a RHCE (1-9)-D(10) hybrid gene, all of which correlate with a RhD negative phenotype.

In another most preferred embodiment the nucleic acid molecular structure of the present invention comprising an RHD-CE-D hybrid allele, which is representative of a Cde$^s$ haplotype but also occurs in other Rhesus haplotypes, carrying a 5' breakpoint region located in intron 3, the sequence of which breakpoint region is shown in FIG. 12 (SEQ ID NOS 22-24), and/or a 5' breakpoint region located in intron 7, the sequence of which breakpoint region is shown in FIG. 13 (SEQ ID NOS 25-27), or both breakpoint regions. Cde$^s$, also known as r$^{ts}$, is a RH haplotype resembling Cde that was initially characterized as expressing antigen e$^s$ instead of antigen e, expressing antigen c, and expressing reduced and altered antigen C (Issitt, P. D. *Applied Blood Group Serology*, Miami: Montgomery Scientific Publications, 1985, page 239). The molecular structure underlying this haplotype has recently been elucidated (Blunt, T., Daniels, G., and Carritt, B. Serotype switching in a partially deleted RHD gene. *Vox Sang.* 67:397-401, 1994; Faas, B. H. W., Becker, E. A. M., Wildoer, P., Ligthart, P. C., Overbeeke, M. A. M., Zondervan, H. A., von dem Borne, A. E. G. K., and van der Schoot, C. E. Molecular background of VS and weak C expression in blacks. *Transfusion* 37:38-44, 1997; Daniels, G. L., Faas, B. H., Green, C. A., Smart, E., Maaskant-van Wijk, P. A., Avent, N. D., Zondervan, H. A., von dem Borne, A. E., and van der Schoot, C. E. The VS and V blood group polymorphisms in Africans: a serologic and molecular analysis. *Transfusion* 38:951-958, 1998.): The Cde$^s$ haplotype contains a RHD-CE-D hybrid gene encoding for an antigen C immunoreactivity, in which exons 4 to 7 derived from RHCE and exon 3 has a RHD like structure but possesses a RHCE specific Thr at codon 152.

Several additional RHD positive alleles occurring in RhD negative individuals have previously been partly or fully characterized (Table 10). Three of these ten published RHD alleles represented RHD-CE-D hybrid alleles in which the RHCE specific stretch encompassed at least exons 4 to 7. For each of these three hybrid RHD alleles, alleles were found whose patterns would be compatible (Table 10). Out of the seven RhD negative patterns observed in the present study, six were compatible with such type of hybrid RHD allele. Seven out of ten published RHD alleles represented deletions, nonsense mutations or a pseudogene. None of these alleles occurred in this study, which may indicate that they are rare in whites. In another embodiment, the invention provides for the detection or determination of the RHD allele previously described as RHD exon 9 negative (Gassner, Transfusion 37:1020ff, 1997), preferably representing an hybrid RHD-CE(9)-D hybrid allele, by its lack of RHD specific sequences in parts of intron 7 and intron 8. The specific steps carried out in this method may be any of the steps referred to in the further methods of the invention described in the specification, alone or in any combination.

In a particularly preferred embodiment the nucleic acid molecular structure of the present invention wherein the RHD-CE-D hybrid of the present invention encodes a polypeptide having antigen C reactivity.

Antigen C is a blood group antigen belonging to the RH blood group system known in the art and designated as 004.002 according to the ISBT nomenclature. A description is contained in many textbooks on immunohematology, e.g. Reid, M. E. and Lomas-Francis, C. *The Blood Group Antigen Facts Book*, San Diego: Academic Press, 1997.

Furthermore, in a preferred embodiment of the invention the nucleic acid molecular structure of the invention or a nucleic acid molecule being derived from the RHD gene comprises a single nucleotide substitution within the coding region of the RHD gene or within a 5' or 3' splice site.

The term "a nucleic acid molecule derived from the RHD gene" is intended to mean that this nucleic acid molecule originates from the RHD gene but carries a mutation, deletion, insertion, substitution or duplication within the coding region, any of the splice sites or a non-coding region. Preferably, said nucleic acid molecule gives rise to an aberrant polypeptide.

In a further preferred embodiment said nucleotide substitution gives rise to a stop-codon at codon 16.

In a more preferred embodiment said substitution gene gives rise to an RHD(W16X) mutation.

In an additional more preferred embodiment said substitution is a G→A substitution at nucleotide position 48.

In a further preferred embodiment of the invention said nucleotide substitution gives rise to a stop codon at codon 330.

In a more preferred embodiment of the invention said substitution gives rise to a RHD(Y330X) mutation.

In an even more preferred embodiment of the invention said substitution is a C→G substitution at nucleotide position 985.

In another preferred embodiment of the invention said substitution gives rise to a missense mutation at codon 212.

In another preferred embodiment of the invention said substitution gives rise to a RHD(G212V) missense mutation.

In a more preferred embodiment of the invention said substitution is a G→T substitution at nucleotide position 635.

In a different preferred embodiment of the invention said substitution gives rise to a mutation within a 4 nucleotide sequence, a 6-nucleotide sequence or an 8-nucleotide sequence comprising the consensus splice site at the exon 8/intron 8 boundary.

In another more preferred embodiment of the invention said substitution give rise to a RHD(G1153(+1)A) mutation.

In an additional more preferred embodiment of the invention said substitution is a substitution at the 5' splice site intron 8 from AGgt to AGat.

In a further more preferred embodiment the nucleic acid molecular structure of the invention or a nucleic acid molecule being derived from the RHD gene correlates with a RhD-negative phenotype.

In another preferred embodiment of the invention said substitution gives rise to a mutation within a 4-nucleotide, a 6-nucleotide sequence or an 8-nucleotide sequence comprising the consensus splice site of the exon 3/intron 3 boundary.

In a further preferred embodiment of the invention said substitution gives rise to a RHD(G486(+1)A) mutation.

In an additional more preferred embodiment of the invention said substitution is a substitution at the 5' splice site intron 3 from ACgt to ACat.

In a further preferred embodiment of the invention said substitution gives rise to a mutation within a 4-nucleotide sequence, a 6-nucleotide sequence or an 8-nucleotide sequence comprising the consensus splice site of exon Winton 9 boundary.

In another preferred embodiment said substitution gives rise to a RHD(K409K) mutation.

In an additional more preferred embodiment of the invention said substitution is a substitution at the 5' splice site intron 9 from AGgt to AAgt.

In a more preferred embodiment of the invention the nucleic acid molecular structure of the invention or a nucleic acid molecule being derived from the RHD gene correlates with a $D_{el}$-phenotype.

In summary and referring to the above, RHD positive alleles can harbour single nucleotide substitutions leading to termination or reduction of the D-antigen expression. Using the improved detection methods disclosed in the present invention four RHD positive alleles in RhD negatives were found that had not been described previously. Two alleles, RHD(W16X) and RHD(Y330X) harbored stop codons preventing the expression of the full RhD protein. In three alleles, splice site mutations were found that may prevent correct splicing and RhD expression.

These alleles typed RHD positive in all RHD PCR methods tested, and a correct antigen D prediction necessitates a specific detection of these alleles or of polymorphisms linked to these alleles.

Previously, the discrimination of RHD homozygotes from RHD heterozygotes was difficult. The prevalent RHD negative allele could not be detected specifically (Flegel, Transfus. Med. 8:281, 1998; Cossu, Electrophoresis 17:1911, 1996). The above defined mutation found in accordance with the present invention provides the basis for the detection of the prevalent RHD negative haplotypes, and hence true RHD genotyping is now feasible.

The invention also relates to a process to specifically detect a RHD negative haplotype in a sample by utilizing any structural feature or nucleotide sequence or both of the above-described nucleic acid molecular structure or combinations thereof with techniques known in the art, preferably amplification reactions, such as polymerase chain reaction (PCR), more preferably by PCR-RFLP, PCR-SSP or long-range PCR.

The described PCR-RFLP and long-range PCR methods utilize either Rhesus box sequences or Rhesus box flanking sequences. By utilizing the same DNA stretches or combinations thereof, other methods, like PCR-SSO or biochips, can be developed or applied.

In one preferred embodiment of the present invention said process to specifically detect a common RHD negative haplotype comprises the following steps:
(a) isolating the DNA from a blood sample or blood donor,
(b) hybridizing at least two oppositely oriented primers under stringent conditions to the DNA so as to carry out a PCR;
(c) amplifying the target sequence;
(d) separating the amplification products on a gel; and
(e) analyzing the amplicons.

Said sample may or may be derived from blood, serum, sputum, feces or other body fluid. The sample to be analyzed may be treated as to extract, inter alia, nucleic acids. The isolation of DNA from preferably EDTA- or citrate agglutinated blood samples can be carried out by a modified salting out methods, following the standard techniques as described in Gassner, Transfusion 37: 1020, 1997. The primers are preferably oligonucleotides that either occur naturally or in a purified restriction digest or are produced synthetically. The primers are preferably single stranded for a maximum of efficiency in the method of the present invention, and are preferably oligodeoxyribonucleotides. Purification of said primers is generally envisaged, prior to their use in the methods of the present invention, said purification comprising High Performance Liquid Chromatography (HPLC) or Polyacrylamide gel electrophoresis (PAGE), all technologies that are well known to the skilled artisan. Amplification methods such as PCR or LCR are well known in the art and described, for example in Flegel, Transfusion Medicine 8 (1998), 281-302; Maaskant, Transfusion 38 (1998), 1015-1021 and Legler, Transfusion (1996), 426-31.

According to the present invention a preferred method to detect the RHD deletion is performing PCR-RFLP using the expand high fidelity PCR-system and non-specific primers binding 5' of the end of the Rhesus box identity region as well as primers specific for the downstream Rhesus box and binding 3' of the end of the Rhesus box identity region. The PCR conditions involve preferably annealing at 65° C., extension for 10 min at 68° C. Thereafter, PCR amplicons are digested with PstI for 3 h at 37° C. and fragments resolved using 1% agarose gel. Additional preferred methods are further described in examples 10 and 11.

Another embodiment of the invention relates to a process to specifically detect a common RHD negative haplotype comprising the detection of the hybrid Rhesus box.

The detection of the hybrid Rhesus box provides the practitioner with an unambiguous result as regards the nature of the corresponding RHD allele. If the hybrid Rhesus box is detected, then the RHD gene is deleted. Detection of the hybrid Rhesus box is preferentially effected by using an oligonucleotide that specifically hybridizes to a region comprising the breakpoint. The oligonucleotide used for hybridization must directly hybridize to that breakpoint and, in addition, hybridize to at least 943 nucleotides 5' and 3' of the breakpoint. Hybridization occurs preferably under stringent conditions such as 0.2×SSC, 0.1% SDS at 65° C. The actual breakpoint within the hybrid Rhesus box may vary due to the exact nature of the putative crossover event. Accordingly, the hybrid Rhesus box may also be detected using a number of overlapping or non-overlapping oligonucleotides used for hybridization. The hybrid Rhesus box may also be detected using other protocols such as restriction analysis (preferably in combination with Southern blot analysis), or PCR technology, as described herein above.

Furthermore, another embodiment of the invention relates to a process to specifically detect a common RHD negative haplotype comprising assessing the nucleic acid molecular structure comprising the hybrid Rhesus box and the flanking regions thereof.

In accordance with the present invention, assessment of the molecular nucleic acid structure comprises analysis steps such as gel electrophoresis using either agarose gels or polyacrylamide gels, treatment with restriction-enzymes, blotting techniques, such as Southern or Northern blotting or related techniques, such as fluorescence-guided detection of hybridization and other techniques known in the art.

The present invention also relates to a process to specifically detect a RHD negative haplotype in a sample comprising the step of detecting any of the breakpoint regions mentioned in the present invention.

In a preferred embodiment the invention relates to the above-mentioned process wherein said detection or assessment comprises the determination of the length of a nucleic acid molecule comprising the hybrid Rhesus box or parts thereof.

Again, this preferred embodiment of the method of the invention utilizes standard separation techniques, such as gel electrophoresis or chromatography or standard techniques of nucleotide sequencing as known to a skilled artisan. Preferably the present invention utilizes a commercially available sequencing kit and an automatic sequencing machine from Applied Biosystems (ABI 373A or ABI 377), as further described in Example 5, for this purpose.

Another preferred embodiment of the invention relates to the above-mentioned process wherein said detection or assessment is effected by using PCR-RFLP, PCR-SSP or long-range PCR or a probe specifically hybridizing to the hybrid Rhesus box, preferably to the breakpoint or breakpoint region depicted in FIG. 4 or 5 or FIG. 12 or 13, or hybridizing to the upstream or downstream Rhesus box, preferably by Southern blot analysis, gel electrophoresis, biochip-analysis, molecular weight determination or fluorescence.

According to the present invention the term "hybridizing to" relates to stringent or non-stringent conditions. The setting of conditions is well within the skill of the artisan and to be determined according to protocols described, for example, in Sambrook, loc. cit. or Hames and Higgins, "Nucleic acid hybridization, a practical approach", IRC Press, Oxford (1985). The detection of specifically hybridizing sequences will usually require stringent hybridizing and washing conditions such as 0.2×SSC, 0.1% SDS at 65° C. Non-stringent hybridization conditions for the detection of homologous and not exactly complementary sequences may be set at 6×SSC, 1% SDS at 50° C. or 65° C. As is well known, the length of the probe and the composition of the nucleic acid to be determined constitute further parameters of the hybridization conditions.

Furthermore, the invention relates to a vector comprising the nucleic acid molecular structure or the nucleic acid molecule of the invention.

The vector may be used for propagation and/or expression or may be designed for gene transfer or targeting purposes. Methods of producing such vectors are well known in the art. The same holds true for cloning the nucleic acids of the mutation into said vectors, as well as the propagation of vectors in suitable hosts, etc.

The vector may particularly be a plasmid, a cosmid, a virus or a bacteriophage used conventionally in genetic engineering that comprise the nucleic acid molecule of the invention. Expression vectors derived from viruses such as retroviruses, vaccinia virus, adeno-associated virus, herpes viruses, or bovine papilloma virus, may be used for delivery of the nucleic acid molecules or vector of the invention into targeted cell populations. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

Such vectors may comprise further genes such as marker genes which allow for the selection of said vector in a suitable host cell and under suitable conditions. Preferably, the nucleic acid molecule of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used.

As mentioned above, the vector of the present invention may also be a gene transfer or targeting vector. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Additionally, the invention relates to a non-human host transformed with the vector of the invention.

Appropriate hosts comprise transgenic animals, cells such as bacteria, yeast cells, animal, preferably mammalian cells, fungal cells or insect cells. Transformation protocols including transfection, microinjection, electroporation, etc., are also well known in the art.

Further, the invention relates to a method of producing a protein product of the RHD gene comprising culturing the host of the invention under suitable conditions and isolating the protein product of the RHD gene.

It is preferred that the protein product of the RHD gene is exported into the culture medium where it can be collected according to conventions/methods. The term "culturing" as used in accordance with the present invention also comprises the raising of transgenic animals. Using appropriate vectors constructions and optionally appropriate feeds, the antigen may, e.g., be isolated from milk of, e.g. transgenic cows.

The invention additionally relates to a protein product of the RHD gene encoded by the nucleic acid molecule of the invention or produced by the method of the invention.

Preferably, the protein is in the same way post translationally modified and has the same chemical structure as naturally occurring antigen. Accordingly, said protein, when produced by the method of the invention, is preferably produced in human cells.

Furthermore, the invention relates to an oligonucleotide hybridizing under stringent conditions to a portion of the nucleic acid molecular structure or the nucleic acid molecules of the invention, wherein said portion comprises said (missense) mutation or said stop codon or to the complementary portion thereof or hybridizing to a breakpoint of the gene conversion identified here in the above.

In this embodiment of the invention, it is understood that the oligonucleotides hybridizes directly to the mutated sequence or to the breakpoint. The setting of stringent hybridization conditions is well described, for example, in Sambrook et al, "Molecular Cloning, A Laboratory Handbook" CSH Press, Cold Spring Harbor 1989 or Hames and Higgins, "Nucleic acid hybridization, a practical approach", IRL Press, Oxford (1985). Thus, the detection of the specifically hybridizing sequences will usually require hybridization and washing conditions such as 0.2×SSC, 0.1% SDS at 65°. As is well known, the length of the probe and the composition of the nucleic acid to be determined constitute further parameters of the stringent hybridization conditions. Preferably, the oligonucleotide is a deoxynucleotide. It is further preferred that the oligonucleotide comprises 12 to 50 nucleotides and more preferably 15 to 24 nucleotides. The hybridization to the breakpoint may be under stringent or non-stringent conditions. An example of non-stringent hybridization conditions is hybridization and washing at 50° C. in 4×SSC, 0.1% SDS.

Further, the invention relates to an antibody or an aptamer specifically binding to the protein product of the RHD gene of the invention.

The antibody may be tested and used in any serologic technique well known in the art, like agglutination techniques in tubes, gels, solid phase and capture techniques with or without secondary antibodies, or in flow cytometry with or without immunofluorescence enhancement.

The antibody of the invention may be a monoclonal antibody or an antibody derived from or comprised in a polyclonal antiserum. The term "antibody", as used in accordance with the present invention, further comprises fragments of said antibody such as Fab, F(ab')$_2$, Fv or scFv fragments; see, for example, Harlow and Lane, "Antibodies, A Laboratory Manual" CSH Press 1988, Cold Spring Harbor, N.Y. The antibody or the fragment thereof may be of natural origin or may be (semi) synthetically produced. Such synthetic products also comprise non-proteinaceous as semi-proteinaceous material that has the same or essentially the same binding specificity as the antibody of the invention. Such products may, for example, be obtained by peptidomimetics.

The term "aptamer" is well known in the art and defined, e.g., in Osborne et al., Curr. Opin. Chem. Biol. I (1997), 5-9 or in Stall and Szoka, Pharm. Res. 12 (1995), 465-483.

Furthermore, the invention relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising hybridizing the oligonucleotide of the invention under stringent conditions to nucleic acid molecules comprised in the sample obtained from a human and detecting said hybridization.

Preferably, the method of the invention further comprises digesting the product of said hybridization with a restriction endonuclease or subjecting the product of said hybridization to digestion with a restriction endonuclease and analyzing the product of said digestion.

This preferred embodiment of the invention allows by convenient means, the differentiation between an effective hybridization and a non-effective hybridization. For example, if the wild type RHD gene comprises an endonuclease restriction site, the hybridized product will be cleavable by an appropriate restriction enzyme whereas a mutated sequence will yield no double-stranded product or will not comprise the recognizable restriction site and, accordingly, will not be cleaved. Alternatively, the hybridizing oligonucleotide may only hybridize to the mutated sequence. In this case, only a hybrid comprising the mutated sequence, but not the wild type sequence, will be cleaved by the appropriate restriction enzyme. The analysis of the digestion product can be effected by conventional means, such as by gel electrophoresis which may be optionally combined by the staining of the nucleic acid with, for example, ethidium bromide. Combinations with further techniques such as Southern blotting are also envisaged.

Detection of said hybridization may be effected, for example, by an anti-DNA double-strand antibody or by employing a labeled oligonucleotide. Conveniently, the method of the invention is employed together with blotting techniques such as Southern or Northern blotting and related techniques. Labeling may be effected, for example, by standard protocols and includes labeling with radioactive markers, fluorescent, phosphorescent, chemiluminescent, enzymatic labels, etc.

The invention also relates to a method to simultaneously detect the presence of RHDΨ and any of the RHD molecular structures of the invention comprising hybridizing the oligonucleotide of the invention and at least an other oligonucleotide hybridizing to a RHDΨ structure under stringent conditions to nucleic acid molecules comprised in the sample obtained from a human and detecting said hybridization.

The present invention further relates to a method for testing simultaneously for the presence of RHDΨ and any of the RHD molecular structures of the present invention in a sample comprising determining the nucleic acid sequence of at least a portion of the nucleic acid molecular structure or nucleic acid molecule of the present invention, said portion encoding said (missense) mutation, said stop codon or a breakpoint of said hybrid gene and determining of at least a portion of a RHDΨ structure.

The invention additionally relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising determining the nucleic acid sequence of at least a portion of the nucleic acid molecular structure or the nucleic acid molecule of the invention, said portion encoding said (missense) mutation, said stop codon or a breakpoint of said hybrid gene.

Preferably, the method of the invention further comprises, prior to determining said nucleic acid sequence, amplification of at least said portion of said nucleic acid molecular structure.

Moreover, the invention relates to a method for testing simultaneously for the presence of RHDΨ and any of the RHD molecular structures of the present invention in a sample comprising carrying out an amplification reaction using a set of primers that amplifies at least a portion of said sequence wherein at least one of the primers employed in said amplification reaction is the oligonucleotide of the present invention and at least a primer amplifying (e.g. by specifically hybridizing to) a RHDΨ structure and analysing the amplified product(s).

RHDΨ is a RHD allele detected in D negatives that has been characterized by Singleton et al. (Singleton, B. K, Green, C. A., Avant, N. D., Martin, P. G., Smart, E., Daka, A., Narter-Olaga, E. G., Hawthorne, L. M., and Daniels, G. The presence of an RHD pseudogene containing a 37 base pair duplication and a nonsense mutation in Africans with the Rh D-negative blood group phenotype. *Blood* 95(1):12-18, 2000).

Furthermore, the invention relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising carrying out an amplification reaction using a set of primers that amplifies at least a portion of said sequence wherein at least one of the primers employed in said amplification reaction is the oligonucleotide of the invention.

Moreover, in a further embodiment the method of the invention wherein at least one of the primers employed in said amplification reaction is the oligonucleotide of the invention.

Preferably, amplification is effected by polymerase chain reaction (PCR). Other amplification methods such as ligase chain reaction may also be employed.

In a preferred embodiment of the method of the invention said PCR is PCR-RFLP, PCR-SSP or long-range PCR.

Additionally, in another preferred embodiment of the invention the molecular weight of the amplification product is analyzed. Said analysis of the molecular weight utilizes standard techniques, such as agarose gel electrophoresis, SDS-PAGE, mass spectrometry such as MALDI-TOF for this purpose, which are well known to the person skilled in the art.

In one preferred embodiment of the method of the invention, said method detects RHD positive alleles comprising the following steps:
(a) isolating DNA from a blood sample or blood donor;
(b) hybridizing at least two oppositely oriented primers under stringent conditions to the DNA so as to carry out a PCR;
(c) amplifying the target sequence;
(d) separating the amplification products on a gel; and
(e) analyzing the amplicons.

With regard to specific conditions to be applied in the various steps, it is referred to the corresponding description herein above.

In a preferred embodiment the RHD positive alleles are derived from a serologically RhD negative population. In another preferred embodiment the RhD-negative sample is selected from a Caucasian population.

The method of the invention will result in an amplification of only the target sequence, if said target sequence carries the or at least one mutation. This is because the oligonucleotide will, under preferably stringent hybridization conditions, not hybridize to the wild type sequence (with the consequence that no amplification product is obtained) but only to the mutated sequence. Naturally, primer oligonucleotides hybridizing to one or more as one, such as two mutated sequences may be employed in the method of the invention.

The latter embodiment may be favorable in cases where combinations of mutations are tested for. It is important to note that not all or none of said mutations are necessarily missense mutations. This may be true for cases where other types of mutations occur in combination with the above missense mutations or with the above gene conversion.

Preferably, in the method of the invention said amplification or amplification reaction is or is effected by the polymerase chain reaction (PCR). Other amplification methods such as ligase chain reaction may also be employed.

Further, the invention relates to a method for testing for the presence of a protein product of the RHD gene of the invention in a sample comprising assaying a sample obtained from a human for specific binding to the antibody or aptamer or phage of the invention.

Testing for binding may, again, involve the employment of standard techniques such as ELISAs; see, for example, Harlow and Lane, "Antibodies, A Laboratory Manual" CSH Press 1988, Cold Spring Harbor.

In another preferred embodiment the invention relates to a method for testing for the presence of a protein product of the RHD gene encoding the nucleic acid molecular structure or the nucleic acid molecule of the invention, comprising utilizing direct agglutination methods, indirect antiglobulin tests, monoclonal anti-D antibodies and adsorption/elution techniques.

Thus, the embodiment may comprise direct agglutination with two monoclonal anti-D antibodies, alternatively indirect antiglobulin tests using a gel matrix comprising an oligoclonal anti-D antibody, in a further alternative using monoclonal anti-Rhesus antibodies in another alternative adsorption of polyclonal anti-D antibodies to red cells and elution using a chloroform technique. Further description of the methods is given in example 18.

Preferably, in the method of the invention said sample is blood, serum, plasma, fetal tissue, saliva, urine, mucosal tissue, mucus, vaginal tissue, fetal tissue obtained from the vagina, skin, hair, hair follicle or another human tissue.

Furthermore, the method of the invention preferably comprises the step of enrichment of fetal cells. This enrichment may be achieved by using appropriate antibodies, lectins or other reagents specifically binding fetal cells or by any technique attempting the differential separation of maternal and fetal cells, like by density gradients. Also preferably, in said method fetal DNA or mRNA from maternal tissue like peripheral blood, serum or plasma may be extracted, advantageously according to conventional procedures.

In an additional preferred embodiment of the method of the invention, said nucleic acid molecule or proteinaceous material from said sample is fixed to a solid support.

Preferably, said solid support is a chip.

The advantages of chips are well known in the art and need not be discussed herein in detail. These include the small size as well as an easy access of computer based analysis of analytes.

Furthermore, the present invention relates to the use of the nucleic acid molecular structure or the nucleic acid molecule of the invention for the analysis of a negative or a positive Rhesus D phenotype.

The analysis can be effected, for example, on the basis of the methods described herein above.

The invention also relates to the use of the nucleic acid molecular structure or the nucleic acid molecule of the invention, the vector of the invention or the protein product of the RHD gene of the invention for the assessment of the affinity, avidity and/or reactivity of monoclonal anti-D or anti-C antibodies or of polyclonal anti-D or anti-C antisera or of anti-globulin or of anti-human-globulin antisera or of preparations thereof.

Anti-C is a monoclonal antibody or polyclonal antiserum binding to antigen C.

The invention also relates to the use of cells, preferably red blood cells, from probands carrying the nucleic acid molecular structure or the nucleic acid molecule of the invention for the assessment of the affinity, avidity and/or reactivity of monoclonal anti-D or anti-C antibodies or of polyclonal anti-D or anti-C antisera or of anti-globulin or of anti-human-globulin antisera or of preparations thereof.

Said preparations can be provided according to techniques well known in the art. Said preparations may comprise stabilisators such as albumins, further sodium azide, salt ions, buffers etc. The formulation of the preparation may have an influence on the binding characteristics of the antibodies, as is well known in the art.

For example, in a first step, the Rhesus D gene of a carrier or of a blood donor and its allelic status is analyzed and it is determined whether said gene comprises a mutation that was found in accordance with the present invention. In a second step, said mutation is correlated to a certain RhD antigen density on the surface of red blood cells. Conveniently, said correlation can be established by data provided in the present invention (such as mutations per se) and techniques that are well known in the art (see, e.g. Jones et al. 1996, Flegel and Wagner, 1996). In a third step, the features of an antibody or an antiserum such as reactivity, sensitivity, affinity, avidity, and/or specificity are determined with suitable blood group serological techniques preferably using red blood cells that were molecularly and with respect to the RhD antigen surface density characterized as described in step 2. Such data can be used, for example, in quality controls, standardization, etc.

The invention will be most useful for the characterization, standardization and quality control of monoclonal and polyclonal antisera, preferably anti-D monoclonals or antisera. Further, for example, anti-globulin and anti-human-globulin antisera can be characterized on the basis of the teachings of the present invention. An appropriately characterized anti-D monoclonal antibody can be conveniently used in RhD diagnostics. For example, a suitably characterized monoclonal antibody will be useful in determining the D antigen density on the surface of blood cells. Cut-off values for monoclonal antibodies useful in diagnosis can thus be established. This is important for the quality control of antibodies used in RhD diagnosis.

Thus, the invention also relates to a method for the characterization of monoclonal antibodies or polyclonal antisera or of a preparation thereof, said method comprising
(a) testing the nucleic acid of sample of a proband for the presence of a breakpoint or mutation as defined in accordance with the invention;
(b) correlating, on the basis of the mutation or deletion status and the allelic status of the RHD gene, the nucleic acid with the density of the protein product of the RHD gene on the surface of red blood cells of said proband;
(c) reacting said monoclonal antibodies or polyclonal antisera or said preparation thereof with a cell carrying the protein product of the RHD gene on its surface;
(d) characterizing said monoclonal antibodies or polyclonal antisera or said preparation thereof on the basis of the results obtained in step (c).

As regards the term "allelic status", this term describes the possibilities that the RHD alleles in a proband are present in a homozygous, heterozygous or hemizygous state. Also comprised by this term is the possibility that the two alleles carry two different mutations (including the conversion) defined herein above.

In a preferred embodiment of the method of the invention, said characterization comprises the determination of reactivity, sensitivity, avidity, affinity, specificity and/or other characteristics of antibodies and antisera.

Furthermore preferred is a method wherein said cell carrying the protein product of the RHD gene on its surface is a red blood cell.

The invention also relates to a method for determining whether a patient in need of a blood transfusion is to be transfused with RhD negative blood from a donor comprising the step of testing a sample from said patient for the presence of one or more nucleic acid molecular structures or nucleic acid molecules of the invention, wherein a positive testing for two different of said nucleic acid molecular structures or nucleic acid molecules is indicative of the need for a transfusion with Rh negative blood. Alternatively, a positive testing indicating the concomitant presence of two identical copies of one of said nucleic acid molecular structures or nucleic acid molecules is indicative of the need for a transfusion with Rh negative blood.

Alternatively, a negative testing for the presence of the nucleic acid molecular structure or nucleic acid molecule representative of the common RHD negative haplotype with or without a negative testing for one or more nucleic acid molecular structures or nucleic acid molecules representative of the other RHD negative nucleic acid molecular structures or nucleic acid molecules of this invention permits the transfusion of blood that is typed as RhD positive. The invention has important implications for devising a transfusion therapy in humans. For example, it can now be conveniently tested whether the patient actually needs a transfusion with a RhD negative blood or whether such precautions need not be taken.

The invention also relates to a method for determining whether blood of a donor is suitable for transfusion to a patient in need thereof who should not be exposed to antigen C comprising the step of testing a sample from said donor for the presence of the nucleic acid molecular structure of the present invention wherein a positive testing for the nucleic acid molecular structure of the present invention precludes the transfusion of the donors blood.

Furthermore, the invention relates to a method for determining whether blood of a donor may be used for transfusion to a patient in need thereof comprising the step of testing a sample from said donor for the presence of one or more of said nucleic acid molecular structures or nucleic acid molecules of the invention, wherein a negative testing for the nucleic acid molecular structures representative of the common RHD negative haplotype with or without a negative testing for one or more nucleic acid molecular structures or nucleic acid molecules representative of the other RHD negative haplotypes of this invention excludes the transfusion the donors blood to a patient that is typed as RhD negative.

The invention also relates to a method for determining whether the blood of a donor may be transfused to a patient typed as RhD negative comprising the step of testing a sample from said donor for the presence of one or more nucleic acid molecular structures or nucleic acid molecules of the invention, wherein a positive testing for two different of said nucleic acid molecular structures or nucleic acid molecules is indicative of the possibility to transfuse the donors blood to a patient typed as RhD negative.

Alternatively, a positive testing indicating the concomitant presence of two identical copies of one of said nucleic acid molecular structures or nucleic acid molecules is indicative of the possibility to transfuse this donors blood to a patient that is typed as RhD negative.

The samples referred to in the above recited methods may be samples that are referred to throughout the specification, such as blood, serum, etc.

As regards the guidelines for transfusing a patient on the basis of any of the above recited methods, the utmost care must be taken that suboptimal transfusion policy is avoided. The risk factor is always to be considered by the physician in charge. In all cases, the potential risk for the patient is to be minimized.

The invention also relates to a method for assessing of the risk of a RhD negative mother of conceiving or carrying an RhD positive fetus or of the risk of a mother having an anti-D titer of conceiving or carrying a fetus at risk to develop hemolytic disease of the newborn comprising assessing a sample obtained from the father of the fetus for the presence of one or more of said nucleic acid molecular structures or nucleic acid molecules of the invention, wherein a negative testing for nucleic acid molecular structures or nucleic acid molecules representative of the common RHD negative haplotype with or without a negative testing for one or more nucleic acid molecular structures or nucleic acid molecules representative of the other RHD negative haplotypes of this invention is indicative for a high risk of conceiving an RhD positive fetus.

In a preferred embodiment of the method of the present invention said nucleic acid molecular structure carries mutations or deletions.

The invention also relates to a method for determining whether the father is RhD negative comprising the step of testing a sample from the father for the presence of one or more nucleic acid molecular structures or nucleic acid molecules of the invention, wherein a positive testing for two different of said nucleic acid molecular structures or nucleic acid molecules is indicative of the father being RhD negative.

Alternatively, a positive testing indicating the concomitant presence of two identical copies of one of said nucleic acid molecular structures or nucleic acid molecules representative of RHD negative haplotypes is indicative of the father being RhD negative.

Furthermore, the invention relates to a method for assessing the possibility or likelihood of a man being the father of a child by assaying a sample obtained from said man for the presence of one or more of said nucleic acid molecular structures or nucleic acid molecules of the invention, wherein the test results are used to determine the homozygosity for, the heterozygosity for or the absence of any nucleic acid molecular structures or nucleic acid molecules representative of the RHD negative haplotype of the present invention used to infer the possibility or likelihood of said man being the father of the child.

The preparation may be a diagnostic or pharmaceutical preparation.

The pharmaceutical composition of the present invention may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition.

The invention also relates to a method of treating a pregnant woman being Rhesus D negative wherein the fetus does not carry two nucleic acid molecular structures or nucleic acid molecules of the invention or is not homozygous for any nucleic acid molecular structure or nucleic acid molecule of the invention, comprising administering anti-D to said woman.

Pregnant women may be currently treated with an anti-D prophylaxis, when a Rhesus negative mother carries a RhD positive fetus. The invention allows the discrimination of an anti-D prophylaxis requirement depending on the status of the mother's and/or the fetus' possessing a RhD protein of the invention. One or more of the RhD proteins of the invention may be prone to immunization of their carriers and, hence, would be indicative for the therapy of the mother. Similarly, one or more RhD proteins of the invention, when carried by the fetus, may be known to be of low immunogenicity to the mother and, hence, would be indicative for the omission of anti-D prophylaxis in difference to current clinical therapy.

The administration can be effected by standard routes and doses which can be defined by the attending physician; Mollison, 1993. Preferably, a monoclonal anti-D or combinations/mixtures of monoclonal anti-Ds is/are administered in doses of 50 µg to or exceeding 500 µg anti-D antibody/antisera for intravenous or intramuscular administration (Bowman, 1998). For the quality control of these anti-D antibodies/antisera, the results and methods provided by the present invention may be advantageously employed.

The invention also relates to the use of a phage, aptamer, monoclonal antibody or a polyclonal antisera or a preparation thereof as characterized in the present invention for determination of the protein product of the RHD gene.

In a preferred embodiment of said use, said determination of the protein product of the RHD gene is effected in connection with blood group typing.

Furthermore, the invention relates to a preparation comprising the antibody or aptamer or phage of the invention.

The present invention also relates to a method of identifying an antibody $V_H$ or $V_L$ chain or a combination thereof or an aptamer specifically binding to a protein product of the RHD gene of the invention comprising (a) contacting the protein product of the RHD gene of the invention with a phage library displaying $V_H$ or $V_L$ chains or combinations thereof on the surface of the phage or with aptamers;

(b) identifying phage or aptamers that bind to said protein product of the RHD gene; and optionally (c) repeating steps (a) and (b) one or more times.

The preparation of phage library and the screening/identification of desired antibody (chains) per se is well known in the art and reviewed, for example, in Winter et al, Annu. Rev.

Immunol. 12 (1994), 433-455 and references cited therein. Also, aptamers can be prepared and cloned in phage according to conventional protocols. Whereas single $V_H$ or $V_L$ chains may be identified by the method of the invention as binding to the protein product of the RHD gene of the invention, it is preferred to identify $V_H$-$V_L$ combinations expressed by the phage because this situation resembles the situation of natural antibody binding. By repeating steps (a) and (b) one or more times, better binding specificities may be identified. Protocols for the optimization of binding properties such as affinities, including elution steps for removing bound phage, are well established in the art. For example, once a $V_H$ chain with a convenient binding capacity has been found, $V_L$ chains may be identified that significantly improve the binding capacity of the antibody, e.g. by replacing the $V_L$ chain that was associated with the $V_H$ chain in the first selection step with a more suitable $V_L$ chain.

The invention also relates to a method of identifying a monoclonal antibody specifically binding to a protein product of the RHD gene of the invention comprising
(a) contacting the protein product of the RHD gene of the invention with one or more monoclonal antibodies;
(b) identifying monoclonal antibodies that bind to said protein product of the RHD gene; and optionally
(c) repeating steps (a) and (b) one or more times.

The invention also relates to a method of identifying an antibody $V_H$ or $V_L$ chain or a combination thereof or an aptamer specifically binding to a protein product of the RHD gene of the invention comprising
(aa) contacting said protein product of the RHD gene and
(ab) a normal D polypeptide
wherein the normal D polypeptide is present in a molar mass that is higher, equal or less than the protein product of the RHD gene of (aa) with a phage library displaying $V_H$ or $V_L$ chains or combinations thereof on the surface of the phage or with aptamers;
(b) identifying phage or aptamers that bind to said protein product of the RHD gene of (a); and optionally
(c) repeating steps (a) and (b) one or more times.

Particularly preferred in step (ab) is that the molar mass of the normal D polypeptide is higher than that of the protein product of the RHD gene of (aa).

In the case that only one round of selection is employed for the identification (i.e. when step (c) does not apply), it is preferred that the number of protein product of the RHD gene of (aa) is in molar excess over the number of phage particles. The preferred embodiments of the method of identifying an antibody $V_H$ or $V_1$ chain or of a combination thereof or of an aptamer described hereinbefore equally apply to this embodiment of the invention.

The invention also relates to a method of Identifying a monoclonal antibody specifically binding to a protein product of the RHD gene of the invention comprising
(aa) contacting the protein product of the RHD gene and
(ab) a normal D polypeptide
wherein the normal D polypeptide is present in a molar mass that is higher, equal or less than the protein product of the RHD gene of (aa) with one or more monoclonal antibodies;
(b) identifying monoclonal antibodies that bind to said protein product of the RHD gene of (aa); and optionally
(c) repeating steps (a) and (b) one or more times.

Preferably, the protein product of the RHD gene is exposed on the surface of a cell. An appropriate surface is the surface of an erythrocyte. However, other host cells may be transfected with a vector suitable for expression of the protein product of the RHD gene of the invention and express the same on their surface. Antibodies may also bind to recombinant proteins of or parts of proteins of D antigen and purified proteins.

It is further preferred that the polypeptide or host cell is affixed to a solid support. Suitable examples for solid supports are microtiter plates or beads.

In an additionally preferred antibody, subsequent to step (b) or (c), the following step is carried out:
(d) identifying the amino acid sequence of the $V_H$ or $V_L$ chains and/or identifying the nucleic acid sequences encoding said amino acid sequence.

The identification of the amino acid/nucleic acid sequences can be effected according to conventional protocols; see, e.g., Sambrook et al., loc. cit.

Hence and in summary, the present invention provides means and methods for the detection of RHD haplotypes, comprising common RHD negative haplotypes, as described above, as well as presumably rare RHD positive alleles in serologically RhD negative populations. Latter alleles, harbouring RHD sequences and therefore determined as RHD-positive, can comprise either RHD/RHCE hybrid genes, stop codons, splice site mutations or gene deletions, that terminate or reduce the RhD antigen expression. Carrying out the improved detection methods of the invention, it was surprisingly found, that several samples, determined as RhD negative in routine serology, could be identified having RHD positive alleles. Furthermore, some of those samples were even RhD antigen positive when performing a detection assay based on adsorption and elution, indicating that the molecular basis for the RHD positive alleles in RhD negatives is more heterogenous than anticipated. Advantageously, the disclosure content of the present invention now provides new and practicable nucleic acid amplification techniques to determine whether RHD specific sequences cause RhD positive or RhD negative phenotypes.

In a particularly preferred embodiment the method of present invention, wherein, in the case that only one round of selection is employed for the identification, the number of protein molecules of the RHD gene of (a) is in molar excess over the number of phage particles.

Moreover, the present invention relates to the use of cells, preferably red blood cells comprising the protein product of the RHD gene of the present invention or produced by the method of the present invention, from probands for the assessment of the affinity, avidity and/or reactivity of monoclonal anti-D or anti-C antibodies of the present invention or of polyclonal anti-D or anti-C antisera or of anti-globulin or of anti-human-globulin antisera or of preparations thereof.

Furthermore, the invention relates to the use of SMP1 polymorphisms to determine specific RH(RHD-RHCE)-haplotypes genetically linked to said polymorphisms.

Basis for this embodiment of the present invention is provided by the unique structure of the RH locus comprising three genes: RHD, RHCE, and SMP1. The nucleotide sequence of the latter gene has been deposited in the Genbank as putative member of an 18 kDa small membrane protein family. Its function is as yet unknown. It shows homology to an open reading frame on chromosome 21 (Reboul, Genome res. 9:242, 1999). Its position between both RH genes implies that any polymorphism of the SMP1 gene would be tightly linked to a specific RH haplotype, and it might be anticipated that functionally relevant mutations of the SMP1 gene may cause selection pressure for or against specific RH haplotypes. Such factors might explain some previously unresolved issues of RH haplotype distribution, like the high frequency of RH negatives in Europe. Screening for polymorphisms in SMP1 is therefore of high interest for the understanding of the RH locus as well as for diagnostic applications thereof.

According to the present invention the term "polymorphism" relates to the existence in a population of more than one genetic structure or a gene of a haplotype or of a DNA segment. Nevertheless, sometimes such a genetic polymorphism does not always result in a differing phenotype, but may only be detected at the genetic level.

In another preferred embodiment the invention relates to a method to detect specific RH(RHD-RHCE)-haplotypes comprising the determination of SMP1-polymorphisms in the SPM1 gene by utilizing any structural feature or nucleotide sequence or both of the RH locus or combinations thereof with techniques known in the art, preferably by PCR-RFLP, PCR-SSP or long-range PCR.

Furthermore, the invention relates to a kit comprising
(a) the oligonucleotide of the invention; and/or
(b) the antibody of the invention;
(c) the aptamer of the invention; and/or
(d) the phage of the invention;
(e) a pair of primers useful for carrying out the amplification reaction of the invention.

Parts of the kit can be packaged individually in vials or in combination in containers or multicontainer units. The kit of the present invention may be advantageously used for carrying out the method of the invention and could be, inter alia, employed in a variety of applications referred to above. The manufacture of the kits follows preferably standard procedures which are known to people skilled in the art.

The present invention also relates to a process to determine the presence of an antigen C encoded by a RHD gene comprising the step of detecting any of the breakpoint regions mentioned in the present invention.

Finally, the invention relates to a process to determine the presence of an antigen C comprising the steps of the processes of the present invention.

The disclosure content of the documents as cited in this specification is herewith incorporated by reference.

THE FIGURES SHOW

FIG. 1 Schematic structure of the RH gene locus. The positions and orientations of the genes and the Rhesus boxes are indicated by open arrows and triangles, respectively (Panel A). The exons are shown as vertical bars and their exon number is indicated. The two RH genes have opposite orientation, face each other with their 3' ends, and are separated by about 30,000 bp. A third gene, SMP1, has the same orientation as RHD and is positioned in between RHD and RHCE. The RHD gene is flanked on both sides by the two highly homologous Rhesus boxes (b). All exons are shorter than 200 bp with the exception of the RHD and SMP1 3' terminal exons. Data used to establish this structure (Panel B) include the extension of genomic sequences represented in the cDNAs (horizontal arrows), identities and homologies to genomic clones (bar a: identity with dJ465N24; b: homology of RHD to dJ469D22; c: homology of RHD 3' part to dJ465N24; d: identity with dJ469D22). The positions of three bridging PCR reactions are indicated. The correct position of a nucleotide stretch previously reported by Okuda et al. (Okuda, Biochem. Biophys. Res. Commun. 263:378, 1999) as "spacer" sequence between RHD and RHCE is indicated by the bar labeled s.

Figure 2:
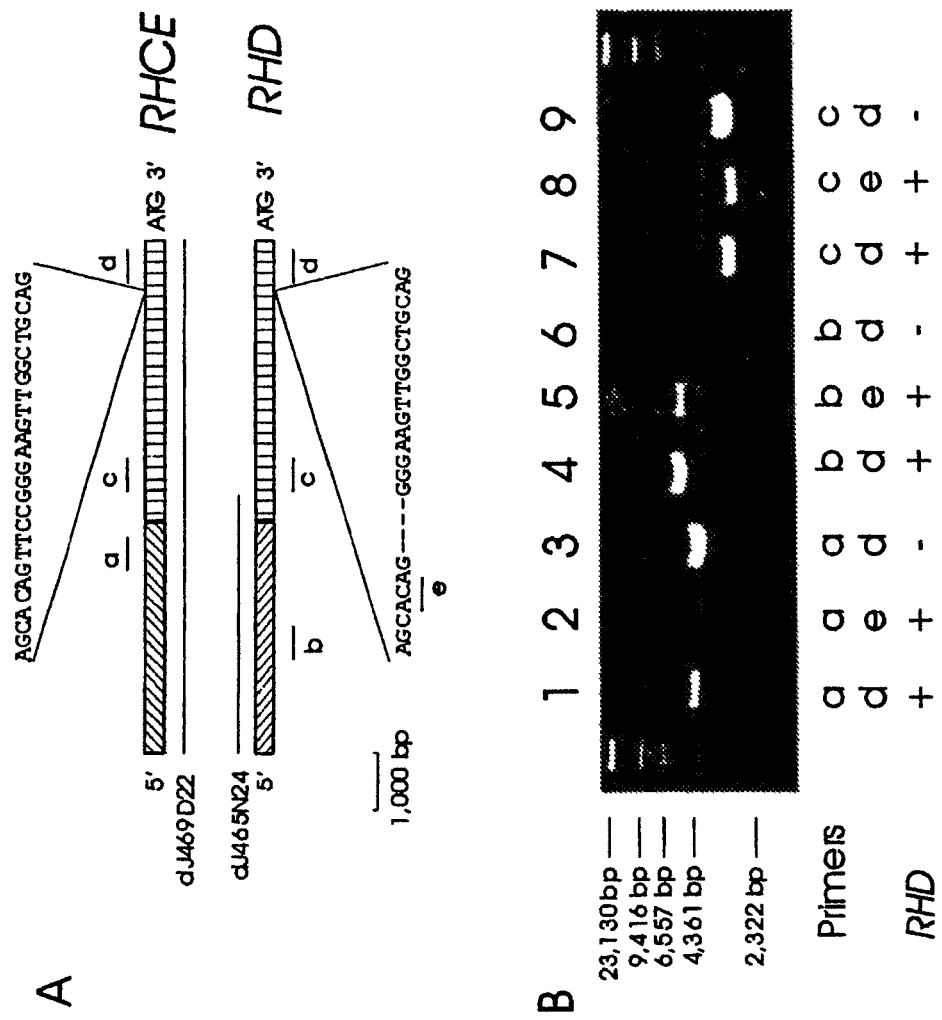

FIG. 2 Chromosomal organization of the DNA regions located 5' to the RHD and RHCE genes. The proposed structure of the RHCE and RHD 5' flanking regions is depicted (Panel A). A total of 4,941 bp immediately 5' of the ATG start codons are homologous between the RHCE and RHD genes (vertically hatched bars). No homology is present further beyond this homology region (diagonally hatched bars). Two genomic clones, dJ469D22 and dJ465N24, were utilized for primer design. DJ469D22 comprises the full length of the depicted RHCE region, whereas dJ465N24 extends only 466 bp into the homology region. The positions of several PCR primers are indicated (a, rey14a; b, rend32; c, rey15a; d, re014; e, re011d). This proposed structure is supported by several PCR reactions (panel B). Forward priming was done with primer a (RHCE specific, lane 1-3), primer b (RHD specific, lane 4-6), and primer c (RHCE and RHD homology region, lane 7-9). Amplicons were lacking for primer a with RHD specific reverse primer e (lane 2) and for primer b with RHD negative DNA (lane 6). The other seven PCR reactions yielded amplicons of the predicted sizes in accordance with the genomic structure shown in panel A.

FIG. 3 Chromosomal organization of the SMP1 gene. The SMP1 gene has seven exons. The positions and approximate sizes of the introns are shown (SEQ ID NOS 1-14). The start of the published cDNA (GenBank accession number AF081282) is separated by 15 nucleotides from the downstream Rhesus box. Exon 1 contains only 5' untranslated sequence, the SMP1 start codon is located in exon 2. Exon 7 contains 16 codons and 1,656 bp 3' untranslated sequences and is contiguous with the 3' untranslated sequence of RHCE exon 10.

FIG. 4 Chromosomal organization of the Rhesus boxes. The physical extension of the upstream Rhesus box (5' to RHD) is 9,145 bp (black bar). About 63% of the boxes' nucleotide sequence consists of repetitive DNA; the types of the repeat families are indicated. The overall homology between the upstream and downstream Rhesus box is 98.6%, but within an 1,463 bp identity region (horizontal arrows), there is only a single 4 bp insertion (double vertical line). A CpG-island (double-headed arrow) is located at the 3' end and is in the downstream Rhesus box (3' to RHD) adjacent to the SMP1 promoter.

FIG. 5 RHD gene deletion in the Rh negative haplotypes. Three 3,100 bp segments of the Rhesus boxes are shown. The upper line indicates the nucleotide sequence of the upstream Rhesus box in D-positives, the lower line the nucleotide sequence of the downstream Rhesus box in D-positives. The middle line gives the nucleotide sequence of the single Rhesus box carried by Rh negatives. Asterisks denote identical nucleotides. The RHD deletion occurred in a 903 bp segment of absolute identity that was part of a 1,463 bp identity region. The positions of primers rez7 and mb31 is shown (m indicates mismatch). PstI restriction sites are indicated by carets (^). The three Rhesus boxes are deposited at EMBL under accession numbers AJ252311 (upstream Rhesus box), AJ252312 (downstream Rhesus box), and AJ252313 (hybrid Rhesus box) (SEQ ID NO 15).

Figure 6:
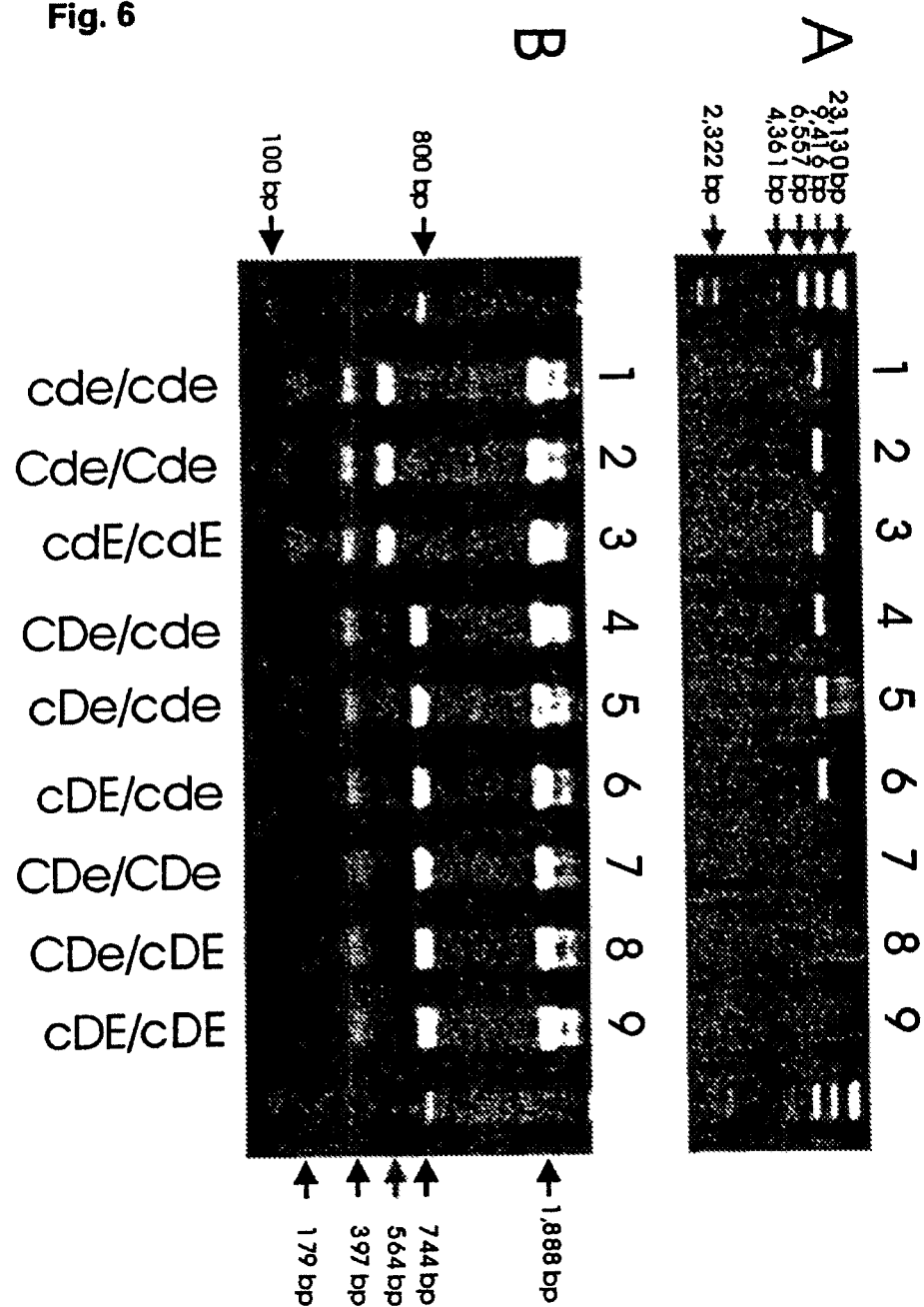

FIG. 6 Two technical procedures for specific detection of the RHD deletion in the common RHD negative haplotypes. A long-range PCR amplification with primers located in non-Rhesus box sequences (Panel A) and PCR-RFLP with primers located in the Rhesus boxes are shown (Panel B). The deduced genotypes are indicated. The primers of the long-range PCR were located 5' of the upstream Rhesus box (primer rez4) and in SMP1 exon 1 (primer sr9). RHD negative haplotypes were detected specifically (Panel A, lane 1-6). DNA homozygous for the RHD gene was negative, because the PCR cannot amplify the 70,000 bp DNA stretch of the RHD gene. For the PCR-RFLP method, the PCR amplicons (primer rez7 and mb31) were digested with PstI. In D-negatives, there are three PstI sites in the amplicon (see FIG. 5) resulting in fragments of 1,888 bp, 564 bp, 397 bp, and 179 bp (lane 1 to 3). The downstream Rhesus box of D-positives lacks one PstI-site resulting in fragments of 1,888 bp, 744 bp, and 397 bp (lane 7 to 9). RHD$^+$/RHD$^-$ heterozygotes show both fragments of 744 and 564 bp (lane 4 to 6). The 564 bp fragment appears weaker because heterodimers are not cut by PstI. Primer mb31 does not amplify the upstream Rhesus box of D-positives.

FIG. 7 Model of the proposed mechanism causing the prevalent RHD negative haplotypes in whites. The physical structure of the RHD and RHCE gene locus is depicted (panel A). An unequal crossing over between the upstream and downstream Rhesus boxes can be triggered by their high homology (panel B). The breakpoint region in the Rhesus boxes was found to be of 100% homology for 903 bp (see FIG. 5). Resolving the crossed over chromosome yields the RH gene structure of the extant RHD negative haplotype (panel C).

FIG. 8 DNA sequence of the hybrid Rhesus box of RHD negatives (SEQ ID NO 18).

FIG. 9 DNA sequence of the upstream Rhesus box of D-positives (SEQ ID NO 19).

FIG. 10 DNA sequence of the downstream Rhesus box of D-positives (SEQ ID NO 20).

FIG. 11 DNA sequence of the RHD promoter (SEQ ID NO 21). The last three nucleotides represent codon 1 of the RHD gene.

FIG. 12. Cde$^s$ breakpoint region in RHD intron 3. The nucleotide sequence of a part of the intron 3 of Cde$^s$, RHD and RHCE 2,938 to 3,636 bp 3' of the exon 3/intron 3 junction is shown (SEQ ID NOS 22-24). The human DNA sequence from clone RP3-469D22 on chromosome 1p35.1-36.13 containing the 5' part of the gene for RHCE (GenBank accession number AL031284) was taken as reference; numbers indicate the position in this sequence relative to the first base of intron 3 in the RHCE gene. The corresponding RHD gene sequence derives from GenBank accession number AL139426. Nucleotides indicating RHD or RHCE origin of the Cde$^s$ sequences are highlighted. A 154 bp DNA stretch comprising the breakpoint region of Cde$^s$ is indicated by asterisks.

FIG. 13. Cde$^s$ breakpoint region in RHD intron 7. The nucleotide sequence of a part of the intron 7 of Cde$^s$, RHD and RHCE about 2,726 to 3,719 3' of the exon 7/intron 7 junction is shown (SEQ ID NOS 25-27). The human DNA sequence from clone RP3-469D22 on chromosome 1p35.1-36.13 containing the 5' part of the gene for RHCE (GenBank accession number AL031284) was taken as reference; numbers indicate the position in this sequence relative to the first base of intron 7 in the RHCE gene. The corresponding RHD gene sequence derives from GenBank accession number AL139426. Nucleotides indicating RHD or RHCE origin of the Cde$^s$ sequences are highlighted. A 666 bp DNA stretch comprising the breakpoint region of Cde$^s$ is indicated by asterisks.

Figure 14:
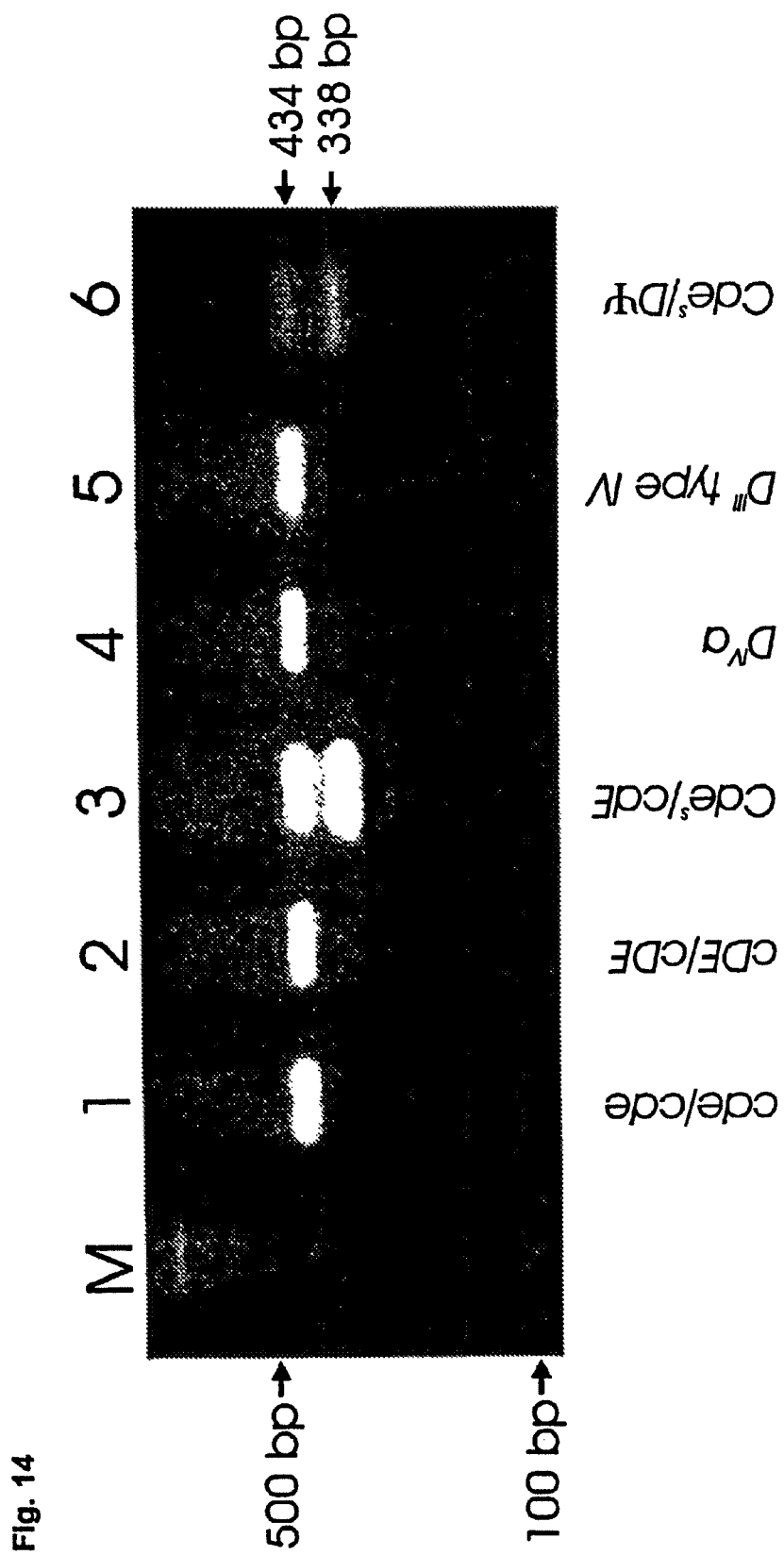

FIG. 14. Specific detection of Cde$^s$ by PCR-SSP. A PCR-SSP detecting the 3' breakpoint region of Cde$^s$ in intron 7 is shown. Both, a RHD negative sample (lane 1, ccddee) and a normal RHD positive sample (lane 2, ccD.EE) yield the 434 bp control product only, which is derived from the HGH gene. In contrast, a Cde$^s$ sample (CcddEe, lane 3) yields the 338 bp specific product, which is derived from the breakpoint region in intron 7, and in addition the 434 bp control fragment. This reaction is specific for Cde$^s$; the two partial D phenotypes D$^{IVa}$ (lane 4) and D$^{III}$ type IV (lane 5) do not yield a specific product. The reaction also detects Cde$^s$ specifically, if Cde$^s$ occurs in trans to other RHD alleles, like in a RHDΨ/Cde$^s$ sample (lane 6).

Figure 15:
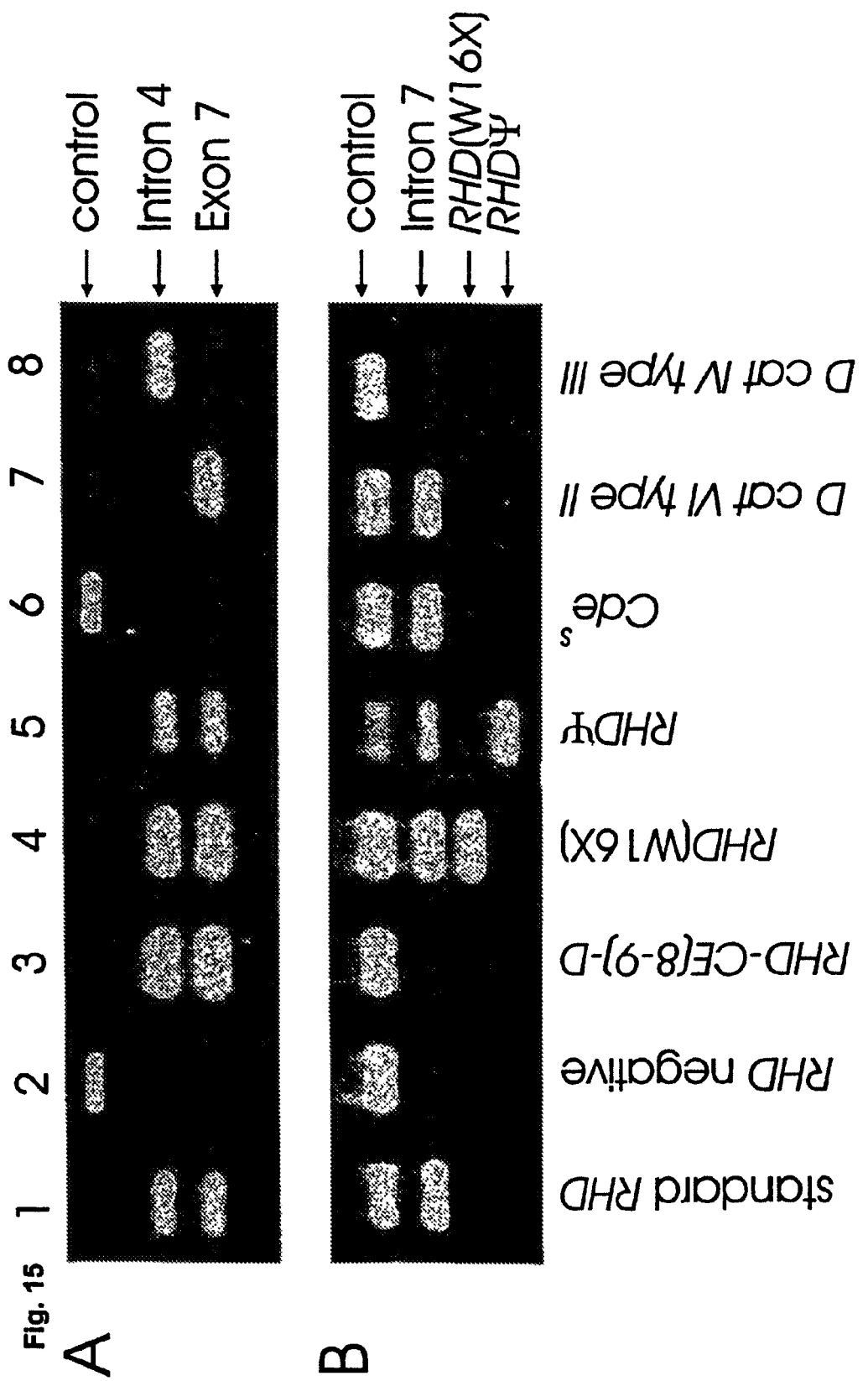

FIG. 15. RHD PCR-SSP for routine DNA typing. The PCR is performed as a modular system consisting of two multiplex reactions, an intron 4/exon 7 multiplex PCR-SSP (Panel A) and an intron 7 PCR enhanced by specific detection of RHD (W16X) and RHDΨ (Panel B). Results are shown for a normal D positive sample (lane 1), a normal D negative sample (lane 2), several rare D negative samples (lanes 3 to 6) and major D positive RHD variants (lanes 7 and 8). Standard D positive and D negative samples and D categories IV and VI are recognized in reaction A. RHD-CE(8-9)-D is detected in reaction B by the absence of the intron 7 band. The presence of RHD(W16X) and RHDΨ is also detected in reaction B. Band size is Panel A, control, 434 bp (HGH gene); intron 4, 226 bp; exon 7, 123 bp; Panel B, control, 659 bp (chromosome 1 genomic sequence about 90,000 bp 5' of Rhesus box); intron 7, 390 bp; RHD(W16X), 248 bp; RHDΨ, 154 bp. The internal control amplicons, which were devised to be larger than the specific amplicons, may be suppressed because of competition, if a specific product is amplified.

The Sequence Listing submitted herewith electronically is incorporated herein by reference.

The examples illustrate the invention:

EXAMPLE 1

Blood Samples and DNA Isolation

EDTA- or citrate-anticoagulated blood samples were collected from white blood donors and characterized as D negative in routine typing including an antiglobulin test with anti-D (Wissenschaftlicher Beirat der Bundesärztekammer; Paul-Ehrlich-Institut. Richtlinien zur Blutgruppenbestimmung und Bluttransfusion (Hämotherapie). Köln: Deutscher Ärzte-Verlag; 1996; Wagner, Infusionsther Transfusionsmed 22:285-90, 1995). If necessary, samples were collected at random for specific CcEe phenotypes. A total of 314 ccddee, 433 Ccddee, 271 ccddEe, 19 CcddEe, 24 CCddee, 1 CcddEE and 6 ccddEE samples were tested. DNA was isolated by a modified salting-out procedure as described in Gassner et al, Transfusion 37; 1020, 1997.

EXAMPLE 2

Molecular Work-Up

All samples were tested by PCR-SSP for the presence of four different RHD specific polymorphisms located in the RHD promoter, intron 4, exon 7 and the 3' untranslated region of exon 10. 48 samples with at least one positive PCR reaction were detected (Table 5). Those samples were further investigated for the presence of RHD specific polymorphisms in exon 3, exon 4, exon 5, exon 6, exon 7, intron 7 and exon 9. Twenty-six samples showed one of eight distinct PCR patterns involving a mixture of positive and negative reactions (Table 6). Twenty-two samples were positive for all RHD specific polymorphisms investigated and were assigned to eight RHD alleles by RHD specific sequencing of the ten RHD exons from genomic DNA (Table 7). For each PCR pattern and each RHD allele, one sample was serologically investigated. The phenotypes were determined to represent weak D, partial D, and D$_{el}$, or confirmed as serologically D negative by adsorption/elution (Table 6 and 7).

EXAMPLE 3

DNA Database Searches and Analysis

The GenBank and the chromosome 1 database of the Sanger Center were searched with cDNA sequences representative of RHD (RhXIII, accession number X63097) and RHCE (RhVI, X63095) using the BLAST program. The 84,810 by genomic clone dJ469D22 (GenBank accession number AL031284), the 129,747 by genomic clone dJ465N24 (GenBank accession number AL031432) and the 2,234 by SMP1 cDNA (GenBank accession number AF081282) were identified. dJ469D22 represented a major fragment of the RHCE gene, starting 33,340 by 5' of the RHCE start codon and ending 1,142 by 3' of exon 9. In dJ465N24, an internal stretch of 1,418 by located between position 120,158 and 121,568 was 96% homologous to the 3' end of the RHD cDNA. The 3' end of the SMP1 cDNA was complementary to the 3' end of the RHCE cDNA with an overlap of 58 bp.

EXAMPLE 4

PCR

If not mentioned otherwise, PCR reactions were done with 60° C. annealing, 10 min extension at 68° C. and denaturation at 92° C. using the expand long template or the expand high fidelity PCR systems (Boehringer Mannheim, Mannheim, Germany) and the listed primers (Table 1) (SEQ ID NOS 28-66). Three PCR reactions were used to bridge gaps in the 3' flanking regions of the RH genes. PCR 1 was done using primers real and rend31 (PCR 2, rend32, sf1c; PCR 3, rea7, sf3). The structure of the 5' flanking regions was confirmed with PCR amplifications involving sense primers rend32, rey14a, rey15a and antisense primers re011d and re014. Intron 9 size was estimated to be about 9,000 bp based on PCR amplifications using rb10b and rr4 for RHD (re96 and rh7 for RHCE).

EXAMPLE 5

Nucleotide Sequencing

Nucleotide sequencing was performed with a DNA sequencing unit (Prism BigDye terminator cycle-sequencing ready reaction kit; ABI 373A, Applied Biosystems, Weiterstadt, Germany).

EXAMPLE 6

Characterizing the RH Gene Locus

A physical structure of the RH genes' locus was derived (FIG. 1). This structure was deduced from the following considerations: (i) 3' flanking regions. The 3' flanking region of RHD was highly homologous to the 3' part of dJ465N24 (FIG. 1B, region c). This homology continued beyond the end of the RHD cDNA and extended for at least 8,000 by as proven by the fact that it was possible to obtain PCR amplicons (FIG. 1B, PCR 1). Sequences homologous to the 3' part of dJ465N24 were neighboring to the 5' region of the SMP1 gene (FIG. 1B; PCR 2). The 3' end of the SMP1 gene occurred immediately adjacent to the RHCE gene as indicated by the complementarity of the 3' ends of the respective cDNAs and confirmed by PCR (FIG. 1B, PCR 3). Further details of the RHD 3' flanking region (Rhesus box) and the SMP1 gene are described below. (ii) 5' flanking regions. dJ469D22 comprised 33,340 by 5' flanking region of RHCE. For RHD, a 466 by homology between the 3' end of dJ465N24 and dJ469D22 indicated that dJ465N24 might represent the 5' flanking sequence of RHD. This assumption was proven by PCR (FIG. 2). (iii) Analysis of YAC 38A-A10. DNA from the YAC 38A-A10 (UK HGMP resource centre, Cambridge, UK) was isolated after a single growth phase by standard methods. It was confirmed that this YAC contained RH DNA. Furthermore, shotgun cloning experiments indicated that some of its insert probably derived from the X chromosome (data not shown). This YAC had been known to contain RHCE exons 2 to 10 and RHD exons 1 to 10 (Garritt, Hum. Mol. Genet. 6:843, 1997) and was thus expected to contain the DNA segments interspersed between RHD and RHCE. The presence of DNA segments representative of different parts of the RH locus in this YAC was observed (Table 2). The results were concordant with the proposed structure of the RH locus shown in FIG. 1, Panel A.

EXAMPLE 7

Identification of RHD Specific Sequences in the RHD Promoter

About 2,000 bp RHD promoter sequence was established by chromosomal walking (GenomeWalker kit, Clontech, Heidelberg, Germany). D-positive and D-negative samples were amplified using primers re04 and re11d (Table 1) (SEQ ID NOS 28-66) and RHD- and RHCE-specific sequences established for 1,200 bp 5' of the start codon by sequencing with internal primers. A short deletion in the RHD gene was identified and used to develop the RHD-specific primer re011d. The 1,200 bp sequence including the RHD promoter has been deposited at EMBL under accession no. AJ252314.

EXAMPLE 8

Characterization of Rhesus Boxes

Two DNA segments of about 9,000 bp, located 5' and 3' of the RHD gene, were highly homologous, had identical orientation, and were designated "Rhesus boxes" (FIG. 4). The Rhesus boxes were amplified and sequenced using internal primers in two overlapping fragments using PCR primer pairs rez4/rend31 and rend32/re011d (upstream Rhesus box), real/rend31 and rend32/sr9 (downstream Rhesus box), and rez4/rend31 and rend32/sr9 (hybrid Rhesus box of RHD-negative). The upstream Rhesus box (5' of RHD) was about 9,142 bp long and ended about 4,900 bp 5' of the RHD start codon. The downstream Rhesus box (3' of RHD) was 9,145 bp long and started 104 bp after the RHD stop codon. The Rhesus boxes exactly embraced the part of RHD with homology to RHCE. The central portion of both Rhesus boxes contained an almost complete remnant of a transposon-like human element (THE-1B). The single open reading frame usually found in the THE-1B element was, however, abolished due to several nucleotide aberrations occurring in both Rhesus boxes in parallel, including a nonsense mutation in codon 4. While there was overall 98.6% homology between both Rhesus boxes, a 1,463 bp "identity region" located between positions 5,701 and 7,163 was completely identical with the single exception of a 4 bp T insertion in a poly T tract.

EXAMPLE 9

Evaluation of the Genomic Structure of SMP1

The genomic structure of the SMP1 gene was evaluated by PCR using internal primers and nucleotide sequencing (FIG. 3). The sizes of the SMP1 introns were estimated by PCR amplicons obtained with primers rend32, sr9, sf1c, sf1, sm19, sr45, sr47, sr47c, sr5, sr5c, sr55, sr55c, sr3, sr3 kp, real. The positions of the intron/exon junctions and the absence of additional introns were determined by nucleotide sequencing. Six introns could be identified. Exon 1 contained 5' untranslated sequences only and was separated from the Rhesus box by 15 bp. The long 3' untranslated sequence of exon 7 overlapped with RHCE exon 10. The total gene size was estimated to be 20,000 bp resulting, in conjunction with the downstream Rhesus box, in a distance between RHD and RHCE of about 30,000 bp (FIG. 1).

EXAMPLE 10

Localization of the RHD Gene Deletion in the RHD Negative Haplotypes

It was reasoned that the homology of the two Rhesus boxes may have been instrumental for the mechanism of the RHO deletion in the common RHO negative haplotypes. The nucleotide sequence of the Rhesus box in RHD negative DNA was determined (FIG. 5). The single Rhesus box detected in RHO negatives had a hybrid structure. The 5 end of this Rhesus box represented a upstream Rhesus box, the 3' end a downstream Rhesus box. It was determined that the 903 bp breakpoint region of the RHO deletion was located in the identity region of the Rhesus boxes (FIG. 4, Identity Region).

EXAMPLE 11

Specific Detection of the RHD Deletion by PCR

Two PCR based methods were developed for specific detection of the RHD gene deletion occurring in the prevalent RHD negative haplotypes (FIG. 6). Long-range PCR-SSP was performed using the expand long template PCR system with buffer 3 and primers rez4 (5' of upstream Rhesus box) and sr9 (SMP1 exon 1). Annealing was at 60° C. and extension 20 min at 68° C. PCR amplicons were resolved using a 1% agarose gel. PCR-RFLP was performed using the expand high fidelity PCR system and primers rez7 (non-specific, 5' of Rhesus box identity region) and mb31 (specific for downstream Rhesus box, 3' of Rhesus box identity region). Annealing was at 65° C. and extension 10 min at 68° C. PCR amplicons were digested with PstI for 3 hrs at 37° C. and fragments resolved using a 1% agarose gel.

These techniques allowed the ready and direct detection of the common RHD negative haplotypes, even if they are in trans to RHD positive haplotypes. PCR-RFLP was further applied to a larger number of samples (Table 3). As expected, all 33 samples with known genotype were correctly typed. In 68 additional samples representative of the most common phenotypes, the results were consistent with the known haplotype frequencies in the population.

EXAMPLE 12

RHD PCR-SSP

The PCR-SSP reactions (Table 4) were adapted and extended from a previously described RHD exon specific PCR-SSP method (Gassner, Transfusion 37:1020-6, 1997) and were triggered to work under identical thermocycling conditions. Concentrations of specific primers were 0.2 µM for all reactions with the exception of exon 6 (0.1 µM), intron 7 (0.4 µM) and exon 9 (0.4 µM). For most samples intron 4/exon 7 was tested as multiplex reaction containing 0.2 µM of axon 7 (primer set ga71/ga72) and 0.1 µM of intron 4 primers. Each reaction contained a set of HGH primers (Gassner, Transfusion 37:1020-6, 1997) as an internal control in concentrations of 0.05 µM for promoter, intron 4, and exon 7 with ga71/ga72; 0.075 µM for exon 10; 0.1 µM for intron 7; 0.15 µM for exon 3, exon 4, exon 7 with rb26/re71, and exon 9; 0.2 µM for exon 5 and exon 6. $Mg^{2+}$ concentration was 0.4 µM for intron 7 and for all other reactions 0.15 µM. For exon 6, 20% solution Q (Qiagen, Hilden, Germany) was added.

EXAMPLE 13

Improved RHD PCR-SSP for Routine DNA Typing

Based on the alleles detected in this study and described previously, we devised an improved RHD PCR-SSP for routine DNA typing that included the specific detection of RHDΨ and alleles detected in this study, like RHD(W16X) in a single PCR tube. Reaction A contained primers ga71 and ga72 at 0.3 µM, rb12 and re41 at 0.1 µM, and HGH primers at 0.1 µM. Mg2+ was at 0.175 µM. Reaction B contained primers RhPsiF and RhPsiB at 0.5 µM, re11d and RhX1f1 at 0.3 µM, re721 and rb9 at 0.2 µM and as control primers rend9b1 and rend 9b2 at 0.2 µM. Primer sequences were ga71, gttgtaaccgagtgctggggattc; ga72, tgccggctccgacggtatc; rb12, tcctgaacctgctctgtgaagtgc; re41, cgatacccagtttgtctgccatgc; RhPsiF, agacagactaccacatgaacttac; RhPsiB, tctgatctttatcctcgttccctc; re11d, agaagatgggggaatctttttcct; RhX1f1, cgctgcctgcccctctga; re721, ctggaggctctgagaggttgag; rb9, aagctgagttccccaatgctgagg; rend9b1, cactgcacttggcaccattgag; rend9b2, ttccgaaggctgcttttccc.

The PCR reactions could be performed in two tubes (FIG. 15), tested five polymorphisms and were expected to have a false-positive rate of less than 1:10,000 (Table 11).

EXAMPLE 14

PCR Reactions for $Cde^s$

A hybrid exon 3 with a N152T substitution occurring in the $Cde^s$ haplotype was detected by a PCR-SSP reaction using specific primers Rh152Tb and ga31 at 0.3 µM. The L245V substitution observed in $Cde^s$ was detected with specific primers Rh223Vf and Rh245Vb at 0.2 µM. HGH primer concentrations were 0.1 µM. The other PCR conditions were identical as described in the previous paragraph. Primers sequences were Rh152Tb, gatattactgatgaccatcctcatgg; Rh223Vf, ttgtggatgttctggccaagtg; and Rh245Vb, gctgtcaccactctgactgctac. The $Cde^s$ haplotype, that is frequent in Africans (Faas, Transfusion 37:38-44, 1997; Singleton, Blood 95:12-8, 2000), possesses a hybrid exon 3 harboring the RHCE specific N152T substitution (Faas, Transfusion 37:38-44, 1997). This hybrid exon is expected to be typed as RHD positive by the RHD exon 3 specific PCR that detected an A at position 383 (codon 128) and was used in the population survey. Since pattern 4 and pattern 8 were compatible with the known data about the $Cde^s$ haplotype, the presence of a hybrid exon 3 was evaluated in the two samples by sequencing the 3' part of exon 3 and by a PCR-SSP specific for an exon 3 hybrid indicative of $Cde^s$. The pattern 4 sample possessed a normal RHD exon 3, while the pattern 8 sample had a hybrid exon 3 as predicted for a $Cde^s$ haplotype. Also, the T at position 410 (A137V substitution) typical for the $Cde^s$ haplotype (Daniels, Transfusion 38:951-8, 1998) and also present in D category III type IV was detected. The identity of pattern 8 and $Cde^s$ was further corroborated by a PCR-SSP detecting G at position 733 (L245V substitution).

EXAMPLE 15

5' Breakpoint Region of Cde$^s$ in Intron 3

Based on its cDNA, Cde$^s$ had been characterized as an RHD-CE(3-7)-D hybrid gene, in which the 5' part of exon 3 derived from RHD and the 3' part of exon 3 including codon 152 derived from RHCE. We noted that a similar hybrid exon 3 with a N152T substitution was found in D category III type IV (Wagner, F. F., Frohmajer, A., Ladewig, B., Eicher, N. I., Lonicer, C. B., Müller, T. H., Siegel, M. H., and Flegel, W. A. Weak D alleles express distinct phenotypes. *Blood* 95:2699-2708, 2000) and in D category IVa (Rouillac, C., Colin, Y., Hughes-Jones, N. C., Beolet, M., D'Ambrosio, A.-M., Cartron, J. P., and Le Van Kim, C. Transcript analysis of D category phenotypes predicts hybrid Rh D-CE-D proteins associated with alteration of D epitopes. *Blood* 85:2937-2944, 1995), two aberrant AHD alleles in which exons 4 to 7 derived from RHD. We reasoned that the N152T substitution might have antedated the substitution of RHD exons 4 to 7 in Cde$^s$. In this case, the 5' breakpoint region was expected to be located in intron 3 rather than exon 3 as predicted from the cDNA. We hence evaluated the presence of RHD specific polymorphisms in Cde$^s$ intron 3.

To evaluate the presence of the EcoRV-site at nucleotide position 752 (RHD specific) and 2872 (RHCE specific) and of the PvuII-site at nucleotide position 1777 (RHCE specific), the 5' part of intron 3 of RHD and RHCE was amplified using primers rb3 and rb33 and digested with EcoRV or PvuII. To evaluate the presence of the Sad-site at nucleotide position 7797 (RHCE specific) and of the AIw44I-site at nucleotide position 8550 (RHD specific), the 3' part of intron 3 of RHD and RHCE was amplified using primers rb34 and rb5 and digested with Sad or AIw44I. Primer sequences were rb3, aaggtcaacttggcgcagttggtgg; rb33, gtgagactgagttctgtattctgg; rb34, ccagaatacagaactcagtctcac; rb5, ggcagacaaactgggtatcg-ftgc.

The PCR-RFLP analysis of these intron 3 polymorphisms indicated that RHD specific sequences were present at least up to intron 3 position 2872. To further determine the 5' breakpoint region of Cde$^s$, we sequenced a DNA stretch encompassing the breakpoint region. DNA was amplified using primers rb3 and re37 and sequenced using primers rb33, rb34 and Cdesf1. Primer sequences were re37, gggttaaagtcacatacacagatg; Cdesf1, atacagaactcagtctcacaacttag. We determined that the breakpoint region was located in intron 3 as shown in FIG. 12.

EXAMPLE 16

3' Breakpoint Region of Cde$^s$ in Intron 7

To determine the 3' breakpoint region of Cde$^s$ in intron 7, we sequenced parts of intron 7. DNA was amplified using sense primers rb8, re77 and rex1 and antisense primers rb51 and re711b. Primers rb43, rex19c, cdes7b2, and cdes7f2 were used for nucleotide sequencing. Primer sequences were rb8, gtgttgtaaccgagtgctgggg; re77, tctccacagctccatcatggg; rex1, ggctgtaaaaatggctgaagcag; rb51, gcatgacgtgttctgcctcttg; re711b, ctatcagcattctgatctcaacg; rb43, gaatagcagagaaaacct-cagactgcc; rex19c, gctccattcttgacaatacaggc; cdes7b2, gct-tatactatataagttgggttttttgg; cdes7f2, gtttgaatcccaagagccactcat. We established the breakpoint region as shown in FIG. 13. The structure of the 3' breakpoint region was intriguing, because there were multiple switches between RHCE and RHD specific sequences. Those features are unusual for a breakpoint region and may be used for specific diagnosis of Cde$^s$. They may indicate that the parental alleles differed from the standard RHCE and RHD sequences or that after the major gene conversion, additional small gene conversions were introduced.

EXAMPLE 17

A PCR-SSP to Specifically Detect Cde$^s$

Usually, the presence of Cde$^s$ is identified by the RHD-CE-D hybrid pattern in an RHD exon specific PCR. Such an approach does not allow the specific detection of the D negative Cde$^s$ haplotype, if an RHD positive haplotype occurs in trans. Since Cde$^s$ does not contain a hybrid Rhesus box, a RHD/Cde$^s$ heterozygous person is likely mistyped as RHD$^+$/RHD$^+$ homozygous. There are several distinct features of Cde$^s$ in the promoter, intron 2, exon 2, and exon 3 that might be used for a specific detection. These features are, however, shared by the D positive alleles D category IVa and partially by D category III type IV, which would hence confound such methods of detection.

Based on the Cde$^s$ specific DNA sequence in intron 7, we developed a PCR-SSP that specifically detected Cde$^s$. The 3' breakpoint region of Cde$^s$ in intron 7 was detected by PCR-SSP using specific primers Cdes7f2 and Cdes7b2 at 0.4 µM and HGH control primers at 0.15 µM. The other PCR conditions were identical as described in example 12. Primer sequences were Cdes7f2, gtttgaatc-ccaagagccactcat; Cdes7b2, gcttatactatataagttgggttttttgg. We obtained a specific product with the index Cde$^s$ sample (FIG. 14), two additional Cde$^s$ samples and a RHDΨ/Cde$^s$ heterozygous sample (FIG. 14). Normal RHD positive and RHD negative samples as well as samples of D category III type IV and of D category IVa did not result in a specific PCR product (FIG. 14). We concluded that our PCR-SSP method allowed a specific detection of Cde$^s$, even if it occurred in trans to another RHD positive allele. Furthermore, the detection method was not confounded by D category III type IV or D category IVa that shared the N152T substitution with Cde$^s$. It should be noted that the latter haplotypes are frequent in populations comprising African ethnic background, in which Cde$^s$ is prevalent. The method described by us in this example allowed the specific detection of Cde$^s$, is not confounded by the other haplotypes and hence represents a considerable improvement to the prior art. Our characterization of the 5' breakpoint region (example 15) will likewise allow the specific detection of Cde$^s$ by any suitable method known in the art, like PCR-SSP, PCR-LP, PCR-RFLP, PCR-SSO, Southern blotting etc.

The specific detection of Cde$^s$ is also important for the correct prediction of the antigen C. The RHD gene of Cde$^s$ encodes for an antigen C that is often missed in DNA based methods for the prediction of antigen C.

EXAMPLE 18

Immunohematology

One sample of each RHD positive allele was evaluated by direct agglutination with two monoclonal anti-D (Seraclon anti-D, clone BS226; Biotest, Dreieich, Germany, and Frekakion anti-D, clone MS201; Gull, Bad Homburg, Germany). Indirect antiglobulin test was done in a gel matrix test (LISS-Coombs 37° C., DiaMed-ID Micro Typing System, DiaMed, Cressier sur Morat, Switzerland) using an oligoclonal anti-D (Seraclon anti-D blend, clones H41 11B7, BS221 and RS232; Biotest). Samples reactive in gel matrix technique were further investigated using the monoclonal anti-D HM10, HM16, P3x61, P3x35, P3x212 11F1, P3x212 23B10, P3x241, P3x249, P3x290 (Diagast, Loos, France) and H41 11B7 (Biotest). The presence of a $D_{el}$ phenotype was determined by adsorption of 500 µl of a polyclonal anti-D (Human incomplete anti-D; Lorne Laboratories, Reading, UK) to 500 µl red cells for 1 h at 37° C. and elution using a chloroform technique (Flegel, Transfusion 40:428-434, 2000). The analysis of samples routinely grouped as D negative revealed 16 $D_{el}$ samples and 3 D positive samples with weak or partial D. These samples clustered among samples previously believed to be D negative with a C or E (Table 9). Nineteen of twenty-seven discrepancies between routine serology and a PCR testing intron 4 and exon 7 represented D positive samples missed by serology, only eight were due to false-positive PCR.

EXAMPLE 19

Haplotype Frequencies

For alleles observed more than once, their haplotype association was trivial. Alleles that were observed only once were assumed to be associated with the Cde or cdE haplotype rather than the cde haplotype, because no RHD positive allele was detected in any ccddee sample. An allele occurring in a single CcddEe sample was formally counted half for Cde and half for cdE. CCddee samples were assumed to harbour one aberrant and one normal Cde allele. The frequency of a given aberrant RHD allele in its haplotype was calculated as the number of observed samples divided by the number of the corresponding haplotypes under observation (500 Cde, 302 cdE). The population frequency of an RHD allele was calculated from the frequency of this allele in its haplotype and the known frequency of the haplotype in the local population (Wagner, Infusionsther. Transfusionsmed. 22:285-90, 1995). The haplotype frequencies were calculated for each PCR pattern and for each RHD allele (Table 8). In accordance with a previous study in England by Avent et al. (Avent, Blood 89:2568-77, 1997), 4.9% of Cde haplotypes and 1.5% of cdE haplotypes were RHD positive in our population. As no RHD positive allele was detected among 314 ccddee samples, the frequency in the cde haplotype was less than 0.5% (upper limit of one-sided 95% confidence interval, Poisson distribution). The three frequencies differed statistically significantly from each other (p<0.05; two sided Fisher's exact test for each pairwise comparison corrected according to Bonferoni-Holm). The population frequency of any D negative RHD positive haplotype was estimated to be 1:1,606. $D_{el}$ alleles could only be observed in the presumed Cde haplotypes. About 3% of samples carrying antigen C that were typed D-negative in the blood bank routine represented D. The population frequency of $D_{el}$ alleles was 1:3,030.

TABLE 1

Primers

| Primer | Nucleotide sequence | Localization | Position |
|---|---|---|---|
| rb10b | ggctaaatattttgatgaccaagtt | RHD cDNA | 1,194 to 1,217 (SEQ ID NO: 28) |
| re011d | gcagccaacttcccctgtg | RHD promoter | −883 to −901 (SEQ ID NO: 29) |
| re014 | gctctaccttggtcacctcc | dJ469D22 | 52,189 to 52,209 (SEQ ID NO: 30) |
| re04 | aggtcacatccatttatcccactg | dJ469D22 | 53,968 to 53,945 (SEQ ID NO: 31) |
| re11d | agaagatgggggaatcttttttcct | dJ469D22 | 51,193 to 51,216 (SEQ ID NO: 32) |
| re96 | ttgtgactgggctagaaagaaggtg | dJ469D22 | 242 to 216 (SEQ ID NO: 33) |
| rea7 | tgttgcctgcatttgtacgtgag | RHD cDNA | 1,311 to 1,333 (SEQ ID NO: 34) |
| rend31 | ttctgtctggggttggggaggg | dJ465N24 | 128,649 to 128,629 (SEQ ID NO: 35) |
| rend32 | ggaggggttaatatgggtggc | dJ465N24 | 127,355 to 127,375 (SEQ ID NO: 36) |
| rend8b1 | tttgtcctggttgcctgtggtc | dJ465N24 | 69,296 to 69,274 (SEQ ID NO: 37) |
| rend8b2 | caaatcctgttgactggtctcgg | dJ465N24 | 68,451 to 68,473 (SEQ ID NO: 38) |
| rend9a1 | aacggctccatcaccccctaaag | dJ465N24 | 50,008 to 49,987 (SEQ ID NO: 39) |
| rend9a2 | cccactcctagataccaacccaag | dJ465N24 | 49,059 to 49,083 (SEQ ID NO: 40) |
| rey14a | ctttatgcactgcctcgttgaatc | dJ469D22 | 56,792 to 56,769 (SEQ ID NO: 41) |
| rey14b | ttgactggtgtggttgctgttg | dJ469D22 | 55,863 to 55,884 (SEQ ID NO: 42) |
| rey15a | gcagaaaggggagttgatgctg | dJ469D22 | 55,416 to 55,395 (SEQ ID NO: 43) |
| rey7 | ctgacaaagttgagagcccactg | dJ469D22 | 62,324 to 62,346 (SEQ ID NO: 44) |
| rey8 | ttaagcctacatccacatgctgag | dJ469D22 | 62,854 to 62,831 (SEQ ID NO: 45) |
| rez2 | ccttggtctgccagaatttttca | RHD cDNA | 2738 to 2717 (SEQ ID NO: 46) |
| rez4 | gtttggcatcataggagatttggc | dJ465N24 | 120,101 to 120,124 (SEQ ID NO: 47) |
| rez7 | cctgtccccatgattcagttacc | dJ465N24 | 124,831 to 124,854 (SEQ ID NO: 48) |
| rh7 | acgtacaaatgcaggcaac | RHD cDNA | 1,330 to 1,312 (SEQ ID NO: 49) |
| mb31 | cctttttttgtttgtttttggcggtgc | downstream Rhesus box | 6,710 to 6,684 (SEQ ID NO: 50) |
| rr4 | agcttactggatgaccacca | RHD cDNA | 1,541 to 1,522 (SEQ ID NO: 51) |
| sf1 | gactgggggaaaagcgcaatac | SMP1 cDNA | 142 to 164 (SEQ ID NO: 52) |
| sf1c | gtattgcgcttttcccccagtc | SMP1 cDNA | 164 to 142 (SEQ ID NO: 53) |
| sf3 | tgacttgctctcatcccacatg | SMP1 cDNA | 1,696 to 1,717 (SEQ ID NO: 54) |
| sm19 | gggcttgaagcaagtaaatggaag | SMP1 intron 1 | −58 to −35 (SEQ ID NO: 55) |
| sr1 | gctatcaatattttcttggttacagacac | SMP1 cDNA | 2,172 to 2,144 (SEQ ID NO: 56) |
| sr3 | gttcactgccataagtcttcagtgc | SMP1 cDNA | 575 to 551 (SEQ ID NO: 57) |
| sr3kp | tggccgcactgaagacttatgg | SMP1 cDNA | 546 to 567 (SEQ ID NO: 58) |
| sr45 | cagctgcatctatgataatccacc | SMP1 cDNA | 224 to 243 (SEQ ID NO: 59) |
| sr47 | atggacaagtccgaggtgatag | SMP1 cDNA | 315 to 344 (SEQ ID NO: 60) |
| sr47c | atcacctcggacttgtccattc | SMP1 cDNA | 342 to 321 (SEQ ID NO: 61) |
| sr5 | gcaatcagagatccaaaggccaac | SMP1 cDNA | 428 to 405 (SEQ ID NO: 62) |
| sr5c | gttggcctttggatctctgattgc | SMP1 cDNA | 405 to 428 (SEQ ID NO: 63) |
| sr55 | gacatagtatacccctggaattgctgt | SMP1 cDNA | 472 to 497 (SEQ ID NO: 64) |

TABLE 1-continued

Primers

| Primer | Nucleotide sequence | Localization | Position |
|---|---|---|---|
| sr55c | acagcaattccagggtatactatgtc | SMP1 cDNA | 497 to 472 (SEQ ID NO: 65) |
| sr9 | ctcccccgattttagccaagaa | SMP1 cDNA | 27 to 6 (SEQ ID NO: 66) |

For the RHD promoter and the RHD cDNA, the positions refer to the distance from the A of the start codon. For introns, they refer to the distance from the intron/exon junction. For all other sequences including the SMP1 cDNA, they refer to the distance from the start of the published sequences. The mismatches in primers rey14b, mb31, and sf3 were inadvertently introduced. Primers re11d, re014 and re04 do not exactly match dJ469D22, because they were designed from our raw sequences covering the 5' flanking region of RHD.

TABLE 2

Presence of RHD flanking sequences in the YAC 38A-A10

| Primer | | | | Amplicons obtained with | | |
|---|---|---|---|---|---|---|
| | | | | Genomic DNA | | YAC |
| sense | antisense | Predicted position | Amplicon size | RHD⁺ | RHD⁻ | 38A-A10 |
| rend9a1 | rend9a2 | RHD 5' flanking region | about 85,000 bp from ATG | 948 bp | yes | yes |
| rend8b1 | rend8b2 | RHD 5' flanking region | about 50,000 bp from ATG | 845 bp | yes | yes |
| rea7 | rez2 | RHD 3' flanking region | about 1,500 bp from STOP | 1,412 bp | yes | no |
| rend32 | sr9 | RHCE 3' flanking region | about 20,000 bp from STOP | 1,989 bp | yes | yes |
| sr1 | sf3 | RHCE 3' flanking region | about 1,000 bp from STOP | 477 bp | yes | yes |
| rey14b | rey14a | RHCE 5' flanking region | about 5,300 bp from ATG | 929 bp | yes | yes |
| rey7 | rey8 | RHCE 5' flanking region | about 10,000 bp from ATG | 530 bp | yes | yes |

TABLE 3

PCR-RFLP for the specific detection of the RHD deletion

| | | Samples tested (n) | Number of samples with RHD genotype determined | | | expected* | | | P¶ |
|---|---|---|---|---|---|---|---|---|---|
| Phenotype | Known genotype | | +/+ | +/− | −/− | +/+ | +/− | −/− | |
| Known genotype | | | | | | | | | |
| ccddee | cde/cde | 14 | 0 | 0 | 14 | 0 | 0 | 14 | N.A. |
| CCddee | Cde/Cde† | 5 | 0 | 0 | 5 | 0 | 0 | 5 | N.A. |
| ccddEE | cdE/cdE† | 1 | 0 | 0 | 1 | 0 | 0 | 1 | N.A. |
| D variants | D/cde‡ | 9 | 0 | 9 | 0 | 0 | 9 | 0 | N.A. |
| ccDEe | cDe/cDE§ | 4 | 4 | 0 | 0 | 4 | 0 | 0 | N.A. |
| Common phenotypes | | | | | | | | | |
| CcDee | | 10 | 1 | 9 | 0 | 0.5 | 9.5 | 0 | >0.4 |
| ccDEe | | 10 | 0 | 10 | 0 | 0.3 | 9.7 | 0 | >0.5 |
| ccDee | | 10 | 1 | 9 | 0 | 0.5 | 9.5 | 0 | >0.4 |
| CCDee | | 10 | 9 | 1 | 0 | 9.5 | 0.5 | 0 | >0.4 |
| CcDEe | | 12 | 11 | 1 | 0 | 11 | 1 | 0 | >0.5 |
| ccDEE | | 10 | 10 | 0 | 0 | 9.2 | 0.8 | 0 | >0.4 |
| CCDEe | | 6 | 5 | 1 | 0 | 5.8 | 0.2 | 0 | >0.1 |

*Expected number of RHD⁺/RHD⁺ and RHD⁺/RHD⁻ samples based on known genotypes or the haplotype frequencies in the local population⁴¹
†RHD-negative in PCR.
‡RHD⁺/RHD⁻, because a weak or partial D phenotype would be masked in a RHD⁺/RHD⁺ gentoype. These samples were weak D type 1 (n = 2), type 2 (n = 2), type 3 (n = 2), type 4 (n = 2) and D^{III} (n = 1).
§Presence of two RHD genes differing in their polymorphic HaeIII-site in intron 3⁴² demonstrated by PCR-RFLP.
N.A.—not applicable. Probabilities were calculated based on confidence limits of binomial distribution.

TABLE 4

RHD PCR-SSP

| Region | Name* Reference | DNA sequence | Position | Poly- morphisms detected | Amplicon size |
|---|---|---|---|---|---|
| Promoter | re012 | tccactttccacctccctgc | Promoter −1,137 to −1,119 | 7 bp deletion at −1125 | 255 |

TABLE 4-continued

RHD PCR-SSP

| Region | Name* Reference | DNA sequence | Position | | Poly-morphisms detected | Amplicon size | |
|---|---|---|---|---|---|---|---|
| | re011d | gcagccaacttccctgtg | Promoter | −883 to −901 | 4 bp deletion at −896 | | 44 |
| Exon 3 | ga31 (D-3-383) | ttgtcggtgctgatctcagtgga | Exon 3 | 361 to 383 | 383 A | 154 | 21 |
| | rb21 | aggtccctcctccagcac | Intron 3 | 28 to 11 | | | 42 |
| Exon 4 | ga41 (D-4-527) | acatgatgcacatctacgtgttcgc | Exon 4 | 503 to 527 | | 123 | 21 |
| | ga42 (D-4-602) | cagacaaactgggtatcgttgctg | Exon 4 | 625 to 602 | 602 C | | 21 |
| Intron 4 | re41 this study | cgatacccagtttgtctgccatgc | Exon 4 | 608 to 631 | | 226 | |
| | rb12 | tcctgaacctgctctgtgaagtgc | Intron 4 | 198 to 175 | Intron 4 deletion in RHD | | 40 |
| Exon 5 | rb24 | agacctttggagcaggagtg | Intron 4 | −53 to −34 | | 228 | 40 |
| | ga51 (D-5-787) | ctgctcaccttgctgatcttccc | Intron 5/ Exon 5 | 8 to 787 | 787 G | | 21 |
| Exon 6 | ga62 (D-6-826) | ttatgtgcacagtgcggtgttgg | Exon 6 | 804 to 826 | | 133 | 21 |
| | ga61 (D-6-916) | caggtacttggctcccccgac | Exon 6 | 936 to 916 | 916 G | | 21 |
| Exon 7† | ga71 (D-7-967) | gttgtaaccgagtgctggggattc | Exon 7 | 944 to 967 | | 123 | 21 |
| | ga72 (D-7-1048) | tgccggctccgacggtatc | Exon 7 | 1,066 to 1,048 | 1,048 G | | 21 |
| Exon 7† | rb26 | aggggtgggtagggaatatg | Intron 6 | −62 to −43 | | 130 | 42 |
| | re71 | acccagcaagctgaagttgtagcc | Exon 7 | 1,008 to 985 | 985/986 GG | | 42 |
| Intron 7 | rb52 | ccaggttgttaagcattgctgtacc | Intron 7 | 6,666 to 6,690 | 6,690 C | | 42 |
| | rb51 this study | gcatgacgtgttctgcctcttg | Intron 7 | 6,734 to 6,713 | 6,713 C | 169 | |
| Exon 9 | re83 | gagattaaaaatcctgtgctcca | Intron 8 | −56 to −34 | | 119 | 42 |
| | re94 this study | cttggtcatcaaaatatttagcct | Exon 9 | 1,216 to 1,193 | 1,193 A | | |
| Exon 10 (3' UTR) | rea7 | tgttgcctgcatttgtacgtgag | 3'UTR | 1,310 to 1,333 | RHD/Rhesus box junction | 23 | 44 |
| | rr4 | agcttactggatgaccacca | 3'UTR | 1,541 to 1,522 | | | 42 |

*Primer names in brackets are as described by Gassner et al.[21].
†Primer set ga71/ga72 was used for the screening, primer set rb26-re71 for RHD exon specific PCR-SSP.

TABLE 5

Population survey of known D negative blood donors screened by RHD PCR-SSP

| Documented phenotype | Samples (n) screened | PCR-SSP positive* |
|---|---|---|
| ccddee | 314 | 0 |
| Ccddee | 433 | 34 |
| ccddEe | 271 | 5 |
| CCddee | 24 | 4 |
| CcddEe | 19 | 4 |
| ccddEE | 6 | 1 |
| CcddEE | 1 | 0 |
| Total | 1,068 | 48 |

*Positive for at least one of four RHD specific polymorphisms tested (promoter, intron 4, exon 7 or 3' UTR).

TABLE 6

PCR patterns compatible with RHD-RHCE-RHD hybrid genes or partial RHD deletions in 25 D negative samples

| PCR pattern | RHD specific PCR-SSP* | | | | | | | | | Possible cause[†] | Samples (n) | Phenotype | | Haplotype | Reference[‡] |
|---|---|---|---|---|---|---|---|---|---|---|---|---|---|---|---|
| | P | E3 | E4 | I4 | E5 | E6 | E7 | I7 | E9 | E10 | | Documented | Confirmed | | |
| Pattern 1 | + | − | − | − | − | − | − | − | − | + | RHD-CE(3-9)-D | 11 | Ccddee[§] | D negative | Cde | Whites[1,25], Africans[24] |
| Pattern 2 | + | − | − | − | − | − | − | − | + | + | RHD-CE(3-7)-D | 4 | Ccddee | D negative | Cde | this study |
| Pattern 3 | + | + | − | − | − | − | − | − | + | + | RHD-CE(4-7)-D | 3 | ccddEe | D negative | cdE | Whites[16] |
| Pattern 4 | + | + | − | − | − | − | − | + | + | + | RHD-CE(4-7)-D | 1 | CcddEe | D negative | n.k.[¶] | this study |
| Pattern 5 | + | + | − | − | − | + | + | + | + | + | RHD-CE(4-5)-D | 2 | ccddEe[α] | partial D/D$_{el}$[α] | cDE | Whites[3,22,30,40] |
| Pattern 6 | + | + | + | + | + | + | + | − | − | + | RHD-CE(8-9)-D | 3 | CCddee | D negative | Cde | Whites[21] |
| Pattern 7 | − | + | − | − | − | − | − | − | − | + | RHCE(1-9)-D(10) | 1 | ccddEe | D negative | cdE | this study |
| Pattern 8 | − | + | − | − | − | − | − | + | + | + | RHD(1-3)-CE(4-7)-D | 1 | CcddEe | D negative | Cde[β] | Africans[5,15] |

*P—Promoter, E3—Exon 3, E4—Exon 4, I4—Intron 4, E5—Exon 5, E6—Exon 6; E7—Exon 7; I7—Intron 7; E9—Exon 9; E10—Exon 10 (3′ UTR)
[†]Assuming the presence of a single RHD-CE-D hybrid allele.
[‡]Previously described alleles that fit PCR pattern and haplotype.
[§]11 samples: 9 Ccddee, 1 CCddee, 1 CcddEe
[¶]n.k.—not known.
[α]2 samples, 1 labeled CcddEe with D$_{el}$ phenotype, 1 labeled ccddEe with partial D D$^{VI}$ phenotype.
[β]Probably identical to Cde[s] (see below).

TABLE 7

RHD alleles with single nucleotide substitutions in 22 D negative samples

| Allele | Substitution | Effect(s) | Samples (n) | Phenotype Documented | Confirmed | Haplotype | Reference |
|---|---|---|---|---|---|---|---|
| RHD(W16X) | G->A at 48 | Stop codon at codon 16 | 2 | Ccddee | D negative | Cde | this study |
| RHD(G486(+1)A) | g->a at 486 + 1 | 5′ splice site intron 3 ACgt->ACat | 3 | Ccddee | D$_{el}$ | CDe | this study |
| RHD(G212V) | G->T at 635 | 3′ splice site intron 4 agGC->agTC | 1 | Ccddee | D negative | Cde | this study |
| RHD(C285Y) | G->A at 854 | Missense mutation G212V Missense mutation C285Y | 1 | ccddEe | partial D* | cDE | this study[1] |
| RHD(M295I) | G->T at 885 | Missense mutation M295I | 7 | Ccddee | D$_{el}$ | CDe[†] | 42 |
| RHD(Y330X) | C->G at 985 | Stop codon at codon 330 | 1 | Ccddee | D negative | Cde | this study |
| RHD(G1153(+1)A) | g->a at 1153 + 1 | 5′ splice site intron 8 AGgt->AGat | 1 | Ccddee | D negative | Cde | this study |
| RHD(G385A) | G->C at 1154 | 3′ splice site intron 8 agGT->agCT | 1 | CcddEe | weak D | cDE | 42 |
| RHD(K409K) | G->A at 1227 | Missense mutation G385A 5′ splice site intron 9 AGgt->AAgt | 5 | Ccddee | D$_{el}$ | CDe | this study |

*A detailed serologic analysis of this sample representing the partial D DIM has been published previously[43].
[†]The same allele occurring in a cDe haplotype has been described as weak D type 11.

TABLE 8

Estimated frequencies in population

| PCR pattern/Allele | Frequency among Cde/cdE | in population |
|---|---|---|
| Pattern 1 | 1:45 | 1:4,132 |
| Pattern 2 | 1:125 | 1:11,364 |
| Pattern 3 | 1:101 | 1:17,976 |
| Pattern 4 | 1:500* | 1:45,455* |
| Pattern 6 | 1:167 | 1:15,152 |
| Pattern 7 | 1:302 | 1:53,929 |
| Pattern 8 | 1:500 | 1:45,455 |
| RHD(W16X) | 1:250 | 1:22,727 |
| RHD(G212V) | 1:500 | 1:45,455 |
| RHD(Y330X) | 1:500 | 1:45,455 |
| RHD(G1153(+1)A) | 1:500 | 1:45,455 |
| Any D negative | 1:20/1:67[†] | 1:1,607 |
| RHD(G486(+1)A) | 1:167 | 1:15,152 |
| RHD(M295I) | 1:71 | 1:6,493 |
| RHD(K409K) | 1:100 | 1:9,091 |
| Any D$_{el}$ | 1:33[‡] | 1:3,030 |

*Assuming a Cde haplotype; a cdE haplotype would result in a frequency of 1:302 among cdE and 1:53,929 in the population. For statistics and sum frequencies, the haplotype was formally counted as 0.5 Cde and 0.5 cdE.
[†]1:20 among Cde, 1:67 among cdE.
[‡]1:33 relative to the Cde haplotype.

TABLE 9

False negative rate in routine typing for antigen D

| Documented Phenotype | Samples (n) | Confirmed phenotype (n) D$_{el}$ | partial or weak D | False negatives n | Rate |
|---|---|---|---|---|---|
| ccddee | 314 | 0 | 0 | 0 | 0%[†] |
| Ccddee | 433 | 15 | 0 | 15 | 3.5% |
| ccddEe | 271 | 0 | 2 | 2 | 0.7% |

TABLE 9-continued

False negative rate in routine typing for antigen D

| Documented Phenotype | Samples (n) | Confirmed phenotype (n) | | False negatives | |
|---|---|---|---|---|---|
| | | $D_{el}$ | partial or weak D | n | Rate |
| other* | 50 | 1 | 1 | 2 | 4% |
| D negative | N.A.‡ | 0.15% | 0.02% | | 0.17%† |

*CCddee, CcddEe, ccddEE, and CCddEe
†Upper limit of 95% confidence interval was 0.95% (Poisson distribution)
‡N.A.—not applicable. The frequencies are estimates based on the phenotype frequencies in the population[41].

TABLE 10

Previously described D negative, RHD positive alleles

| Allele | Haplotype | Population | Possible match |
|---|---|---|---|
| RHD(Q41X)[2] | Cde | Whites | not detected |
| RHD-CE(2-9)-D[1,24,25] | Cde | Whites[1,25], Blacks[24] | Pattern 1 |
| RHD-CE(3:455-7)-D[5,15] | Cde* | Blacks | Pattern 8 |
| RHD(488del4)[1] | Cde | Whites | not detected |
| RHD-CE(4-7)-D[16] | cdE | Whites | Pattern 3 or 4 |
| RHDΨ[38] | cde | Blacks | not detected |
| RHD(600del)[10] | Cde | somatic mutation* | not detected |
| RHD (exon 5 variant)[8] | cde | not communicated | not detected |
| RHD(G314V)[34] | Cde | Japanese | not detected |
| RHD(exon 9 variant) | Cde | Whites | Pattern 6 |

*Allele acquired by somatic mutation in a woman with chronic myelogenic leucemia and restricted to the myeloid lineage

TABLE 11

Population rates of false positives and positive predictive value of different RHD PCR strategies

| PCR strategy | Rate of false positives | Positive predictive value of positive result | Number of polymorphism tested |
|---|---|---|---|
| Exon 10 only | 1:1,275 | 0.999216 | 1 |
| Intron 4/Exon 7 | 1:4,081 | 0.999755 | 2 |
| Intron 4/Exon 7/RHDΨ | 1:4,700 | 0.999787 | 3 |
| Intron 4/Exon 7/W16X | 1:5,212 | 0.999808 | 3 |
| Intron 4/Exon 7/Intron 7 | 1:6,051 | 0.999835 | 3 |
| Exons 3, 4, 5, 6, 7, 9 | 1:6,051 | 0.999835 | 6 |
| Exons 2, 3, 4, 5, 6, 7, 9, 10 | 1:6,051 | 0.999835 | 8 |
| Intron 4/Exon 7/W16X/RHDΨ | 1:6,267 | 0.999840 | 4 |
| All Exons/RHDΨ | 1:7,520 | 0.999867 | 9 |
| Intron 4/Exon 7/Intron 7/W16X | 1:8,921 | 0.999888 | 4 |
| Intron 4/Exon 7/Intron 7/W16X/RHDΨ | 1:12,533 | 0.999920 | 5 |

REFERENCES

1. Andrews K T, Wolter L C, Saul A, Hyland C A: The RhD-trait in a white patient with the RhCCee phenotype attributed to a four-nucleotide deletion in the RHD gene. Blood 92:1839, 1998
2. Avent N D, Martin P G, Armstrong-Fisher S S, Liu W, Finning K M, Maddocks D, Urbaniak S J: Evidence of genetic diversity underlying Rh D negative, weak D ($D^u$) and partial D phenotypes as determined by multiplex PCR analysis of the RHD gene. Blood 89:2568, 1997
3. Avent N D, Liu W, Jones J W, Scott M L, Voak D, Pisacka M, Watt J, Fletcher A. Molecular analysis of Rh transcripts and polypeptides from individuals expressing the $D^{VI}$ variant phenotype: an RHD gene deletion event does not generate all $D^{VI}$ccEe phenotypes. Blood 1997; 89:1779-86.
4. Blumenfeld O O, Huang C H: Molecular genetics of the glycophorin gene family, the antigens for MNSs blood groups: multiple gene rearrangements and modulation of splice site usage result in extensive diversification. Hum Mutat 6:199, 1995
5. Blunt T, Daniels G, Carritt B: Serotype switching in a partially deleted RHD gene. Vox Sang 67:397, 1994
6. Bowman J: The management of hemolytic disease in the fetus and newborn. Semin Perinatol 21:39, 1997
7. Carritt B, Kemp T J, Poulter M: Evolution of the human RH (rhesus) blood group genes: a 50 year old prediction (partially) fulfilled. Hum Mol Genet. 6:843, 1997
8. Carritt B, Steers F J, Avent N D. Prenatal determination of fetal RhD type. Lancet 1994; 344:205-6.
9. Cherif-Zahar B, Mattel M G, Le Van Kim C, Bailly P, Cartron J P, Colin Y: Localization of the human Rh blood group gene structure to chromosome region 1p34.3-1p36.1 by in situ hybridization. Hum Genet. 86:398, 1991
10. Cherif-Zahar B, Bony V, Steffensen R, Gane P, Raynal V, Goosens D, Laursen J S, Varming K, Jersild C, Cartron J P. Shift from Rh-positive to Rh-negative phenotype caused by a somatic mutation within the RHD gene in a patient with chronic myelocytic leukaemia. Br J Haematol 1998; 102:1263-70.
11. Colin Y, Cherif-Zahar B, Le Van Kim C, Raynal V, van Huffel V, Cartron J-P. Genetic basis of the RhD-positive and RhD-negative blood group polymorphism as determined by southern analysis. Blood 1991; 78:2747-52.
12. Cossu G, Angius A, Gelfi C, Righetti P G: Rh D/d genotyping by quantitative polymerase chain reaction and capillary zone electrophoresis. Electrophoresis 17:1911; 1996
13. Daniels G L, Faas B H, Green C A, Smart E, Maaskant-van Wijk P A, Avent N D, Zondervan H A, von dem Borne A E, van der Schoot C E. The VS and V blood group polymorphisms in Africans: a serologic and molecular analysis. Transfusion 1998; 38:951-8.
14. Döscher A, Schunter F, Müller T H: Quantitative PCR to assess RHD zygosity. Infusionsther Transfusionsmed 26 (suppl 1):31, 1999 (abstr.)
15. Faas B H W, Becker E A M, Wildoer P, Ligthart P C, Overbeeke M A M, Zondervan H A, von dem Borne A E G K, van der Schoot C E: Molecular background of VS and weak C expression in blacks. Transfusion 37:38, 1997
16. Faas B H W, Beckers E A M, Simsek S, Overbeeke M A M, Pepper R, van Rhenen D J, von dem Borne A E G K, van der Schoot C E: Involvement of Ser103 of the Rh polypeptides in G epitope formation. Transfusion 36:506, 1996
17. Filbey D, Hanson U, Wesstrom G: The prevalence of red cell antibodies in pregnancy correlated to the outcome of the newborn: a 12 year study in central Sweden. Acta Obstet Gynecol Scand 74:687, 1995
18. Flegel W A, Khull S R, Wagner F F. Primary anti-D immunization by weak D type 2 RBCs. Transfusion 2000; 40: 428-434
19. Flegel W A, Wagner F F, Müller T H, Gassner C: Rh phenotype prediction by DNA typing and its application to practice. Transfus Med 8:281, 1998
20. Fujiwara H, Okuda H, Omi T, Iwamoto S, Tanaka Y, Takahashi J, Tani Y, Minakami H, Araki S, Sato I, Kajii E: The STR polymorphisms in intron 8 may provide information about the molecular evolution of RH haplotypes. Hum Genet. 104:301, 1999

21. Gassner C, Schmarda A, Kilga-Nogler S, Jenny-Feldkircher B, Rainer E, Müller T H, Wagner F F, Flegel W A, Schönitzer D: RhesusD/CE typing by polymerase chain reaction using sequence-specific primers. Transfusion 37:1020, 1997
22. Huang C H. Human $D^{VI}$ category erythrocytes: correlation of the phenotype with a novel hybrid RhD-CE-D gene but not an internally deleted RhD gene. Blood 1997; 89:1834-9.
23. Huang C H, Reid M E, Chen Y, Coghlan G, Okubo Y: Molecular definition of red cell Rh haplotypes by tightly linked SphI RFLPs. Am J Hum Genet. 58:133, 1996
24. Huang C H: Alteration of RH gene structure and expression in human dCCee and DCW—red blood cells: phenotypic homozygosity versus genotypic heterozygosity. Blood 88:2326, 1996
25. Hyland C A, Wolter L C, Saul A. Three unrelated Rh D gene polymorphisms identified among blood donors with Rhesus CCee (r'r') phenotypes. Blood 1994; 84:321-4.
26. Kemp T J, Poulter M, Carritt B: Microsatellite variation within the human RHCE gene. Vox Sang 77:159, 1999
27. Lo Y-M D, Bowell P J, Selinger M, Mackenzie I Z, Chamberlain P, Gillmer M D G, Littlewood T J, Fleming K A, Wainscoat J S: Prenatal determination of fetal RhD status by analysis of peripheral blood of rhesus negative mothers. Lancet 341:1147, 1993
28. Maaskant-van Wijk P A, Hemker M B, Douglas-Berger L, et al. Ethnic variability of the Rhesus system. Transfusion 1999; 39:(10S) 103S-4S (Abstract).
29. Maaskant-van Wijk P A, Faas B H W, de Ruijter J A M, Overbeeke M A M, von dem Borne A E G K, van Rhenen D J, van der Schoot C E. Genotyping of RHD by multiplex polymerase chain reaction analysis of six RHD-specific exons. Transfusion 1998; 38:1015-21.
30. Maaskant-van Wijk P A, Beckers E A M, van Rhenen D J, Mouro I, Colin Y, Carton J-P, Faas B H W, van der Schoot C E, Apoil P A, Blancher A, et al. Evidence that the RHD (VI) deletion genotype does not exist. Blood 1997; 90:1709-11.
31. MacGeoch C, Mitchell C J, Carritt B, Avent N D, Ridgwell K, Tanner M J, Spurr N K: Assignment of the chromosomal locus of the human 30-kDaI Rh (rhesus) blood group-antigen-related protein (Rh30A) to chromosome region 1p36.13-p34. Cytogenet Cell Genet. 59:261, 1992
32. Mourant A E, Kopec A C, Domaniewska-Sobczak K: The distribution of the human blood groups and other polymorphisms. London, Oxford University Press, 1976
33. Okuda H, Suganuma H, Tsudo N, Omi T, Iwamoto S, Kajii E: Sequence analysis of the spacer region between the RHD and RHCE genes. Biochem Biophys Res Commun 263:378, 1999
34. Okuda H, Kawano M, Iwamoto S, Tanaka M, Seno T, Okubo Y, Kajii E: The RHD gene is highly detectable in RhD-negative Japanese donors. J Clin Invest 100:373, 1997
35. Onda M, Fukuda M: Detailed physical mapping of the genes encoding glycophorins A, B and E, as revealed by P1 plasmids containing human genomic DNA. Gene 159:225, 1995
36. Reboul J, Gardiner K, Monneron D, Uze G, Lutfalla G: Comparative genomic analysis of the interferon/interleukin-10 receptor gene cluster. Genome Res 9:242, 1999
37. Salvignol I, Calvas P, Socha W W, Colin Y, Le Van Kim C, Bailly P, Ruffle J, Cartron J P, Blancher A: Structural analysis of the RH-like blood group gene products in nonhuman primates. Immunogenetics 41:271, 1995
38. Singleton B K, Green C A, Avent N D, Martin P G, Smart E, Daka A, Narter-Olaga E G, Hawthorne L M, Daniels G: The presence of an RHD pseudogene containing a 37 base pair duplication and a nonsense mutation in Africans with the Rh D-negative blood group phenotype. Blood 95:12, 2000
39. Urbaniak S J, Robertson A E: A successful program of immunizing Rh-negative male volunteers for anti-D production using frozen/thawed blood. Transfusion 21:64, 1981
40. Wagner F F, Gassner C, Müller T H, Schönitzer D, Schunter F, Flegel W A: Three molecular structures cause Rhesus D category VI phenotypes with distinct immunohematologic features. Blood 91:2157, 1998
41. Wagner F F, Kasulke D, Kerowgan M, Flegel W A: Frequencies of the blood groups ABO, Rhesus, D category VI, Kell, and of clinically relevant high-frequency antigens in South-Western Germany. Infusionsther Transfusionsmed 22:285, 1995
42. Wagner F F, Gassner C, Müller T H, Schönitzer D, Schunter F, Flegel W A: Molecular basis of weak D phenotypes. Blood 93:385, 1999
43. Wagner F F, Frohmajer A, Ladewig B, Eicher N I, Lonicer C B, Müller T H, Siegel M H, Flegel W A. Weak D alleles express distinct phenotypes. Blood 2000; 95: 2699-2708
44. Wagner F F, Flegel W A. RHD gene deletion occurred in the Rhesus box Blood 2000;
45. Wissenschaftlicher Beirat der Bundesärztekammer, Paul-Ehrlich-Institut. Richtlinien zur Blutgruppenbestimmung and Bluttransfusion (Hämotherapie). Köln: Deutscher Ärzte-Verlag; 1996.
46. Legler T J, Kohler M, Mayr W R, Panzer S, Ohto H, Fischer G F; Genotyping of the human platelet antigen systems 1 through 5 by multiplex polymerase chain reaction and ligation-based typing. Transfusion 1996 May; 36(5): 426-31

The invention claimed is:

1. An amplification product carrying a breakpoint region located in SEQ ID NOS 22-24, and/or a breakpoint region located in SEQ ID NOS 25-27, or both breakpoint regions, wherein the amplification product is labelled with a radioactive marker, or a fluorescent, phosphorescent, chemiluminescent or enzymatic label, or wherein the amplification product is fixed to a solid support.

2. The amplification product of claim 1, wherein the breakpoint region located in SEQ ID NOS 22-24 and/or SEQ ID NOS 25-27 encodes a polypeptide having antigen C reactivity.

3. The amplification product of claim 1, wherein the amplification product is labelled with the radioactive marker, or the fluorescent, phosphorescent, chemiluminescent or enzymatic label.

4. The amplification product of claim 1, wherein the amplification product is fixed to a solid support.

5. A gel comprising an amplification product carrying a breakpoint region located in SEQ ID NOS 22-24, and/or a breakpoint region located in SEQ ID NOS 25-27, or both breakpoint regions.

6. The gel of claim 5, wherein the breakpoint region located in SEQ ID NOS 22-24 and/or SEQ ID NOS 25-27 encodes a polypeptide having antigen C reactivity.

7. The gel of claim 5, wherein the gel comprises an electrophoresis gel.

8. The gel of claim 5, wherein the gel comprises an agarose gel.

9. The gel of claim 5, wherein the gel comprises a polyacrylamide gel.

10. The amplification product of claim 1, wherein the solid support comprises a chip.

11. The amplification product of claim 1, comprising the breakpoint region of SEQ ID NO:23 or SEQ ID NO:26.

12. The gel of claim 5, wherein the amplification product comprises the breakpoint region of SEQ ID NO:23 or SEQ ID NO:26.

* * * * *

SEQUENCE LISTING

<160> NUMBER OF SEQ ID NOS: 66

<210> SEQ ID NO 1
<211> LENGTH: 100
<212> TYPE: DNA
<213> ORGANISM: Homo sapiens

<400> SEQUENCE: 1

```
gcatgcgcga ctgagccggg tggatggtac tgctgcatcc gggtgtctgg aggctgtggc      60
cgttttgttt tcttggctaa aatcggggga gtgaggcggg                           100
```

-continued

```
<210> SEQ ID NO 2
<211> LENGTH: 26
<212> TYPE: DNA
<213> ORGANISM: Homo sapiens

<400> SEQUENCE: 2
actgcacgac ggggctggac tgacgt                                           26

<210> SEQ ID NO 3
<211> LENGTH: 45
<212> TYPE: DNA
<213> ORGANISM: Homo sapiens

<400> SEQUENCE: 3
agctgaaaaa aatgtctgga tttctagagg gcttgagatg ctcag                      45

<210> SEQ ID NO 4
<211> LENGTH: 26
<212> TYPE: DNA
<213> ORGANISM: Homo sapiens

<400> SEQUENCE: 4
gcttccattg ctgctggtgt actagt                                           26

<210> SEQ ID NO 5
<211> LENGTH: 44
<212> TYPE: DNA
<213> ORGANISM: Homo sapiens

<400> SEQUENCE: 5
agttttttac aggctggtgg attatcatag atgcagctgt tatt                       44

<210> SEQ ID NO 6
<211> LENGTH: 26
<212> TYPE: DNA
<213> ORGANISM: Homo sapiens

<400> SEQUENCE: 6
tatagcaacc atagccttcc taatgt                                           26

<210> SEQ ID NO 7
<211> LENGTH: 44
<212> TYPE: DNA
<213> ORGANISM: Homo sapiens

<400> SEQUENCE: 7
aggattaatg cagtatcgaa tggacaagtc cgaggtgata gtta                       44

<210> SEQ ID NO 8
<211> LENGTH: 26
<212> TYPE: DNA
<213> ORGANISM: Homo sapiens

<400> SEQUENCE: 8
tgaaggttgt ctgggtcaaa acaggt                                           26

<210> SEQ ID NO 9
<211> LENGTH: 44
<212> TYPE: DNA
<213> ORGANISM: Homo sapiens

<400> SEQUENCE: 9
aggtgctcgc atttggcttt tcgttggttt catgttggcc tttg                       44
```

```
<210> SEQ ID NO 10
<211> LENGTH: 26
<212> TYPE: DNA
<213> ORGANISM: Homo sapiens

<400> SEQUENCE: 10
tttttggagg ttatgttgct aaaggt                                              26

<210> SEQ ID NO 11
<211> LENGTH: 38
<212> TYPE: DNA
<213> ORGANISM: Homo sapiens

<400> SEQUENCE: 11
agaaaaagac atagtatacc ctggaattgc tgtatttt                                 38

<210> SEQ ID NO 12
<211> LENGTH: 26
<212> TYPE: DNA
<213> ORGANISM: Homo sapiens

<400> SEQUENCE: 12
tccagaatgc cttcatcttt tttggt                                              26

<210> SEQ ID NO 13
<211> LENGTH: 53
<212> TYPE: DNA
<213> ORGANISM: Homo sapiens

<400> SEQUENCE: 13
aggagggctg gtttttaagt ttggccgcac tgaagactta tggcagtgaa cac               53

<210> SEQ ID NO 14
<211> LENGTH: 249
<212> TYPE: DNA
<213> ORGANISM: Homo sapiens

<400> SEQUENCE: 14
agcatcatcc taatgaaact aaacatttat tttaaactta ttaaattgac tcttaaacta         60 agttttagt cttaattttt ttaatatcaa atctgtctct gaccttgttt cattatacat         120
aaggagcttt gctgtcatga gcgtttctca cgtacaaatg caggcaacag tgagaggaag        180
ttgtcttgtt tttgaacagg ccttgttttt cttggatgct tttgcttaaa atccaacagc        240
caaatgagg                                                                249

<210> SEQ ID NO 15
<211> LENGTH: 3093
<212> TYPE: DNA
<213> ORGANISM: Homo sapiens

<400> SEQUENCE: 15
attcactatc acaagaacag cacgggtaag acctgtcccc atgattcagt tacctcccac         60
tgggtccctc ccacaacgca tgggaattca ggatgagatt tgggtgggga cacaaccaaa        120
ccctatcatt ccaccccatgg cccctcccaa atttcatgtc ctcacatttc aaaaccaatc       180
acaccatccc aacagtccct caaagtctta aatgatttca gcattaactc aaaagtccac        240
agtctaatgt ctcatctgag acaaggcaag tcctttccat ttatgagcct ataaaatcca        300
aagcaagtta gttacttcct agatacaatg ggggtacagg cattgggtaa atacagccat        360
tccaaatggg ataaattggt caaaacaaag aggctacagg cccatgagag tccaaaatcc        420
```

```
agtggggcag tcaaatctta aagctccaaa atgatctcct ttgactccac atctcacatc    480
caggtcacgc agatggaagg ggtgggttcc catggtcttg ggcagctctg cccctgtacc    540
tttgcagggt acagcctccc tctcagctgc tttcatgggc tggcattgag tgtctgcagc    600
ttttccaggt acacggtgca agctgtcggt ggatctacca ttctgggtc  tggaggacct    660 cttctcacag ctccactagg tggtgcccca gtagggactg tgtgtggggt ctctgacccc    720
acatttccct tctgcactgc cctggcagag gatctccatg agggccctgc tcctgcagca    780
aacttctgac tgggcatcca ggcatttccg cacatcctct ttaatctagg cgaaggtttc    840
caaaccccaa ttcttgactt ctgtgcactc gcagtctcaa caccacatgg aagctgtcaa    900
ggcttggggc ttgcactccc cgaagctaca gcccaagctc taccttgcct cccgtcagtc    960
atggttggga gtggctggga tgcagggcac caagtcccta ggctgcacac agcatgagga   1020
ccccgggcct ggccaacaaa accatttttt cctgatacct ctggacctgt gatgggaggg   1080
gttgccataa agacctctga catgcccctgg acacattttc cccattgtct tgggaattag   1140
catttggctc ctgttactca tgcaaatttc tgcagccagc ttgaatttct cctcagaaaa   1200
tgggaatttt tcttttctat cacattgtca ggctgcaaat tttccgaact tttatgctct   1260
gcttccctta taaaactgaa tgtctttaac agcacccaag tcacctcttg aatgctttgc   1320
tgcttagaaa ttctcctgc  cagatactct aaatcatctc tctgaagttc aaagttctac   1380
aaatatctcg tgcaggggca aaatgccgcc agtatctttg ctaaaacata caagagtcc    1440 cctttgctcc agttcccaac aagttcctca tttccgtctg agaccacctc agcctatgga   1500
ctttattgtc cacagtgcta tcagcatttt gggcaaagcc attcaacaag tctctaggaa   1560
gttccaaact ttcccacatt tgcctgtctt cttctgagcc ctccaaactg ttccaaaccc   1620
tgcctgttac ccagttccaa agtcacatac ccatttttga gtatctacgg cagcacccca   1680
ctctactggt accaatttag ccactgaagt agttggagaa cagaagtaat agactctggt   1740
ttacattgta aaagcttctc tgtggctgct gtgtgaagaa aatatatgag aatgaagccc   1800
caagatgaag cagggacaca gttgcagtgg ttagagtaag aaatgctgct ggctggcact   1860
gaagtgatag cctggaggtt tgtgtgtgca catgcatgtg tatgtgtttt acgatagtag   1920
gcccaacaga tactgtaatc cacacttgtt ttttttttttt gagacagagt ctcacctgtt   1980
gcctagacta gaatgcagtg gcacaatctt ggctcactac aacctccacc tcccaggttc   2040
aaacaatcct tgtgcttcag cctcccgagt agttgggatt acaggtgtgt gccaccgtgc   2100
ccagctatat ttttttgtatt tttagcagag atgggatttt gccacattgg ccaggctggt   2160
cttgaactcc tggcctcaag caatcctccc accttagcct cccaaagtgc tgagccacca   2220
cacctggccg caactgattt ttaatcatga aatgacacat acatttaaaa aacccaatac   2280
ctataatatt cctggctagt actcttcaca tctatatcat caaaaacaaa gaaagtatgt   2340
gaaactgaca cagccaaggg gagactaagg agacataaca attaactgta atgtggtatt   2400
ctggagggga tcctggaaca gaaaaagaca ttaggcaaaa aactaaagaa atctgaataa   2460
aatgtggatg tcagttaata ataatgtatc atattagtcc agtaattgta acaaatatac   2520
cacaataatg aaagccatta attataggga aaatggaggg gttaatatgg gtggctggct   2580
tttgctattt ctagcagctc catttttatct gcaaaagaca aacattcatt aagtcccaaa   2640
aaggtaaaga atgacaaatt aagcatgtat cttattagta agagtaatat aaagatgctc   2700
actcctattt ataaatattt gacaatcatg ttaaggccac aaaagagaaa aaagggtagg   2760
ggcaaaaaac gcaaagagaa aggagttagt atcttttctc ccgcactcat tagctattaa   2820
```

```
aagaggatgt tgtttaaag ctgctcagag ctggtaaact aatgttaagt cactaacggg      2880
aatttaaaag gtttcattaa gaactgcctg cactagattc ctccaccctg agacattaaa      2940
caatcacgat aaacctcctg agtggtaaga acttgtccat ttaaaaacag gctatagatt      3000
gtatcatgca gttttatcta ctaatcggct aatatcccgc caaaaacaaa aaaccccaaa      3060
gggatgaaag tttcatccat caaaggaaac aac                                   3093

<210> SEQ ID NO 16
<211> LENGTH: 3099
<212> TYPE: DNA
<213> ORGANISM: Homo sapiens

<400> SEQUENCE: 16
attcactatc acaagaacag cacgggtaag acctgtcccc atgattcagt tacctcccac        60
tgggtccctc ccacaacgca tgggaattca ggatgagatt tgggtgggga cacaaccaaa       120
ccctatcatt ccacccatgg cccctcccaa atttcatgtc ctcacatttc aaaaccaatc       180
acaccatccc aacagtccct caaagtctta aatgatttca gcattaactc aaaagtccac       240
agtctaatgt ctcatctgag acaaggcaag tcctttccat ttatgagcct ataaaatcca       300
aagcaagtta gttacttcct agatacaatg ggggtacagg cattgggtaa atacagccat       360
tccaaatggg ataaattggt caaaacaaag aggctacagg cccatgagag tccaaaatcc       420 agtgggcag tcaatctta aagctccaaa atgatctcct tgactccac atctcacatc         480 caggtcacgc agatggaagg ggtgggttcc catggtcttg ggcagctctg cccctgtacc       540
tttgcagggt acagcctccc tctcagctgc tttcatgggc tggcattgag tgtctgcagc       600
ttttccaggt acacggtgca agctgtcggt ggatctacca ttctggggtc tggaggacct       660
cttctcacag ctccactagg tggtgcccca gtagggactg tgtgtggggt ctctgaccccc      720 acatttccct tctgcactgc cctggcagag gatctccatg agggccctgc cctgcagca       780 aacttctgac tgggcatcca ggcatttccg cacatcctct ttaatctagg cgaaggtttc       840
caaaccccaa ttcttgactt ctgtgcactc gcagtctcaa caccacatgg aagctgtcaa       900
ggcttggggc ttgcactccc cgaagctaca gcccaagctc taccttgcct cccgtcagtc       960
atggttggga gtggctggga tgcagggcac caagtcccta ggctgcacac agcatgagga      1020 cccccgggcct ggccaacaaa accattttt cctgatacct ctggacctgt gatgggaggg     1080
gttgccataa agacctctga catgccctgg agacattttc cccattgtct tgggaattag     1140
catttggctc ctgttactca tgcaaatttc tgcagccagc ttgaatttct cctcagaaaa     1200
tgggaatttt tcttttctat cacattgtca ggctgcaaat tttccgaact tttatgctct     1260
gcttccctta taaactgaa tgtctttaac agcacccaag tcacctcttg aatgctttgc       1320
tgcttagaaa tttctcctgc cagatactct aaatcatctc tctgaagttc aaagttctac     1380
aaatatctcg tgcaggggca aaatgccgcc agtatctttg ctaaaacata caagagtcc      1440 cctttgctcc agttcccaac aagttcctca tttccgtctg agaccacctc agcctatgga     1500
ctttattgtc cacagtgcta tcagcatttt gggcaaagcc attcaacaag tctctaggaa     1560
gttccaaact ttcccacatt tgcctgtctt cttctgagcc ctccaaactg ttccaaaccc     1620
tgcctgttac ccagttccaa agtcacatac ccatttttga gtatctacgg cagcacccca     1680
ctctactggt accaatttag ccactgaagt agttggagaa cagaagtaat agactctggt     1740
ttacattgta aaagcttctc tgtggctgct gtgtgaagaa aatatatgag aatgaagccc     1800
caagatgaag cagggacaca gttgcagtgg ttagagtaag aaatgctgct ggctggcact     1860
```

| | |
|---|---|
| gaagtgatag cctggaggtt tgtgtgtgca catgcatgtg tatgtgtttt acgatagtag | 1920 |
| gcccaacaga tactgtaatc cacacttgtt tttttttttt ttttgagaca gagtctcacc | 1980 |
| tgttgcctag actagaatgc agtggcacaa tcttggctca ctacaacctc cacctcccag | 2040 |
| gttcaaacaa tccttgtgct tcagcctccc gagtagttgg gattacaggt gtgtgccacc | 2100 |
| gtgcccagct atatttttg tattttagc agagatggga ttttgccaca ttggccaggc | 2160 |
| tggtcttgaa ctcctggcct caagcaatcc tcccaccttt gcctcccaaa gtgctgagcc | 2220 |
| accacacctg gccgcaactg atttttaatc atgaaatgac acatacattt aaaaaaccca | 2280 |
| atacctataa tattcctggc tagtactctt cacatctata tcatcaaaaa caagaaagt | 2340 |
| atgtgaaact gacacagcca aggggagact aaggagacat aacaattaac tgtaatgtgg | 2400 |
| tattctggag gggatcctgg aacagaaaaa gacattaggc aaaaaactaa agaaatctga | 2460 |
| ataaaatgtg gatgtcagtt aataataatg tatcatatta gtccagtaat tgtaacaaat | 2520 |
| ataccacaat aatgaaagcc attaattata gggaaatgg aggggttaat atgggtggct | 2580 |
| ggcttttgct atttctagca gctccatttt atctacaaaa gacaaacatt cattaagtcc | 2640 |
| caaaaggta aagaatgaca aattaagcat gtatcttatt agtaagagta atataaagat | 2700 |
| gctcactcat atttataaat atttgacaat gatgttaagg ccagaaaaga gaaaaaggg | 2760 |
| taggggcaaa aaacgcaaag agaaaggagt tagtatcttt tctcccgcac tcattagcta | 2820 |
| ttaaaagagg atgtttgttt aaagctgctc agagctggta aactaatgtt aagtcactaa | 2880 |
| cgggaattta aaaggtttca ttaagaactg cctgcactag attcctccac cctgagacat | 2940 |
| taaacaatca cgataaaacct cctgagtggt aagaacgtgt ccatttaaaa acaggctata | 3000 |
| gattgtcatg cagttttatc tactaatcgg ctaatgcacc gccaaaaaca aacaaaaaaa | 3060 |
| cccaaaggga tgaaagtttc atccatcaaa ggaaacaac | 3099 |

```
<210> SEQ ID NO 17
<211> LENGTH: 3099
<212> TYPE: DNA
<213> ORGANISM: Homo sapiens

<400> SEQUENCE: 17
```

| | |
|---|---|
| attcactatc acgagaacag cacgggtaag acctgtcccc atgattcagt tacctcccac | 60 |
| tgggtccctc ccacaacgca tgggaattca ggatgagatt tgggtgggga cacaaccaaa | 120 |
| ccctatcatt ccacccatgg cccctcccaa atttcatgtc ctcacatttc aaaaccaatc | 180 |
| acaccatccc aacagtccct caaagtctta aatgatttca gcattaactc aaaagtccac | 240 |
| agtctaatgt ctcatctgag acaaggcaag tcctttccat ctatgagcct ataaaatcca | 300 |
| aagcaagtta attacttcct agatacaatg ggggtacagg cattgggtaa atacagccat | 360 |
| tccaaatggg ataaattggt caaaacaaag aggctacagg cccatgagag tccaaaatcc | 420 |
| agtggggcag tcaaatctta aagctccaaa atgatctcct cttgactcca catctcacat | 480 |
| ccaggtcacg cagatggaag gggtgggttc ccatggtctt gggcagctct gcccctgtac | 540 |
| ctttgcaggg tacagcctcc ctctcagctg cttcatggg ctggcattga gtgtctgcaa | 600 |
| cttttccagg tacacggtgc aagctgtcgg tggatctacc attctgggt ctggaggacc | 660 |
| tcttctcaca gctccactag gtggtgcccc agtagggact gtgtgtgggg tctctgaccc | 720 |
| cacatttccc ttctgcactg ccctggcaga ggatctccat gagggccctg ccctgcagc | 780 |
| aaacttctgc ctgggcatcc aggcatttcc gcacatcctc tttaatctag gcgaaggttt | 840 |
| ccaaacccca gttcttgact tctgtgcact cgcagtctca acaccacatg gaagctgtca | 900 |

| | |
|---|---|
| aggcttgggg cttgcactcc ccgaagctac agcccaagct ctaccttgcc tcctgtcagt | 960 |
| catggttggg agtggctggg atgcagggca ccaagtccct aggctgcaca cagcatgagg | 1020 |
| accccgggcc tggccaacaa aaccattttt tcctgatatc tctggacctg tgatgggagg | 1080 |
| ggttgccata aagacctctg acatgccctg gagacatttt ccccattgtc ttgggaatta | 1140 |
| gcatttggct cctgttactc atgcaaattt ctgcagccag cttgaatttc tcctcagaaa | 1200 |
| atgggaattt ttcttttcta tcacattgtc aggctgcaaa ttttccgaac ttttatgctc | 1260 |
| tgcttccctt ataaaactga atgtctttaa cagcacccaa gtcacctctt gaatgctttg | 1320 |
| ctgcttagaa atttctcctg ccagatactc taaatcatct ctctgaagtt caaagttcta | 1380 |
| caaatatctc gtgcaggggc aaaatgccgc cagtatcttt gctaaaacat aacaagagtc | 1440 |
| cccttttgctc cagttcccaa caagttcctc atttccgtct gagaccacct cagcctatgg | 1500 |
| actttattgt ccacagtgct atcagcattt tgggcaaagc cattcaacaa gtctctagga | 1560 |
| agttccaaac tttcccacat ttgcctgtct tcttctgagc cctccaaact gttccaaacc | 1620 |
| ctgcctgtta cccagttcca aagtcacata cccattttttg agtatctacg gcagcacccc | 1680 |
| actctactgg taccaattta gccactgaag tagttggaga acagaagtaa tagactctgg | 1740 |
| tttacattgt aaaagcttct ctgtggctgc tgtgtgaaga aaatatatga gaatgaagcc | 1800 |
| ccaagatgaa gcagggacac agttgcagtg gttagagtaa gaaatgctgc tggctggcac | 1860 |
| tgaagtgata gcctggaggt ttgtgtgtgc acatgcatgt gtatgtgttt tacgatagta | 1920 |
| ggcccaacag atactgtaat ccacacttgt ttttttttttt ttttgagac agagtctcac | 1980 |
| ctgttgccta gactagaatg cagtggcaca atcttggctc actacaacct ccacctccca | 2040 |
| ggttcaaaca atccttgtgc ttcagcctcc cgagtagttg ggattacagg tgtgtgccac | 2100 |
| cgtgcccagc tatattttttt gtatttttag cagagatggg attttgccac attggccagg | 2160 |
| ctggtcttga actcctggcc tcaagcaatc ctcccacctt agcctcccaa agtgctgagc | 2220 |
| caccacacct ggccgcaact gattttttaat catgaaatga cacatacatt taaaaaaccc | 2280 |
| aatacctata atattcctgg ctagtactct tcacatctat atcatcaaaa acaaagaaag | 2340 |
| tatgtgaaac tgacacagcc aaggggagac taaggagaca taacaattaa ctgtaatgtg | 2400 |
| gtattctgga ggggatcctg gaacagaaaa agacattagg caaaaaacta agaaatctg | 2460 |
| aataaaatgt ggatgtcagt taataataat gtatcatatt agtccagtaa ttgtaacaaa | 2520 |
| tatcccaat aatgaaagcc attaattata gggaaaatgg aggggttaat atgggtggct | 2580 |
| ggcttttgct atttctagca gctccatttt atctacaaaa gacaaacatt cattaagtcc | 2640 |
| caaaaggta aagaatgaca aattaagcat gtatcttatt agtaagagta atataaagat | 2700 |
| gctcactcat atttataaat atttgacaat gatgttaagg ccagaaaaga gaaaaaggg | 2760 |
| tagggcaaa aaacgcaaag agaaaggagt tagtatcttt tctcccgcac tcattagcta | 2820 |
| ttaaaagagg atgtttgttt aaagctgctc agagctggta aactaatgtt aagtcactaa | 2880 |
| cgggaattta aaaggtttca ttaagaactg cctgcactag attcctccac cctgagacat | 2940 |
| taaacaatca cgataaacct cctgagtggt aagaacgtgt ccatttaaaa acaggctata | 3000 |
| gattgtcatg cagtttttatc tactaatcgg ctaatgcacc gccaaaaaca aacaaaaaaa | 3060 |
| cccaaaggga tgaaagtttc atccatcaaa ggaaacaac | 3099 |

<210> SEQ ID NO 18
<211> LENGTH: 9241
<212> TYPE: DNA
<213> ORGANISM: Homo sapiens

<400> SEQUENCE: 18

```
ctagaaaaca ctttgtcatt ttagaggtgt tatccaatgt tcgcgcaggc actggagtca     60
gagaaaatgg agttgaatcc tttctctgcc actctttgag gagaatctca ccatttatta    120
tgcactgtag aatacaacaa taaaatacag ccatgtacca cataacaaca tcttggtaaa    180
caacagactg catatatgat ggtggtcatc cagtaagcta aggttaattt attattattc    240
ccttttttttt ttcttttttt tgagatgtag tcttactctg tcacccaggc tagagtgcaa    300
tggcaccatc ttggctcact gcaacctctg cctcctgggt tcaagcgaat ctcctgcctc    360
agcctccgaa gtagctggga attacaggca cccaccacat ctggctaatt ttttgtattt    420
ttagtaaaga tgggggtttca ccatgttggc caggctgatc tcaaactcct gacctcaagt    480
gatctgcctg cctcggcctc ccaaagtgct gggaccatag gcctgagcca ctgtgcccgg    540
ccttgtttgc tttttttaaca gttaacagtg tgctcataga aactgctttg acatgactgc    600
aatcatgtgc ttcatagaaa cttaattaga ttataccact agagtcttca gatttttata    660
ctttttttttt tgaaacggag tctcactctg tcaccaggct ggagtgcagt gccgcaatct    720
cagctcgccg caacctccgc ctcccaggtt caagtgattc tcctgcctca gcctcccgag    780
tagctgggat tacaagtgca cactaccacg cccagctaat ttttgcattt ttactagaca    840
gggtttcacc atgttggcta ggatagtttc accaggatct cttggcctca tgatcagcct    900
gcctcggcct cccaaagtgc tgggattaca ggtgtgagcc accgtgccca gcctatactt    960
cccttttttga ataccatttg gcgttttgaa gaattaacag ctttgtgaac gtggcagtgc   1020
ttgtgattca ggcttccact gagaccaagg ggagaacctg gttgcaggac aaacagacgg   1080
acagcgtgtg gcagtgttta aatgctcttc tgaaggctga tacgacagct ctctgtgcac   1140
tgattgtata cgcatcccaa gattatatta ttgttttcta ttgctatgtg tcacactttg   1200
ccaaacagga tgtggaaaat gaataagcgg ttttcttagg cacttcttaa cagacaattg   1260
gtcaaaatga actccattgc ttaagaaaca cataaacacc atttagtcac tgaatatagc   1320
tatatgtatg gttgctacta tggggaatct tgttttgcca attttctttg aaaattctgg   1380
cagaccaagg ttcttttttgt ttacacaata cttgaaaaat aaaaatgaac aagccaacaa   1440
actaccaagt tttcacttac ataaatgtag ttacatacag aaaatgtgac tgtgaatttt   1500
ttctaggact tttaaactat aagcactatt tgcacgaaag agaaccaatc tatcaattac   1560
aaactcacat aattttacag attttttttt ccctacacag cacataaaac agaaggaatt   1620
tgaagccacc ctccaaacac agggggaagga ggctgtgtgt atatcctcat tgtctttcac   1680
attctaaggt ggttccactc agtgactgaa atccttaagt gttgtattag tcggctttggg   1740
ctaccataac agcagcttaa actgttgtta agccactcag acttaaacaa cagaaattta   1800
tttccttata gttctggagg ctggaagttc aaggtgccgg caaggctggt ttctggtgag   1860
acctctctcc ctgtcttgca gatggctgcc tcctccctgt gtcctcatag agcctgtcct   1920
ctgcttttac acttctggtg tcatcttcct ttttttttttt ttttgagac agagtctcgc   1980
tctatcgccc aggctggagt gcagtggccc gatcgatctc ggctcactgc aacctctgcc   2040
tcccaggttc aagcaattct cctgcctcag cctcccgagt agctgggact acaggtgccc   2100
gccatcatgt ctggctaatt tttgtatttt tagtagagac agggtttcac catattggcc   2160
aggctggtct ccaactcctg acctgtcat ctgcctgcct cggcctccca aagtgctagg   2220
attacaggcg tgagccaccg cacccggcct ctttctcttc ttataaggac accagtccta   2280
ttagattagg gctccaccct catgacctca tttgacctta actattattt ctttaaagca   2340
```

```
cctatttcca aatatagtca ctttaggggt tagggcttca aaatatgaat ctgagggaga   2400
tcaattcagt aaatagcagt agtcattaac ggacaatata tacaaagata atttcgtgat   2460
tactgtcctt atgcataaat gtcctcagtg ttccactgcc tttatccaga tttactatca   2520
caaagacttt gctctgagaa aaatgtgatt tctttctttt ttttttttt ttgagacaga    2580 gtctcactct gtcacccagg ctggagtgca gtggtgcaat ctcggctcac tgcaatctcc   2640
gcctcccagg ttcacgccat tctcttgcct cagtctcccg agtagctggg cctacaggcg   2700
cccgccaccc tgcccagcta atttttttgta ttttttagtag agacggggtt tcaccatgtt  2760
agccaggatg gtctcaatct cctgacctcg tgatccacct gcctcagcct cccaaagtgc   2820
tgggattaca ggcatgagcc accgcgccca gcagattttt tttttttttt ttttttttg    2880 agatggagtc ttgctgtgtt gcccagcctg gagtgcagtg ttatgatttt ggctcactgc   2940
aacctctgtc taccatgttc aagcgattct cccacctctg cctcccgtgt agctgggatc   3000
acaggcacac gccaccacac ctagctactt tttgtatttt tagtagaaat ggggtttcac   3060
catgttggcc aggatggtcc cgaactcctg acctcaagtg atcctcctgc ctcggcctcc   3120
caaagtgctg ggattacagg tgtgagccac tgtgcctggc caaaaatgtg atttcttatt   3180
tcccacattg ccaattccat ttcaattaac tataatagct atgtctattg agcactcaag   3240
tgtattctag aaactgttcc tgattctggg gatatatcca tgaatcaact atagtccctg   3300
ttattaagta atctgtagtc tgactaaacc attagaaatt taaaaaatgg ctactttcaa   3360
agacatcttg gagttcagga gtcccacact gcgaaccata ttacctaata atccaacctg   3420
cttgtaattc acttatttaa ccaatattta ttgagtgcca actttgagcc taagatacag   3480
cagtaaacaa atggataaag tccctgtcct catgaaactt gtattctaat ggaagaaaca   3540
gaaaacaaac agatatagga tgtaatatca ggtagggata aatactttga attcaaacaa   3600
aagtatacgt agtcagggtt cgccaaagag acacagccaa tcggatacat agatatataa   3660
aagagggttt atgagttaga aagggctcac atgattacag aggctgagaa gtcccacagc   3720
agattgtctg caagctggag acccagggat actggtagca tggctcagtc caagtcccaa   3780
agcctcagaa tcaggaaagc tgatgatata attcttagcc caaaggcctt agaaccccag   3840
cggtgacgga aaggctgatg taggtcctgg agtcctgaga cccaacagcc tgggatcctg   3900
aaatccaagg gcaggaatgg aagcgtgtat tccagctcca agagagtaag accaatttgc   3960 cttttcttccg ttttttgtttc aagccacctg cacattgagg gcggatggtt ccctcttagt  4020
ccattcagtc atatatcaat ctcttctgga aatacccctca cagacacact aacaaataat   4080 gccttttccag ttctctaggt attctttaat ccagtcaagc tgacacctaa aattaaccat   4140
cacaaaagtt aaggagaaag aagacaactt gtagggagg ctgctatgca agacagtgtg    4200
tgaaggaagg gctctctgaa gaggttaata tctgagcaga gacttgaatg aagtgaagaa   4260
gtgagccatg tgggtatggg gaatacaact tccaggtaga aagacaagt gtggtgtgta    4320 tcagggtcag caaagaagcc atgtgacaga gaagggtggg ccaggagag acggataagt    4380 gatctaactc ctgaggaggt ggcctggcca ggagctagag catgaagatc tcgtaggact   4440
ttattctgca aggtgaaaag ccattgtatt agtctgttca caacccgag actaggcaat    4500 ttacaaaaga aagagaggtt taatggactt acagttccac atggctgggg aggcctcaca   4560
atcatggcga aagcaatga ggagcaagtc acgtcttacg tggatggcag gcaaagacaa    4620
agacagcttg tgcagagaaa ctccccctta tagagccatc agatcctgtt agacttattc   4680
actatcacaa gaacagcacg ggtaagacct gtccccatga ttcagttacc tcccactggg   4740
```

```
tccctcccac aacgcatggg aattcaggat gagatttggg tggggacaca accaaaccct    4800
atcattccac ccatggcccc tcccaaattt catgtcctca catttcaaaa ccaatcacac    4860
catcccaaca gtccctcaaa gtcttaaatg atttcagcat taactcaaaa gtccacagtc    4920
taatgtctca tctgagacaa ggcaagtcct ttccatttat gagcctataa aatccaaagc    4980
aagttagtta cttcctagat acaatggggg tacaggcatt gggtaaatac agccattcca    5040
aatgggataa attggtcaaa acaaagaggc tacaggccca tgagagtcca aaatccagtg    5100
gggcagtcaa atcttaaagc tccaaaatga tctcctttga ctccacatct cacatccagg    5160
tcacgcagat ggaaggggtg ggttcccatg gtcttgggca gctctgcccc tgtacctttg    5220
cagggtacag cctccctctc agctgctttc atgggctggc attgagtgtc tgcagctttt    5280
ccaggtacac ggtgcaagct gtcggtggat ctaccattct ggggtctgga ggacctcttc    5340
tcacagctcc actaggtggt gccccagtag ggactgtgtg tggggtctct gaccccacat    5400
ttcccttctg cactgccctg gcagaggatc tccatgaggg ccctgctcct gcagcaaact    5460
tctgactggg catccaggca tttccgcaca tcctctttaa tctaggcgaa ggtttccaaa    5520
ccccaattct tgacttctgt gcactcgcag tctcaacacc acatggaagc tgtcaaggct    5580
tggggcttgc actccccgaa gctacagccc aagctctacc ttgcctcccg tcagtcatgg    5640 ttggagtgg ctgggatgca gggcaccaag tccctaggct gcacacagca tgaggacccc    5700
gggcctggcc aacaaaacca ttttttcctg atacctctgg acctgtgatg ggaggggttg    5760
ccataaagac ctctgacatg ccctggagac attttcccca ttgtcttggg aattagcatt    5820
tggctcctgt tactcatgca aatttctgca gccagcttga attctcctc agaaaatggg    5880 aatttttctt ttctatcaca ttgtcaggct gcaaattttc cgaacttta tgctctgctt    5940 cccttataaa actgaatgtc tttaacagca cccagtcac ctcttgaatg ctttgctgct    6000
tagaaatttc tcctgccaga tactctaaat catctctctg aagttcaaag ttctacaaat    6060
atctcgtgca ggggcaaaat gccgccagta tcttgctaa aacataacaa gagtcccctt    6120
tgctccagtt cccaacaagt tcctcatttc cgtctgagac cacctcagcc tatggacttt    6180
attgtccaca gtgctatcag catttttggc aaagccattc aacaagtctc taggaagttc    6240
caaactttcc cacatttgcc tgtcttcttc tgagccctcc aaactgttcc aaaccctgcc    6300
tgttacccag ttccaaagtc acatacccat ttttgagtat ctacggcagc accccactct    6360
actggtacca atttagccac tgaagtagtt ggagaacaga agtaatagac tctggtttac    6420
attgtaaaag cttctctgtg gctgctgtgt gaagaaaata tatgagaatg aagcccccaag    6480 atgaagcagg gacacagttg cagtggttag agtaagaaat gctgctggct ggcactgaag    6540
tgatagcctg gaggtttgtg tgtgcacatg catgtgtatg tgttttacga tagtaggccc    6600
aacagatact gtaatccaca cttgttttttt tttttttttt gagacagagt ctcacctgtt    6660
gcctagacta gaatgcagtg gcacaatctt ggctcactac aacctccacc tcccaggttc    6720
aaacaatcct tgtgcttcag cctcccgagt agttgggatt acaggtgtgt gccaccgtgc    6780
ccagctatat ttttttgtatt tttagcagag atgggatttt gccacattgg ccaggctggt    6840
cttgaactcc tggcctcaag caatcctccc accttagcct cccaaagtgc tgagccacca    6900
cacctggccg caactgattt ttaatcatga aatgacacat acatttaaaa aacccaatac    6960
ctataatatt cctggctagt actcttcaca tctatatcat caaaaacaaa gaaagtatgt    7020
gaaactgaca cagccaaggg gagactaagg agacataaca attaactgta atgtggtatt    7080
ctggagggga tcctggaaca gaaaaagaca ttaggcaaaa aactaaagaa atctgaataa    7140
```

```
aatgtggatg tcagttaata ataatgtatc atattagtcc agtaattgta acaaatatac    7200
ccaataatga aagccattaa ttatagggaa aatggagggg ttaatatggg tggctggctt    7260
ttgctatttc tagcagctcc attttatcta caaaagacaa acattcatta agtcccaaaa    7320
aggtaaagaa tgacaaatta agcatgtatc ttattagtaa gagtaatata agatgctca     7380 ctcatatttta taaatatttg acaatgatgt taaggccaga aaagagaaaa aagggtaggg    7440
gcaaaaaacg caaagagaaa ggagttagta tcttttctcc cgcactcatt agctattaaa    7500
agaggatgtt tgtttaaagc tgctcagagc tggtaaacta atgttaagtc actaacggga    7560
atttaaaagg tttcattaag aactgcctgc actagattcc tccaccctga gacattaaac    7620
aatcacgata aacctcctga gtggtaagaa cgtgtccatt taaaaacagg ctatagattg    7680
tcatgcagtt ttatctacta atcggctaat gcaccgccaa aaacaaacaa aaaaacccaa    7740
agggatgaaa gtttcatcca tcaaaggaaa caacagtcac cttggttccc atcccactca    7800
tatactgccg ccgtacatgt caatcagatg aacctgtgcg tatctcttaa cgacaattga    7860
cccacctttt taactgaagt gaagggggggt tctgctccgc gaccacttcc tggatctctc    7920
ccttcaccct ctgtgttctt tcgggtgcac catcgggtca aagccgcagc aacgccgtct    7980
ctgtgtgatc gcatgtgccc ttctgcacac gaccttcccc cgagagtgac cagctaccgg    8040
acaggcacca aggagggcta ccgagcacct cccggaccgg cggctgcagg atcgcgagcg    8100
cctccgctag ggagaccgca cgttgcgcct gtgcttcctg cggtggcgcc ttctgcaagg    8160
agacctcgac cctgctccct ctccggggct ggatctgact ccttgacggt gattccagac    8220
gcgagaccca aactgacggc ttctagaaga ggggcgagcc cggccgcaag tctttcacgt    8280
agctaagtca tcgttgcttc cggcttctta ccgttctccc ctttgtaaac ggttacctcc    8340
cgaaaaccca ggctctcctc caacagtggt tctcaagcga ggcgatcttc cccgggaggg    8400
gatatttggc aaagtctggg ggcatttttg gttcactggg gctgctactt gcatccactg    8460
ggtagaggcg ggggatgcag ctacacaacc tgcgaagcac gggacagcac cctccccaac    8520
ccagacagaa ttagccggcc caaaacctca gtagtgccca ggctgagaaa ccctgcctta    8580
aacaaacaac aaagaaaggc caagtcccat aagtgggtca ccgcgccgag actggggtcc    8640
acgggacacc ccagccacgc caagccggga agtccccgcc tcctggagct gaacccgccc    8700
ctctcccaga ggtggagctg cggggggcgg aacaggcac ggagaaaata aacaagacta    8760
aaaagtcctg agtagcgctg tgtggccgca aacctgaacc caccttttgc accacgcggg    8820
acccggcact cttcctgcca cccacccctg agagggctgc gcggccgacc ccagtactag    8880
aaaacactcg tcacctcact caagacgggt acgaaggcca acgacgcct tcctttagaa     8940 cgctcagcac acagagcaac ttctcacgcc tactctcaaa tggcgtactc caaactagca    9000
ctcccgacgt ccagctgtga acccagagcg gcggaaagcc cctgaaccca gcgcccgggc    9060
atgcgcagac gcgttgttgt ggtgggcgtg gctccctccg gacccggcgc ccgcccctcc    9120
gccccgtgtc cgcatgcgcg actgagccgg gtggatggta ctgctgcatc cgggtgtctg    9180
gaggctgtgg ccgttttgtt ttcttggcta aaatcggggg agtgaggcgg gccggcgcgg    9240
c                                                                    9241

<210> SEQ ID NO 19
<211> LENGTH: 9236
<212> TYPE: DNA
<213> ORGANISM: Homo sapiens
```

```
<400> SEQUENCE: 19
ctagaaaaca ctttgtcatt ttagaggtgt tatccaatgt tcgcgcaggc actggagtca      60
gagaaaatgg agttgaatcc tttctctgcc actctttgag gagaatctca ccatttatta     120
tgcactgtag aatacaacaa taaaatacag ccatgtacca cataacaaca tcttggtaaa     180
caacagactg catatatgat ggtggtcatc cagtaagcta aggttaattt attattattc     240
ccttttttt ttctttttt tgagatgtag tcttactctg tcacccaggc tagagtgcaa     300
tggcaccatc ttggctcact gcaacctctg cctcctgggt tcaagcgaat ctcctgcctc     360
agcctccgaa gtagctggga attacaggca cccaccacat ctggctaatt ttttgtattt     420
ttagtaaaga tggggtttca ccatgttggc caggctgatc tcaaactcct gacctcaagt     480
gatctgcctg cctcggcctc ccaaagtgct gggaccatag gcctgagcca ctgtgcccgg     540
ccttgtttgc tttttaaca gttaacagtg tgctcataga aactgctttg acatgactgc     600
aatcatgtgc ttcatagaaa cttaattaga ttataccact agagtcttca gattttata     660
ctttttttt tgaaacggag tctcactctg tcaccaggct ggagtgcagt gccgcaatct     720
cagctcgccg caacctccgc ctcccaggtt caagtgattc tcctgcctca gcctcccgag     780
tagctgggat tacaagtgca cactaccacg cccagctaat ttttgcattt ttactagaca     840
gggtttcacc atgttggcta ggatagtttc accaggatct cttggcctca tgatcagcct     900
gcctcggcct cccaaagtgc tgggattaca ggtgtgagcc accgtgccca gcctatactt     960
cccttttga ataccatttg gcgttttgaa gaattaacag ctttgtgaac gtggcagtgc    1020
ttgtgattca ggcttccact gagaccaagg ggagaacctg gttgcaggac aaacagacgg    1080
acagcgtgtg gcagtgttta aatgctcttc tgaaggctga tacgacagct ctctgtgcac    1140
tgattgcata cgcatcccaa gattatatta ttgttttcta ttgctatgtg tcacactttg    1200
ccaaacagga tgtggaaaat gaataagcgg ttttcttagg cacttcttaa cagacaattg    1260
gtcaaaatga actccattgc ttaagaaaca cataaacacc atttagtcac tgaatatagc    1320
tatatgtatg gttgctacta tggggaatct tgttttgcca attttctttg aaaattctgg    1380
cagaccaagg ttcttttttgt ttacacaata cttgaaaaat aaaatgaac aagccaacaa    1440
actaccaagt tttcacttac ataaatgtag ttacatacag aaaatgtgac tgtgaatttt    1500
ttctaggact tttaaactat aagcactatt tgcacgaaag agaaccaatc tatcaattac    1560
aaactcacat aatttttacag attttttttt ccctacacag cacataaaac agaaggaatt    1620
tgaagccacc ctccaaacac aggggaagga ggctgtgtgt atatcctcat tgtctttcac    1680
attctaaggt ggttccactc agtgactgaa atccttaagt gttgtattag tcggctttgg    1740
ctaccataac agcagcttaa actgttgtta agccactcag acttaaacaa cagaaattta    1800
tttccttata gttctggagg ctggaagttc aaggtgccgg caaggctggt ttctggtgag    1860
acctctctcc ctgtcttgca gatggctgcc tcctccctgt gtcctcatag agcctgtcct    1920
ctgcttttac acttctggtg tcatcttcct tttttttttt ttttgagac agagtctcgc    1980
tctatcgccc aggctggagt gcagtggccc gatcgatctc ggctcactgc aacctctgcc    2040
tcccaggttc aagcaattct cctgcctcag cctcccgagt agctgggact acaggtgccc    2100
gccatcatgt ctggctaatt tttgtatttt tagtagagac agggtttcac catattggcc    2160
aggctggtct ccaactcctg accttgtcat ctgcctgcct cggcctccca aagtgctagg    2220
attacaggcg tgagccaccg cacccggcct cttttctcttc ttataaggac accagtccta    2280
ttagattagg gctccaccct catgacctca tttgacctta actattattt ctttaaagca    2340
```

```
cctatttcca aatatagtca ctttaggggt tagggcttca aaatatgaat ctgagggaga    2400
tcaattcagt aaatagcagt agtcattaac ggacaatata tacaaagata atttcgtgat    2460
tactgtcctt atgcataaat gtcctcagtg ttccactgcc tttatccaga tttactatca    2520
caaagacttt gctctgagaa aaatgtgatt tctttctttt ttttttttt ttgagacaga    2580 gtctcactct gtcacccagg ctggagtgca gtggtgcaat ctcggctcac tgcaatctcc    2640
gcctcccagg ttcacgccat tctcttgcct cagtctcccg agtagctggg cctacaggcg    2700
cccgccaccc tgcccagcta attttttgta tttttagtag acgggggtt tcaccatgtt    2760 agccaggatg gtctcaatct cctgacctcg tgatccacct gcctcagcct cccaaagtgc    2820
tgggattaca ggcatgagcc accgcgccca gcagattttt ttttttttt tttttttttg    2880 agatggagtc ttgctgtgtt gcccagcctg gagtgcagtg ttatgatttt ggctcactgc    2940
aacctctgtc taccatgttc aagcgattct cccacctctg cctcccgtgt agctgggatc    3000
acaggcacac gccaccacac ctagctactt tttgtatttt tagtagaaat ggggtttcac    3060
catgttggcc aggatggtcc cgaactcctg acctcaagtg atcctcctgc ctcggcctcc    3120
caaagtgctg ggattacagg tgtgagccac tgtgcctggc caaaaatgtg atttcttatt    3180
tcccacattg ccaattccat ttcaattaac tataatagct atgtctattg agcactcaag    3240
tgtattctag aaactgttcc tgattctggg gatatatcca tgaatcaact atagtccctg    3300
ttattaagta atctgtagtc tgactaaacc attagaaatt taaaaaatgg ctactttcaa    3360
agacatcttg gagttcagga gtcccacact gcgaaccata ttacctaata atccaacctg    3420
cttgtaattc acttatttaa ccaatattta ttgagtgcca actttgagcc taagatacag    3480
cagtaaacaa atggataaag tccctgtcct catgaaactt gtattctaat ggaagaaaca    3540
gaaaacaaac agatatagga tgtaaatatca ggtagggata aatactttga attcaaacaa    3600
aagtatacgt agtcagggtt cgccaaagag acacagccaa tcggatacat agatatataa    3660
aagagggttt atgagttaga aagggctcac atgattacag aggctgagaa gtcccacagc    3720
agattgtctg caagctggag acccagggat actggtagca tggctcagtc caagtcccaa    3780
agcctcagaa tcaggaaagc tgatgatata attcttagcc caaaggcctt agaaccccag    3840
cggtgacgga aaggctgatg taggtcctgg agtcctgaga cccaacagcc tgggatcctg    3900
aaatccaagg gcaggaatgg aagcgtgtat tccagctcca agagagtaag accaatttgc    3960
cttctttccg ttttttgtttc aagccacctg cacattgagg gcggatggtt ccctcttagt    4020
ccattcagtc atatatcaat ctcttctgga aatacccctca cagacacact aacaaataat    4080
gcctttccag ttctctaggt attctttaat ccagtcaagc tgacacctaa aattaaccat    4140
cacaaaagtt aaggagaaag aagacaactt gtaggggagg ctgctatgca agacagtgtg    4200
tgaaggaagg gctctctgaa gaggttaata tctgagcaga gacttgaatg aagtgaagaa    4260
gtgagccatg tgggtatggg gaatacaact tccaggtaga aagacaagt gtggtgtgta    4320 tcagggtcag caaagaagcc atgtgacaga gaagggtggg ccaggagag acggataagt    4380 gatctaactc ctgaggaggt ggcctggcca ggagctagag catgaagatc tcgtaggact    4440
ttattctgca aggtgaaaag ccattgtatt agtctgttca caacccgag actaggcaat    4500 ttacaaaaga aagagaggtt taatggactt acagttccac atggctgggg aggcctcaca    4560
atcatggcga aaggcaatga ggagcaagtc acgtcttacg tggatggcag gcaaagacaa    4620
agacagcttg tgcagagaaa ctccccctta tagagccatc agatcctgtt agacttattc    4680
actatcacaa gaacagcacg ggtaagacct gtccccatga ttcagttacc tcccactggg    4740
```

```
tccctcccac aacgcatggg aattcaggat gagatttggg tggggacaca accaaaccct    4800
atcattccac ccatggcccc tcccaaattt catgtcctca catttcaaaa ccaatcacac    4860
catcccaaca gtccctcaaa gtcttaaatg atttcagcat taactcaaaa gtccacagtc    4920
taatgtctca tctgagacaa ggcaagtcct ttccatttat gagcctataa aatccaaagc    4980
aagttagtta cttcctagat acaatggggg tacaggcatt gggtaaatac agccattcca    5040
aatgggataa attggtcaaa acaaagaggc tacaggccca tgagagtcca aaatccagtg    5100
gggcagtcaa atcttaaagc tccaaaatga tctcctttga ctccacatct cacatccagg    5160
tcacgcagat ggaaggggtg ggttcccatg gtcttgggca gctctgcccc tgtacctttg    5220
cagggtacag cctccctctc agctgctttc atgggctggc attgagtgtc tgcagctttt    5280
ccaggtacac ggtgcaagct gtcggtggat ctaccattct ggggtctgga ggacctcttc    5340
tcacagctcc actaggtggt gccccagtag ggactgtgtg tggggtctct gaccccacat    5400
ttcccttctg cactgccctg gcagaggatc tccatgaggg ccctgctcct gcagcaaact    5460
tctgactggg catccaggca tttccgcaca tcctctttaa tctaggcgaa ggtttccaaa    5520
ccccaattct tgacttctgt gcactcgcag tctcaacacc acatggaagc tgtcaaggct    5580
tggggcttgc actccccgaa gctacagccc aagctctacc ttgcctcccg tcagtcatgg    5640 ttggagtgg ctgggatgca gggcaccaag tccctaggct gcacacagca tgaggacccc    5700
gggcctggcc aacaaaacca ttttttcctg atacctctgg acctgtgatg ggaggggttg    5760
ccataaagac ctctgacatg ccctggagac attttcccca ttgtcttggg aattagcatt    5820
tggctcctgt tactcatgca aatttctgca gccagcttga atttctcctc agaaaatggg    5880 aattttctt ttctatcaca ttgtcaggct gcaaattttc cgaacttta tgctctgctt    5940 cccttataaa actgaatgtc tttaacagca cccagtcac ctcttgaatg ctttgctgct    6000 tagaaattc tcctgccaga tactctaaat catctctctg aagttcaaag ttctacaaat    6060
atctcgtgca ggggcaaaat gccgccagta tctttgctaa aacataacaa gagtccccctt    6120 tgctccagtt cccaacaagt tcctcatttc cgtctgagac cacctcagcc tatggacttt    6180
attgtccaca gtgctatcag catttttgggc aaagccattc aacaagtctc taggaagttc    6240
caaactttcc cacatttgcc tgtcttcttc tgagccctcc aaactgttcc aaaccctgcc    6300
tgttacccag ttccaaagtc acatacccat ttttgagtat ctacggcagc accccactct    6360
actggtacca atttagccac tgaagtagtt ggagaacaga agtaatagac tctggtttac    6420
attgtaaaag cttctctgtg gctgctgtgt gaagaaaata tatgagaatg aagccccaag    6480
atgaagcagg gacacagttg cagtggttag agtaagaaat gctgctggct ggcactgaag    6540
tgatagcctg gaggtttgtg tgtgcacatg catgtgtatg tgttttacga tagtaggccc    6600
aacagatact gtaatccaca cttgttttt ttttttgaga cagagtctca cctgttgcct    6660
agactagaat gcagtggcac aatcttggct cactacaacc tccacctccc aggttcaaac    6720
aatccttgtg cttcagcctc ccgagtagtt gggattacag gtgtgtgcca ccgtgcccag    6780
ctatattttt tgtatttta gcagagatgg gattttgcca cattggccag gctggtcttg    6840
aactcctggc ctcaagcaat cctcccacct tagcctccca aagtgctgag ccaccacacc    6900
tggccgcaac tgattttaa tcatgaaatg acacatacat ttaaaaaacc caatacctat    6960
aatattcctg gctagtactc ttcacatcta tatcatcaaa aacaaagaaa gtatgtgaaa    7020
ctgacacagc caaggggaga ctaaggagac ataacaatta actgtaatgt ggtattctgg    7080
aggggatcct ggaacagaaa aagacattag gcaaaaaact aaagaaatct gaataaaatg    7140
```

-continued

| | |
|---|---|
| tggatgtcag ttaataataa tgtatcatat tagtccagta attgtaacaa atataccaca | 7200 |
| ataatgaaag ccattaatta tagggaaaat ggaggggtta atatgggtgg ctggcttttg | 7260 |
| ctatttctag cagctccatt ttatctgcaa aagacaaaca ttcattaagt cccaaaaagg | 7320 |
| taaagaatga caaattaagc atgtatctta ttagtaagag taatataaag atgctcactc | 7380 |
| ctatttataa atatttgaca atcatgttaa ggccacaaaa gagaaaaaag ggtaggggca | 7440 |
| aaaaacgcaa agagaaagga gttagtatct tttctcccgc actcattagc tattaaaaga | 7500 |
| ggatgtttgt ttaaagctgc tcagagctgg taaactaatg ttaagtcact aacgggaatt | 7560 |
| taaaaggttt cattaagaac tgcctgcact agattcctcc accctgagac attaaacaat | 7620 |
| cacgataaac ctcctgagtg gtaagaactt gtccatttaa aaacaggcta tagattgtat | 7680 |
| catgcagttt tatctactaa tcggctaata tcccgccaaa aacaaaaaac cccaaaggga | 7740 |
| tgaaagtttc atccatcaaa ggaaacaaca gtcaccttgg ttcccatctc actcatatac | 7800 |
| tgccgccgta catgtcaatc agatgaacct gtgcgtatct cttaatgaca attgacccac | 7860 |
| attttttgact gaagtgaaag ggggttctgc tccgcgacca cttcctggat ctcccccctcc | 7920 |
| accctctgtg ttctttcggg tgcaccatcg ggtcaaagcc gcagcaacgc cgtctctgtg | 7980 |
| tgatcgcatg tgcccttctg cacacgacct tcccccgaga gtgaccagct accggacagg | 8040 |
| caccaaggag ggctaccgag cacctcccgg accggcggct gcaggatcgc gagcgcctcc | 8100 |
| gctagggaga ctgcacgttg cgcctgtgct tcctgcggtg gcgccttctg caaggagacc | 8160 |
| tcgaccctgc tccctctccg gggctggatc tgactccttg acggtgattc cagacgcgag | 8220 |
| acccaaactg acggcttcta aagaggggc gagcccggcc gcaagtcttt cacgtagcta | 8280 |
| agtcatcgtt gcttccggct tcttaccgtt ctcccctttg taaacggtta cctcccgaaa | 8340 |
| acccaggctc tcctccaaca gtggttctca agcgaggcga tcttccccgg gaggggatat | 8400 |
| ttggcaaagt ctgggggcat ttttggttca ctggggctgc tacttgcatc cactgggtag | 8460 |
| aggcgggggga tgcagctaca caacctgcga agcacgggac agcaccctcc ccaacccaga | 8520 |
| cagaattagc cggcccaaaa cctcagtagt gcccaggctg agaaaccctg ccttaaacaa | 8580 |
| acaacaaaga aaagccaagt cccataagtg ggtcaccgcg ccgagactgg ggtccacggg | 8640 |
| acacccagc cacgccaagc cgggaagtcc ccgcctcctg gagctgaacc cgcccctctc | 8700 |
| ccagaggtgg agctgcgggg ggcgggaaca ggcacggaga aaataaacaa gactaaaaag | 8760 |
| tcctgagtag cgctgtgtgg ccgcaaacct gaacccacct tttgcaccac gcgggacccg | 8820 |
| gcacgcttcc tgccacccac ccctgagagg gctgcgcggc cgaccccagt actagaaaac | 8880 |
| actcgtcacc tcaatcaaga cgggtacgaa ggccaacgga cgccttcctt tagaacgctc | 8940 |
| agcacacaga gcaacttctc acgcctactc tcaaatggcg tactccaaac tagcactccc | 9000 |
| gacgtccagc tgtgaaccca gagcggcgga aagcccctga acccagcgcc cgggcatgcg | 9060 |
| cagacgcgtt gttgtggtgg gcgtggctcc ctccggaccc ggcgccccgc cctccgcccc | 9120 |
| gtgtccgcat gcgcgactga gccgcggggg tggtactgct gcatccgggt gtctgaagat | 9180 |
| ccgatgaaat aacatatgca aaatgattgg gtccgtgatt ggcattccag aaatgg | 9236 |

<210> SEQ ID NO 20
<211> LENGTH: 9238
<212> TYPE: DNA
<213> ORGANISM: Homo sapiens

```
<400> SEQUENCE: 20
aaacgctcat gacagcaaag tctccaatgt tcgcgcaggc actggagtca gagaaaatgg      60
agttgaatcc tttctctgcc actctttgag gagaatctca ccatttatta tgcactgtag     120
aatacaacaa taaatacag ccatgtacca cataacaaca tcttggtaaa caacagactg      180
catatatgat ggtggtcatc cagtaagcta aggttaattt attattattc cttgtttttt     240 ttttttttt ttttttttg agatgtagtc ttactctgtc acccaggcta gagtgcaatg       300
gcaccatctt ggctcactgc aacctctacc tcctgggttc aagcaaatct cctgcctcag     360
cctccaaagt agctgggatt acaggcaccc accacatctg ctaatttttt tgtattttta     420
gtaaagatgg ggtttcacca tgttggccag gctgatctca aactcctgac ctcaagtgat     480
ctgcccgcct cggcctccca agtgctggat accacaggcc tgagccactg tgcccagcct     540
tggttgcttt tttaacagat aacagtgtgc tcatagaaac tgctttgaca tgactgcaat     600
catgtgcttc atagaaactt aattagatta taccactaga gtcttcagat ttttatactt     660
tttttttttg aaacggagtc tcactctgtc accaggctgg agtgcagtgc cgcaatctcg     720
gctcactgca acctccgcct cccaggttca gcaattctc ctgcctcagc ctcccgagta      780
gctgggatta caagtgcgca ctaccacacc cagctaattt ttgcattttt acttgacagg     840
gtttcaccat gttggctagg atagtttcac caggatctct tggcctcatg atcagcctgc     900
ctcggcctcc caaagtgctg ggattacagg tgtgagccac cgtgcccagc ctatacttcc     960 cttttttgaat accatttggc gttttgaaga attaacagct tgtgaacgt ggcagtgctt     1020 gtgattcagg cttccattga gaccaagggg agaacctggt tgcaggacaa acagacggac    1080
agcgtgtggc agtgtttaaa tgctcttctg aaggctgata cgacagctct ctgtgcactg    1140
attgcatacg catcccaaga ttatattatt gttttctact gctatgtgtc acactttgcc    1200
aaacaggatg tggaaaatga ataagcggtt tcttaggca cttcttaaca gacaattggt     1260
caaaatgaac tccattgctt aagaaacaca taaacaccat ttagtcactg aacatagcta    1320
tatgtatggt tgttactatg ggaaatcttg ttttgccaat tttctttgaa aattctggca    1380
gaccaaggtt cttttttgttt acataatact tgaaaaataa aaatgaacaa gctaacaaac   1440
taccaagttt tcacttacat aaatgtagtt gcatacagaa aatgtgactg tgaattaatt    1500
tttctaggac ttttaaacta taagcactat ttgcacaaaa gagaaccaat ctatcaatta    1560
caaactcaca taatttttaca gatttttttt ttcctacaca gcacataaaa cagaaggaat   1620
ttgaagccac cctccaaaca caggggaagg aggctgtgtg tatatcctca ttgtctttca    1680
cattctaagg tggttccact cagtgactga aatccttaag cgttgtatta gtctgcttgg    1740
gctaccataa cagcagctta aactgttgtt tagccactca gacttaaaca acagaaattt    1800
atttccttat agttctggag gctggaagtt caaggtgccg gcaaggttgg tttctggtga    1860
gacctctctc cctgtcttgc agatggctgc ctcctccctg tgtcctcata gagcctgtct    1920
tctgctttta cacttctggt gtcatcttcc tttttttttt tttttttttt ttttgagaca    1980
gagtctcgct ctatcgccca ggctggagtg cagtggcccg atcgatctcg gctcactgca    2040
acctctgcct cccaggttca gcaattctc ctgcctcagc ctcccaagta gctgggacta     2100
caggtgcccg ccatcatgcc tggctaattt ttgtattttt agtagagaca gggtttcacc    2160
atattggcca ggctggtctc gaactcctga ccttgtcatc tgcctgcctc ggcctcccaa    2220
agtgctagga ttacaggcgt gagccaccgc acccggcctc ttcctcttct tataaggaca    2280
ccagtcctat tagattaggg ctccaccctc ataacctcat ttgaccttaa ctattatttc    2340
```

```
tttaaagcac ctatttccaa atatagtcac tttaggggtt agggcttcaa aagatgaatc    2400
tgagggagct caattcagta aatagcagta gtcattaatg gacaatgtat acaaagataa    2460
tttcgtgatt actgtcctta tgcataaacg tcctcagtgt tccactgcgt ttatccagat    2520
ttagtatcac aaagactttg ctctgagaaa aatgtgattt tttttttttt tttttttttg    2580
agacggagtc tcgctctgtt acccaggctg gagtgcagtg gcgcgatctc ggctcactgc    2640
aagctccgcc tcccgggttc acgccattct cctgcctcag cctccggagt agctgggact    2700
acaggcgccc gccactacgc ccggctaact ttttgtatt tttagtagag acggggtttc     2760
accatgttag ccaggatggt ctcaatctcc tgacctcgtg atccacctgc ctcagcctcc    2820
caaagtgctg ggattacagg catgagccac cgcgcccagc agatttttt ttttttttt     2880 gagatggagt cttgctctgt tgcccaacct ggagtgcagt gttatgattt tggctcactg    2940
caacctctac catgttcaag cgattctccc acctctgcct cccgtgtagc tgggatcaca    3000
ggcacacgcc accacaccta gctactttt gtatttttag tagaaatggg gtttcaccat     3060
gttggccagg atggtcccga actcctgacc tcaagtgatc ctcctgcctc ggcctccaaa    3120
gtgctgggat tacaggtgtg agccactgtg cctggccaaa aatgtgattt cttatttccc    3180
acattgccaa ttccatttca attaactata atagctatgt ctattgagca ctcaagcgta    3240
ttctagaaac tgttcctgat tctggggata tatccatgaa tcaactatag tccctgttat    3300
taagtaatcc gtagtctgac taaaccatta gaaattaaaa aaaatggct actttcaaag     3360 acatcttgga gttcaggagt cccacactgc gaaccatatt acctaataat ccaacctgct    3420
tgtaattcac ttatttaacc aatatttatt gagtgccaac tttgagccta agatacagca    3480
gtaaacaaat gcataaagtc cctgtcccca tgaaacttgt attctaatgg aaaaaacaga    3540
aaacaaacag atataggatg taatatcagg tagggataaa tactttgaat tcaaacaaaa    3600
gtatacgtag tcagggttcc ccagagagac acagccaatc gatacataga tatataagag    3660
agggtttatg agttagaaag ggctcacatg attacagagg ctgagaagtc ccacaacaga    3720
ttgtctgcaa gctggagacc cagggatact ggtagcatgg ctcagtccaa gtcccaaagt    3780
ctcagaatca ggaaagctga tgatataatt cttagcccaa aggccttaga accccagcgg    3840
tgacggaaag gctgatgtag gtcctggcgt cctgagaccc aacagcctgg gatcctgaaa    3900
tccaagggca ggaatggaag cgtgtattcc agctccaaga gagtaagacc aatttgcctt    3960
tcttccgttt tgttccaag ccaactgcac gttgagggcg gatggttccc tcttagccca     4020
ttcagtcata tatcaatctc ttctggaaat accctcacag acacactaac aaataatgcc    4080
tttccagttc tctaggtatt ctttaatcca gtcaagctga cacctaaaat taaccatcac    4140
aaaagttaag gagaaagaag acaacttgta ggagaggctg ctatgcaaga cagtgtgtga    4200
aggaagggct ctctgaagag gttaatatct gagcagagac ttgaatgaag tgaagaagtg    4260
agccatgtgg gtatggggaa tacaacttcc aggtagagaa gacaagtgtg gtgtgtatca    4320
cggtcagcaa agaagccatg tgacagagaa gggtgggcca gggagagacg gataagtgat    4380
ctaactcctg aggaggtggc ctggccagga gctagagcat gaggatctcg taggatttta    4440
ttctgcaagg tgaaaagcca ttgtattagt ctgttcacaa accccagact aggcaattta    4500
caaaagaaag agaggtttaa tggacttaca gttccacatg gctggggagg cctcacaatc    4560
atggcgaaag gcaatgagga gcaagtcacg tcttacgtgg atggcaggca aagacaaaga    4620
cagcttgtgc agagaaactc cccttatag agccatcaga tcctgttaga cttatcacta     4680
tcacgagaac agcacgggta agacctgtcc ccatgattca gttacctccc actgggtccc    4740
```

```
tcccacaacg catgggaatt caggatgaga tttgggtggg gacacaacca aaccctatca    4800
ttccacccat ggcccctccc aaatttcatg tcctcacatt tcaaaaccaa tcacaccatc    4860
ccaacagtcc ctcaaagtct taaatgattt cagcattaac tcaaaagtcc acagtctaat    4920
gtctcatctg agacaaggca agtcctttcc gtctatgagc ctataaaatc caaagcaagt    4980
taattacttc ctagatacaa tgggggtaca ggcattgggt aaatacagcc attccaaatg    5040
ggataaattg gtcaaaacaa agaggctaca ggcccatgag agtccaaaat ccagtggggc    5100
agtcaaatct taaagctcca aaatgatctc ctcttgactc cacatctcac atccaggtca    5160
tgcagatgga aggggtgggt tcccatggtc ttgggcagct ctgcccctgt acctttgcag    5220
ggtacagcct ccctctcagc tgctttcatg ggctggcatt gagtgtctgc aacttttcca    5280
ggtacacggt gcaagctgtc ggtggatcta ccattctggg gtctggagga cctcttctca    5340
cagctccact aggtggtgcc ccagtaggga ctgtgtgtgg ggtctctgac cccacatttc    5400
ccttctgcac tgccctggca gaggatctcc atgagggccc tgcccctgca gcaaacttct    5460
gcctgggcat ccaggcattt ccgcacatcc tctttaatct aggcgaaggt ttccaaaccc    5520
cagttcttga cttctgtgca ctcgcagtct caacaccaca tggaagctgt caaggcttgg    5580
ggcttgcact ccccgaagct acagcccaag ctctaccttg cctcctgtca gtcatggttg    5640
ggagtggctg ggatgcaggg caccaagtcc ctaggctgca cacagcatga ggaccccggg    5700
cctggccaac aaaaccattt ttcctgata tctctggacc tgtgatggga ggggttgcca    5760
taaagacctc tgacatgccc tggagacatt ttccccattg tcttgggaat tagcatttgg    5820
ctcctgttac tcatgcaaat ttctgcagcc agcttgaatt tctcctcaga aaatgggaat    5880
ttttcttttc tatcacattg tcaggctgca aattttccga acttttatgc tctgcttccc    5940
ttataaaact gaatgtcttt aacagcaccc aagtcacctc ttgaatgctt tgctgcttag    6000
aaatttctcc tgccagatac tctaaatcat ctctctgaag ttcaaagttc tacaaatatc    6060
tcgtgcaggg gcaaaatgcc gccagtatct ttgctaaaac ataacaagag tccccttgc    6120
tccagttccc aacaagttcc tcatttccgt ctgagaccac ctcagcctat ggactttatt    6180
gtccacagtg ctatcagcat tttgggcaaa gccattcaac aagtctctag gaagttccaa    6240
actttcccac atttgcctgt cttcttctga gccctccaaa ctgttccaaa ccctgcctgt    6300
tacccagttc caaagtcaca tacccatttt tgagtatcta cggcagcacc ccactctact    6360
ggtaccaatt tagccactga agtagttgga gaacagaagt aatagactct ggtttacatt    6420
gtaaaagctt ctctgtggct gctgtgtgaa gaaatatat gagaatgaag ccccaagatg    6480
aagcagggac acagttgcag tggttagagt aagaaatgct gctggctggc actgaagtga    6540
tagcctggag gtttgtgtgt gcacatgcat gtgtatgtgt tttacgatag taggcccaac    6600
agatactgta atccacactt gttttttttt tttttttgag acagagtctc acctgttgcc    6660
tagactagaa tgcagtggca caatcttggc tcactacaac ctccacctcc caggttcaaa    6720
caatccttgt gcttcagcct cccgagtagt tgggattaca ggtgtgtgcc accgtgccca    6780
gctatatttt ttgtattttt agcagagatg ggattttgcc acattggcca ggctggtctt    6840
gaactcctgg cctcaagcaa tcctcccacc ttagcctccc aaagtgctga gccaccacac    6900
ctggccgcaa ctgatttta atcatgaaat gacacataca tttaaaaaac ccaataccta    6960
taatattcct ggctagtact cttcacatct atatcatcaa aaacaaagaa agtatgtgaa    7020
actgacacag ccaaggggag actaaggaga cataacaatt aactgtaatg tggtattctg    7080
gagggggatcc tggaacagaa aaagacatta ggcaaaaaac taaagaaatc tgaataaaat    7140
```

```
gtggatgtca gttaataata atgtatcata ttagtccagt aattgtaaca aatatatccca    7200 ataatgaaag ccattaatta tagggaaaat ggaggggtta atatgggtgg ctggcttttg    7260
ctatttctag cagctccatt ttatctacaa aagacaaaca ttcattaagt cccaaaaagg    7320
taaagaatga caaattaagc atgtatctta ttagtaagag taatataaag atgctcactc    7380
atatttataa atatttgaca atgatgttaa ggccagaaaa gagaaaaaag ggtaggggca    7440
aaaaacgcaa agagaaagga gttagtatct tttctcccgc actcattagc tattaaaaga    7500
ggatgtttgt ttaaagctgc tcagagctgg taaactaatg ttaagtcact aacgggaatt    7560
taaaaggttt cattaagaac tgcctgcact agattcctcc accctgagac attaaacaat    7620
cacgataaac ctcctgagtg gtaagaacgt gtccatttaa aaacaggcta tagattgtca    7680
tgcagtttta tctactaatc ggctaatgca ccgccaaaaa caaacaaaaa aacccaaagg    7740
gatgaaagtt tcatccatca aaggaaacaa cagtcacctt ggttcccatc ccactcatat    7800
actgccgccg tacatgtcaa tcagatgaac ctgtgcgtat ctcttaatga caattgaccc    7860 accttttttaa ctgaagtgaa gggggggtct gctccgcgac cacttcctgg atctctccct    7920
tcaccctctg tgttctttcg ggtgcaccat cgggtcaaag ccgcagcaac gccgtctctg    7980
tgtgatcgca tgtgcccttc tgcacacgac cttcccccga gagtgaccag ctaccggaca    8040
ggcaccaagg agggctaccg agcacctccc ggaccggcgg ctgcaggatc gcgagcgcct    8100
ccgctaggga gaccgcacgt tgcgcctgtg cttcctgcgg tggcgccttc tgcaaggaga    8160
cctcgaccct gctccctctc cggggctgga tctgactcct tgacggtgat tccagacgcg    8220
agacccaaac tgacggcttc tagaagaggg gcgagcccgg ccgcaagtct ttcacgtagc    8280
taagtcatcg ttgcttccgg cttcttaccg ttctcccctt tgtaaacggt tacctcccga    8340
aaacccaggc tctcctccaa cagtggttct caagcgaggc gatcttcccc gggaggggat    8400
atttggcaaa gtctgggggc attttttggtt cactggggct gctacttgca tccactgggt    8460
agaggcgggg gatgcagcta cacaacctgc gaagcacggg acagcaccct ccccaaccca    8520
gacagaatta gccggcccaa aacctcagta gtgcccaggc tgagaaaccc tgccttaaac    8580
aaacaacaaa gaaaggccaa gtcccataag tgggtcaccg cgccgagact ggggtccacg    8640
ggacacccca gccacgccaa gccgggaagt ccccgcctcc tggagctgaa cccgcccctc    8700
tcccagaggt ggagctgcgg ggggcgggaa caggcacgga gaaaataaac aagactaaaa    8760
agtcctgagt agcgctgtgt ggccgcaaac ctgaacccac cttttgcacc acgcgggacc    8820
cggcactctt cctgccaccc acccctgaga gggctgcgcg gccgacccca gtactagaaa    8880
acactcgtca cctcactcaa gacgggtacg aaggccaacg gacgccttcc tttagaacgc    8940
tcagcacaca gagcaacttc tcacgcctac tctcaaatgg cgtactccaa actagcactc    9000
ccgacgtcca gctgtgaacc cagagcggcg gaaagcccct gaacccagcg cccgggcatg    9060
cgcagacgcg ttgttgtggt gggcgtggct ccctccggac ccggcgcccc gccctccgcc    9120
ccgtgtccgc atgcgcgact gagccgggtg gatggtactg ctgcatccgg gtgtctggag    9180
gctgtggccg ttttgttttc ttggctaaaa tcggggagt gaggcgggcc ggcgcggc    9238
```

<210> SEQ ID NO 21
<211> LENGTH: 1249
<212> TYPE: DNA
<213> ORGANISM: Homo sapiens

<400> SEQUENCE: 21

```
ctgatctaca taggaattgt tttcaagaca tttctgcatt cctctagtga cagggtgctc        60
actacctcat gagtatttca gtggacaact gtaatggtca ataaagtatc cactttccac       120
ctccctgcag ctcctggccc tggctttatt ctctggggct ccacacattc agtttacact       180
cagtggccag tggctgggac cattgtagaa aataaggaaa ctccaattcc ttccttcttt       240
tcttcctctt tcatctcttc ctccctctct acatccctct ctctcttcct tccttcctcg       300
acacttacca tgtaccagac cttctgccag gcacatggat gggagcacag gggaagttgg       360
ctgcagggtt agaactaagt cccaagcccc taaagctca tgccagggga ctggactgtc        420
cagtactgag ggatggggat gctgaggctg gtggccttcc tcaaatgcac tgtagtgccc       480
caggcagagt cctgggctgc cctgtgagga ggtgaccaga ggtagagcaa cttcacccta       540
aggctggatc aggatcccct ccaggttttt actagagcca aacccacatc tcctttctct       600
tctgccaccc cccttaaaa tgcttagaaa cacatagatt taaatacaaa ttcaaatgta        660
agtaatttca actgtgtaac tatgaggagt cagttctacg tgggtcctat ctgtatcctc       720
cccagggctc agctccattc tttgcttca ttcattctca ttcaatacat tgttgttaag        780
agctcactgg gtgccctctc tgtcatgtag taaggtttta aaagaaagc ctcttctgag        840
cttcagtttc cttattcata aataggagt attgatccgt tccttgcttt tcttacaagg        900
atatgctgaa gatgactgaa gtacagagta agaaggatt atgtttgggt gtcaaaggaa        960
tagaatgccc tctttcaaac tgagcacagc aggaacctgt aacaggaaca cagcaacttg      1020
ttgaatgaat gacaatattg gaaaacatac atttcctccc ctccccatca tagtccctct      1080
gcttccgtgt taactccata gagaggccag cacaaccagc cttgcagcct gagataaggc      1140
cttttggcggg tgtctcccct atcgctccct caagccctca gtaggtgtt ggagagaggg      1200
gtgatgcctg gtgctggtgg aaccctgca cagagacgga cacaggatg                  1249
```

<210> SEQ ID NO 22
<211> LENGTH: 699
<212> TYPE: DNA
<213> ORGANISM: Homo sapiens

<400> SEQUENCE: 22

```
ctagagaggg aagttttga aaattaaaca ctgtctaatt ttctgcaaag ttttattca         60
tgaattaaga gtatttccct tagtccatta ttcccaaggc aaatatggaa gtttgatcat       120
atgctaatca tactaaagct ggattctctt taagagattg agaaattaaa aggcaaaagc       180
tgatatatca tgtttagtta tactgtgagt cttataagaa gctgggaggc aaccccatta       240
actcaccaga atacagaact cagtctcaca acttaaatat aattcctctc aaaccttttc       300
ctcaaagtta aattctgaaa ataatcttgt gattaagaga agaaggctgt ccaccaatgg       360
acttatctgt tatttcttcc ttattgtgag cttaatggca tgacaaagca gaggcaaaga      420
ggcatacatc aattcttcaa agtaggaagt caaaaaggtc agagcttcca cagcatggca       480
acagctttgc agatgcccac atcgtgatag ttgaaatagc aaagcccagc aaaggttaaa       540
gctgaaaatg ccaaaagccc tgccttggca gctttctgcg aggcatcccc atgaacatag       600
tcagtaacaa cttgtccaag gccccagtga ccatgaagag tgagggctgc agccaggaa       660
tagtccgtcg cagagcaagg attcaaataa gcagccgga                             699
```

<210> SEQ ID NO 23
<211> LENGTH: 699
<212> TYPE: DNA
<213> ORGANISM: Homo sapiens

<400> SEQUENCE: 23

```
ctagagaggg aagttttttga aaattaaaca ctgtctaatt ttctgcaaag ttttttattca      60
tgaattaaga gtatttccct ttgtccatta ttcccaaggc aaatatggaa atttgatcat     120
gtactaatca tactaaagct ggattctctt taagagattg agaaattaaa aggcaaaagc     180
tgatatgtca tgtttagtta tattgtgagt cttataagaa gctgggaggc aaccccatta     240
actcaccaga atacagaact cagtctcaca acttaaatat aattcctctc aaaccttttc     300
ctcaaagtta aattctgaaa ataatcttgt gattaagaga agaaggctgt ccaccaatgg     360
acttatctgt tatttcttcc ttattgtgag cttaatggca tgacaaagca gaggcaaaga     420
ggcatacatc aattcttcaa gtaggaagt caaaaaggtc agagcttcca cagcatggca     480
acagctttgc agatgcccac atcgtgatag ttgaaatagc aaagcccagc aaaggttaaa     540
gctgaaaatg ccaaaagccc tgccttggca gctttctgcg aggcatcccc atgaacatag     600
tcagtaacaa cttgtccaag gccccagtga ccatgaagag tgagggctgc agccagggaa     660
tagtccgtcg cagagcaagg attcaaataa gcagccgga                              699
```

<210> SEQ ID NO 24
<211> LENGTH: 699
<212> TYPE: DNA
<213> ORGANISM: Homo sapiens

<400> SEQUENCE: 24

```
ctagagaggg aagttttttga aaattaaaca ctgtctaatt ttctgcaaag ttttttattca      60
tgaattaaga gtatttccct ttgtccatta ttcccaaggc aaatatggaa atttgatcat     120
gtactaatca taataaagct ggattctctt taagagattg agaaattaaa aggcaaaagc     180
tgatatatca tgtttagtta tattgtgagt cttataagaa gctgggaggc aaccccatta     240
actcaccaga atacagaact cagtctcaca acttagatat aattcctctc aaaccttttc     300
ctcaaagatt aaattctgaa ataatcttg tgattaagag aagaaggctg tccaccaatg     360
ggcttatctg ttatttcttc cttattgtga gcttaatggc atgacaaagc agaggcaaag     420
aggcatacat caattcttca agtaggaagt caaaaaggt cagagcttcc acagcatggc     480
aacagctttg cagatgccca atcgtgata gttgaaatag caaagcccag caaggttaa     540
agctgaaaat gccaaaagcc ctgccttggc agctttctgc gaggcatccc catgaacata     600
gtcagtaaca acttgttcaa ggccccagtg accatgaaga gtgagggctg cagccgggaa     660
tagtccgtcg cagagcaagg attcaaataa gcagccgga                              699
```

<210> SEQ ID NO 25
<211> LENGTH: 994
<212> TYPE: DNA
<213> ORGANISM: Homo sapiens

<400> SEQUENCE: 25

```
ttgtatctct ttttacagct acctcccatt tcccttctat ttcaagctag taacacagtt      60
ttcttttaaa ttcatttatt taaatgtaaa aataagtcta tttggagaaa aaaaatttt     120
aatagcatct ctggaatgcc agtatggcta aattcatgaa tgttgtcctc aaatgctgaa     180
atctgggaag catctggcca agctttgtgg acaggcctgc ctagtttgaa tcccaagagc     240
```

```
cactcattcc gagccacaaa acattggaat tcttggttca cttccctaac ctgaacttgt    300
cctctgtgaa atagggacat taatagctca ctcacagggc tgctgtgagg acatgtgttg    360
agctgagggt ctcgccaggg gagaccctgt gcagggagac tgttatcatg gtgatggatt    420
tctgcttcat tcatttcttt ttccagacag catcatatag aatgagttgt ggggtggcag    480
tcagcaggtt tgggtttatc ctctattctg ccacttatta cttaaaaaaa aaacccaac     540 ttatatagta taagctatat ccagaaaagt gcaaatatca tacaagtacc atttgatgaa    600
tcttctgata tccccacata accaacaccc agaacctctt cttgtctcat tccaggataa    660
ccactaacct gacttctaac agcatcagtc agttttgtct gttttttgtac attatatatg    720 tgatggtttg aatgtgtccc ccaaatttca tgtgctagaa acttaatcct tcaattcata    780
tgttgatgct atttggagga agggccttttg ggaagtaatt aggattagat aaggtcatgg    840
ggtgaggtat gatggcactg gtgacttata agaagagaaa gagaaatctg agctggcatg    900
ctcttgccct ctcaccgtgt gatgacttct ccatgtcatg atgcagcaag aaggccctca    960
ccagatggtg gcaccatgct tttggacttc ccag                                994
```

```
<210> SEQ ID NO 26
<211> LENGTH: 1000
<212> TYPE: DNA
<213> ORGANISM: Homo sapiens

<400> SEQUENCE: 26
ttgtatctct ttttacagct acctcccatt tcccttctat ttcaagctag taacacagtt     60
ttcttttaaa ttcatttatt taaatgtaaa aataagtcta tttggagaaa aaaaattttt    120
aatagcatct ctggaaggcc agtatggcta aattcatgaa tgttgtcctc aaatgctgaa    180
atctgggaag catctggcca agctttgtgg acaggcctgc ctagtttgaa tcccaagagc    240
cactcattcc gagccacaaa acattggaat tcttggttca cttccctaac ctgaacttgc    300
cctctgtgaa atagggacat taatagctca ctcacagggc tgctgtgagg acatgtgttg    360
agctgagggt ctggtcaggg gagaccctgt gcagggagac tgttatcatg gtgatggatt    420
tctgcttcat tcatttcttt ttccagacag catcatatag aatgagttgt ggggtggcag    480
tcagcaggtt tgggtttatc ctctattctg ccacttatta cttaaaaaaa ccccaaaaaa    540
cccaacttat atagtataag ctatatccag aaaagtgcaa atatcataca agtaccattt    600
gatgaatctt ctgatatccc cacataacca acacccagaa cctcttcttg tctcattcca    660
ggataaccac taacctgact tctaacagca tcagtcagtt ttgtctgttt ttgtacatta    720
tatatgtgat ggtttgaatg tgtcccccaa atttcatgtg ctggaaactt aatccttcaa    780
ttcatatgtt gatgctattt ggaggaaggg ccctttgggaa gtaattagga ttagataagg    840
tcatggggtg aggtatgatg gcactggtga cttataagaa gagaaagaga atctgagct     900 ggcatgctct tgccctctca ctgtgtgatg acttctccat gtcatgatgc agcaagaagg    960
ccctcaccag atggtggcac catgcttttg gacttcccag                          1000
```

```
<210> SEQ ID NO 27
<211> LENGTH: 999
<212> TYPE: DNA
<213> ORGANISM: Homo sapiens

<400> SEQUENCE: 27
ttgtatctct ttttacagct acctcccatt tcccttctat ttcaagctag taactcagtt     60
ttcttttaaa ttcaattatt taaatgtaaa aataagtcta tttggagaaa aaaaatttta    120
```

```
atagcatctc tggaatgcca gtatggctaa attcatgaat gttgtcctca aatgctgaaa      180
tctgggaagc atctggccaa gctttgtgga caggcctgcc tagtttgaat cccaagagcc      240
acccagtcca agccacaaaa cattggaatt cttggttcac ttccctaacc tgaacttgcc      300
ctctgtgaaa tagggacact aatagctcac tcacagggct gctgtgagga catgtgttga      360
gctgagggtc tcgccagggg agaccctgtg cagggagact gttatcatgg tgatggattt      420
ctgcttcatt catttctttt tccagacagc atcatataga atgagttgtg gggtggcagt      480
cagcaggttt gggtttatcc tctattctgc cacttattac ttaaaaaaac cccaaaaaac      540
ccaacttata tagtataagc tatatccaga aaagtgcaaa tatcatacaa gtaccatttg      600
atgaatcttc tgatatcccc acataaccaa cacccagaac ctcttcttgt ctcattccag      660
gataaccact aacctgactt ctaacagcat cagtcagttt tgtctgtttt tgtacattat      720
atatgtgatg gtttgaatgt gtcccccaaa tttcatgtgc tggaaactta atccttcaat      780
tcatatgttg atggtttttg gaggaagggc ctttgggaag taattaggat tagataaggt      840
catggggtga ggtatgatgg cactggtgac ttataagaag agaaagagaa atctgagctg      900
gcatgctctt gccctctcac tgtgtgatga cttctccatg tcatgatgca gcaagaaggc      960
cctcaccaga tggtggcacc atgcttttgg acttcccag                             999
```

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: artificial
      primer

<400> SEQUENCE: 28

```
ggctaaatat tttgatgacc aagtt                                             25
```

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: artificial
      primer

<400> SEQUENCE: 29

```
gcagccaact tcccctgtg                                                    19
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: artificial
      primer

<400> SEQUENCE: 30

```
gctctacctt ggtcacctcc                                                   20
```

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: artificial
      primer

```
<400> SEQUENCE: 31
aggtcacatc catttatccc actg                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 32
agaagatggg ggaatctttt tcct                                              24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: artificial
      primer

<400> SEQUENCE: 33
ttgtgactgg gctagaaaga aggtg                                             25

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 34
tgttgcctgc atttgtacgt gag                                               23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: artificial
      primer

<400> SEQUENCE: 35
ttctgtctgg gttggggagg g                                                 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: artificial
      primer

<400> SEQUENCE: 36 ggagggggtta atatgggtgg c                                                21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: artificial
      primer
```

-continued

```
<400> SEQUENCE: 37
tttgtcctgg ttgcctgtgg tc                                              22

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 38
caaatcctgt tgactggtct cgg                                             23

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 39
aacggctcca tcacccctaa ag                                              22

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 40
cccactccta gataccaacc caag                                            24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 41
ctttatgcac tgcctcgttg aatc                                            24

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 42
ttgactggtg tggttgctgt tg                                              22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: artificial
      primer
```

```
<400> SEQUENCE: 43
gcagaaaggg gagttgatgc tg                                              22

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 44
ctgacaaagt tgagagccca ctg                                             23

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 45
ttaagcctac atccacatgc tgag                                            24

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 46
ccttggtctg ccagaatttt ca                                              22

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 47
gtttggcatc ataggagatt tggc                                            24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 48
cctgtcccca tgattcagtt acc                                             23

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: artificial
      primer
```

```
<400> SEQUENCE: 49
acgtacaaat gcaggcaac                                              19

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: artificial
      primer

<400> SEQUENCE: 50
cctttttttg tttgtttttg gcggtgc                                     27

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: artificial
      primer

<400> SEQUENCE: 51
agcttactgg atgaccacca                                             20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 52
gactgggggg aaaagcgcaa tac                                         23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: artificial
      primer

<400> SEQUENCE: 53
gtattgcgct tttcccccca gtc                                         23

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 54
tgacttgctc tcatcccaca tg                                          22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: artificial
      primer
```

```
<400> SEQUENCE: 55
gggcttgaag caagtaaatg gaag                                          24

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: artificial
      primer

<400> SEQUENCE: 56
gctatcaata ttttcttggt tacagacac                                     29

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: artificial
      primer

<400> SEQUENCE: 57
gttcactgcc ataagtcttc agtgc                                         25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 58
tggccgcact gaagacttat gg                                            22

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 59
cagctgcatc tatgataatc cacc                                          24

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 60
atggacaagt ccgaggtgat ag                                            22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: artificial
      primer
```

```
<400> SEQUENCE: 61
atcacctcgg acttgtccat tc                                              22

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 62
gcaatcagag atccaaaggc caac                                            24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: artificial
      primer

<400> SEQUENCE: 63
gttggccttt ggatctctga ttgc                                            24

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: artificial
      primer

<400> SEQUENCE: 64
gacatagtat accctggaat tgctgt                                          26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: artificial
      primer

<400> SEQUENCE: 65
acagcaattc cagggtatac tatgtc                                          26

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: artificial
      primer

<400> SEQUENCE: 66
ctcccccgat tttagccaag aa                                              22
```